United States Patent [19]

Yatsunami et al.

[11] Patent Number: 5,026,856

[45] Date of Patent: Jun. 25, 1991

[54] ISOINDOLINE DERIVATIVE

[75] Inventors: Takashi Yatsunami; Akira Yazaki; Satoshi Inoue; Hitoshi Yamamoto; Masaharu Yokomoto; Jun Nomiyama; Shuichiro Noda, all of Hiroshima, Japan

[73] Assignee: Wakunaga Seiyaku Kabushiki Kaisha, Osaka, Japan

[21] Appl. No.: 356,059

[22] Filed: May 23, 1989

[30] Foreign Application Priority Data

May 23, 1988 [JP] Japan .................... 63-125496
Nov. 2, 1988 [JP] Japan .................... 63-277892

[51] Int. Cl.$^5$ ............... C07D 401/10; C07D 471/04; C07D 471/06; C07D 513/04
[52] U.S. Cl. .................... 546/156; 540/550; 540/556; 544/32; 544/99; 544/101; 544/344; 546/83; 546/94; 546/123; 548/482
[58] Field of Search ........................ 546/156

[56] References Cited

U.S. PATENT DOCUMENTS 4,767,762 8/1988 Chu ........................... 546/83
4,908,366 3/1990 Schriewer et al. ............ 546/156

OTHER PUBLICATIONS

Jorois et al., Chemical Abstracts, vol. 110, No. 135105 (1989).

Primary Examiner—Nicholas S. Rizzo
Assistant Examiner—E. Bernhardt
Attorney, Agent, or Firm—Oblon, Spivak, McClelland, Maier & Neustadt

[57] ABSTRACT

Isoindoline derivatives represented by the formula (I) and their salts are disclosed.

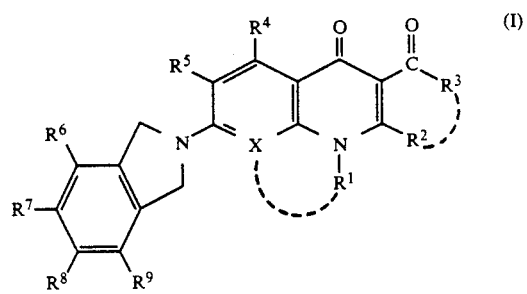

There are many varieties for the compound depending on the types of residues $R^1$–$R^9$ and X. The compounds can be prepared from quinoline derivatives of the formula (II) and an isoindoline derivatives of the formula (III). The compounds of formula (I) and their salts have excellent antibacterial activities against both gram positive and gram negative microorganisms. They can be used as a medicine, an agrichemical, and a food preservative.

2 Claims, No Drawings

1

ISOINDOLINE DERIVATIVE

BACKGROUND OF THE INVENTION

1. Field of the Invention

This invention relates to a novel isoindoline derivative which is a superior synthetic antibacterial substance and to a process for its preparation.

2. Description of the Background

A number of pyridonecarboxylic acid derivatives as synthetic antibacterial materials have been synthesized in recent years. These include norfloxacin (Japanese Patent Laid-open No.141286/1978), enoxacin (Japanese Patent Laid-open No.31042/1980), ofloxacin (Japanese Patent Laid-open No.46986/1982), ciprofloxacin (Japanese Patent Laid-open No. 74667/1983), and the like. A feature common to these compounds is that they have a quinoline structure or a naphthyridine structure, both having a fluorine atom substituted at 6 position and a secondary amino group at 7 position. In particular, introducing a piperazine group or a pyrrolidine group to the 7 position of a quinoline or a naphthyridine structure is considered to effect enhanced antibacterial activitites. These compounds, however, are considered not to be complete in their effects of antibacterial activity, absorptivity through enteric canal, and metabolic stability. In addition, their side effects have been a problem.

The present inventors have undertaken extensive studies in order to develop an antimicrobial substance having a superior effects without the problem of side effects and useful for clinical purposes. As a result, the inventors have found that compounds having an isoindoline ring at 7 position of a quinoline or naphthyridine structure show extremely strong antibacterial activity not only against gram negative microorganisms but also against gram positive microorganisms. This finding has led to the completion of this invention.

SUMMARY OF THE INVENTION

Accordingly an object of this invention is to provide isoindoline derivatives represented by the formula (I) or salts thereof.

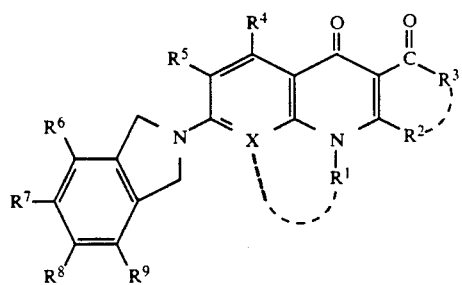

Various substituents in formula (I) have the following meanings:

$R^1$: represents a lower alkyl group which may have a substituent, a cyclo-lower alkyl group, a lower alkenyl group, a mono- or di-lower alkylamino group, a lower alkoxy group, an aralkyl group which may have a substituent, or a phenyl group which may have a substituent [C(1') and C(2') atoms of the phenyl group and N(1), C(8a), and C(8) atoms of the quinoline ring may form a six-membered ring via an oxygen atom, a sulfur atom, or a group $-NR^{15}-$ which are attached to 8-position of the quinoline ring ($R^{15}$ represents a hydrogen atom, a lower alkyl group which may have a substituent, a lower alkanoyl group which may have a substituent, an aroyl group which may have a substituent, an aryl group which may have a substituent, or an aralkyl group which may have a substituent)].

$R^2$: represents a hydrogen atom, a mercapto group, or a lower alkylthio group.

$R^3$: represents a hydroxy group, a group $-OR^{10}$ ($R^{10}$ represents a carboxy protective group), an amino group, a mono- or di-lower alkylamino group; or $R^2$ and $R^3$ may together constitute a group $-NH-S-$ to form a five-membered ring.

$R^4$: represents a hydrogen atom, a halogen atom, a hydroxy group, a lower alkoxy group, a lower alkyl group, an amino group, or a mono-, di- or tri-lower alkylamino group.

$R^5$: represents a halogen atom, a hydroxy group, or a lower alkoxy group.

$R^6$, $R^7$, $R^8$, and $R^9$: these groups may be the same or different and individually represent a hydrogen atom, a halogen atom, a lower alkyl group which may have a substituent, a cyclo-lower alkyl group, an aryl group which may have a substituent, an aralkyl group which may have a substituent, a carboxy group, lower alkoxycarbonyl group, a mono- or di-lower alkylcarbamoyl group, an arylcarbamoyl group which may have a substituent, an aldehyde group, a nitrile group, a lower alkanoyl group which may have a substituent, an aroyl group which may have a substituent, a hydroxy group, a lower alkoxy group which may have a substituent, an aryloxy group which may have a substituent, a lower alkanoyloxy group, an aroyloxy group which may have a substituent, an amino group, a mono-, di- or tri-lower alkylamino group, a lower alkanoylamino group which may have a substituent, a lower aroylamino group which may have a substituent, a nitro group, a lower alkylsulfonyl group, an arylsulfonyl group which may have a substituent, a mercapto group, a lower alkylthio group, a sulfonamide group, a lower alkylsulfonamide group, a lower arylsulfonamide group which may have a substituent, or a heterocyclic group which may have a substituent.

X: represents a nitrogen atom or a group $=CY-$ [wherein Y represents a hydrogen atom, a halogen atom, a lower alkyl group, or a lower alkoxy group, or may form a ring together with $R^1$, in which case Y and $R^1$ constitutes a group:

$$-A\left[\begin{array}{c}R^{11}\\|\\C\\|\\R^{12}\end{array}\right]_n \begin{array}{c}R^{13}\\|\\-C-CH-B\\|\\R^{14}\end{array} \text{ or } -A-CR^{11}=C-B,$$

wherein A represents an oxygen atom, a sulfur atom, a methylene group which may be substituted with a lower alkyl group, a carbonyl group, or an imino group $N-R^{15}$ ($R^{15}$ has the same meaning as defined above), B represents a hydrogen atom, a lower alkyl group, a halo-lower alkyl group, or an aryl group which may have a substituent, or an aralkyl group which may have a substituent, $R^{11}$, $R^{12}$, $R^{13}$, and $R^{14}$, which may be the same or different, individually represent a hydrogen atom, a lower alkyl group which may have a substituent, an aryl group which may have a substituent, an aralkyl group which may have a substituent, an amino group, a mono-, di- or tri-lower alkylamino group, a lower alkanoylamino group, a hydroxy group, a lower alkoxy group, a lower alkanoyloxy group, a halogen atom, a nitrile group, a carboxy group, a lower alkoxycarbonyl group, or a heterocyclic group which may have a substituent, and n denotes an integer of 0 or 1].

Another object of this invention is to provide a process for preparing isoindoline derivatives of the above formula (I) or salts thereof, which comprises:

reacting a compound represented by the formula (II):

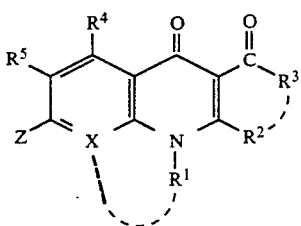

wherein $R^1$, $R^2$, $R^3$, $R^4$, $R^5$, and X have the same meanings as defined for formula (I) and Z represents a reactive leaving group, with a compound represented by the formula (III):

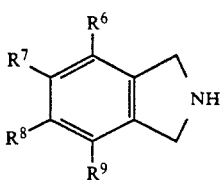

wherein $R^6$, $R^7$, $R^8$, and $R^9$ have the same meanings as defined for formula (I) to afford a condensate and hydrolyzing said condensate as required.

Other objects, features and advantages of the invention will hereinafter become more readily apparent from the following description.

DETAILED DESCRIPTION OF THE INVENTION AND PREFERRED EMBODIMENTS

Both the compounds of formula (I) and their salts are novel compounds and exhibit a superior antibacterial activities against both gram positive and gram negative microorganisms. In particular, their antibacterial activities against gram positive microorganisms are remarkable. The compounds of formula (I) and their salts are therefore have a great value as antibacterial agents. They can be used not only as a medicine for man, animals, and fish, but also as an agrichemical and a food preservative.

According to the process of the present invention the compounds of formula (I) and their salts can be prepared very easily.

The compounds of the present invention have a general formula:

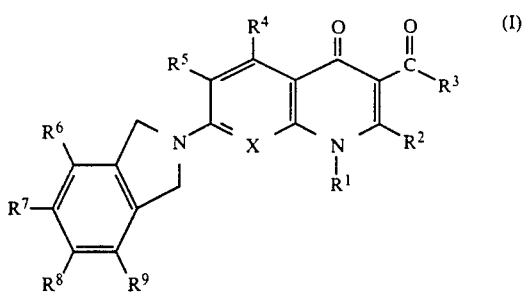

wherein $R^1$–$R^9$ and X have the meanings previously defined.

A lower alkyl group used in the present invention is defined as a linear or branched alkyl group having 1–5 carbon atoms; e.g. methyl, ethyl, n-butyl, and i-butyl groups. A lower alkyl group having a substituent includes, for example, amino-lower alkyl groups, mono-, di-, or trialkylamino lower alkyl groups, cyano-lower alkyl groups, hydroxy-lower alkyl groups, lower alkoxy-lower alkyl groups, carboxy-lower alkyl groups, lower alkoxycarbonyl-lower alkyl groups, halo-lower alkyl groups, lower alkylthio-lower alkyl groups, and the like.

An amino-lower alkyl group used in this invention is a lower alkyl group having one or more amino residues, e.g. aminomethyl group.

A mono-, di-, or tri-lower alkylamino lower alkyl group is a lower alkyl group having mono-, di-, or trilower alkylamino residues (these residues may be either the same or different), e.g. ethylaminomethyl, and dimethylaminomethyl, trimethylammonioethyl groups.

A cyano-lower alkyl group is a lower alkyl group having one or more cyano group residues, e.g. cyanomethyl group.

A hydroxy-lower alkyl group is a lower alkyl group having one or more hydroxy residues, e.g. hydroxymethyl and hydroxyethyl groups.

A lower alkoxy-lower alkyl group is a lower alkyl group having one or more lower alkoxy group residues (these alkoxy groups may be either the same or different), e.g. methoxymethyl group.

A carboxy-lower alkyl group is a lower alkyl group having one or more carboxy residues, e.g. carboxymethyl group.

A lower alkoxycarbonyl-lower alkyl group is a lower alkyl group having one or more lower alkoxycarbonyl group residues (these alkoxycarbonyl groups may be either the same or different), e.g. ethoxycarbonylmethyl group.

A halo-lower alkyl group is a lower alkyl group having one or more halogen atoms (these halogen atoms may be either the same or different), e.g. fluoromethyl, difluoromethyl, trifluoromethyl, 2-fluoroethyl, and 2,2,2-trifluoroethyl groups.

A lower alkylthio-lower alkyl group is a lower alkyl group having one or more alkylthio residues which may be either the same or different, e.g. methylthio-methyl group.

Halogen atoms used in this invention are fluorine, chlorine, bromine, and iodine atoms, with preferable halogen atoms being fluorine, chlorine, and bromine.

A cyclo-lower alkyl group is a cycloalkyl group having 3–7 carbon atoms, e.g. cyclopropyl, cyclobutyl, cyclopentyl, and cyclohexyl groups. Cyclopropyl group is a preferable cyclo-lower alkyl group.

A lower alkoxy group is a group represented by —O—Alk (Alk denotes a lower alkyl group), e.g. methoxy, ethoxy, propoxy, and t-butoxy groups.

A lower alkenyl group is an alkenyl group having 2–5 carbon atoms, e.g. vinyl, allyl, 1-propenyl, and 1-butenyl groups.

An aralkyl group which may have a substituent is defined as a lower alkyl group which may have one or more substituted aryl groups (these aryl groups may be either the same or different), e.g. benzyl group, 4-fluorobenzyl group, and phenethyl group.

A phenyl group which may have a substituent is defined as a phenyl group which may have one or more (same or different) substituted groups such as halogen atom, a lower alkyl group, a lower alkoxy group, a hydroxy group, an amino group, an amino-lower alkyl group, e.g. 4-fluorophenyl group, p-aminophenyl group, and 4-methylphenyl group.

An aryl group which may have a substituent is defined as an aryl group which may have one or more (same or different) substituted groups such as a halogen atom, a lower alkoxy group, a hydroxy group, an amino group, an amino-lower alkyl group. This group includes, beside the above-mentioned 4-methylphenyl, 4-fluorophenyl, and p-aminophenyl groups, for example, 7-hydroxy-2-naphthyl, 7-amino-2-naphthyl, and 7-fluoro-2-naphthyl groups.

An aroyl group which may have a substituent is a group represented by —CO—Ar (Ar denotes an aryl group which may have a substituent). Examples of this group are benzoyl, 4-methylbenzoyl, and 4-fluorobenzoyl groups.

A lower alkanoyloxy group is represented by —O—CO—Alk (Alk denotes a lower alkyl group) and includes, for example, acetoxy and propionyloxy groups.

A lower alkylthio group is represented by —S—Alk (Alk denotes a lower alkyl group) and includes, for example, methylthio and ethylthio groups.

A mono-, di-, or tri-lower alkylamino group is defined as an amino group which is substituted with 1, 2, or 3 alkyl groups (the alkyl groups may be the same or different). Examples are ethylamino, dimethylamino, and trimethylammonio groups.

A lower alkoxycarbonyl group is a group represented by —CO—O—Alk (Alk denotes a lower alkyl group) and includes, for example, methoxycarbonyl, and ethoxycarbonyl groups.

A mono- or di-lower alkylcarbamoyl group is defined as a carbamoyl group which is substituted with 1 or 2 lower alkyl groups (lower alkyl groups may be the same or different) A example is methylcarbamoyl group.

A lower arylcarbamoyl group which may have a substituent) is a group represented by —CONH—Ar (Ar denotes an aryl group which may have a substituent) and includes, for example, phenylcarbamoyl.

A lower alkanoyl group which may have a substituent is a group represented by —CO—Alk (Alk denotes a lower alkyl group which may be substituted with one or more halogen atoms, a lower alkoxy groups, phenyl groups, etc.). Examples of this group include acetyl, trifluoroacetyl, and propionyl groups.

An aroyloxy group which may have a substituent is a group represented by —OCO—Ar (Ar denotes an aryl group which may have a substituent), for example, benzoyloxy, 4-methylbenzoyloxy, 4-methoxybenzoyloxy, and 1-naphthoyloxy groups.

A halo-lower alkoxy group is a group represented by —O—HAlk (HAlk denotes a halo-lower alkyl group), for example, trifluoromethoxy and 2,2,2-trifluoroethoxy groups.

An aryloxy group which may have a substituent is a group represented by —O—Ar (Ar denotes an aryl group which may have a substituent), and includes, for example, phenoxy, 4-methylphenoxy, and 1-naphthyloxy groups.

A lower alkanoylamino group which may have a substituent is a group represented by —NH—Alkanoyl (Alkanoyl denotes a lower alkanoyl group), and includes, for example, acetylamino and propyonylamino groups.

An aroylamino group which may have a substituent is a group represented by —NH—Aro (Aro denotes an aroyl group which may have a substituent), and includes, for example, benzoylamino, 4-methoxybenzoylamino, and 1-naphthoylamino groups.

A lower alkoxycarbonylamino is a group represented by —NHCOO—Alk (Alk denotes a lower alkyl group). A typical example of this group is methoxycarbonylamino group.

A lower alkylsulfonyl group is represented by —SO$_2$—Alk (Alk denotes a lower alkyl group). A typical example of this group is methylsulfonyl group.

An arylsulfonyl group which may have a substituent is a group represented by —SO$_2$—Ar (Ar denotes an aryl group which may have a substituent), for example, phenylsulfonyl group.

A lower alkylsulfonamide group is represented by —SO$_2$NH—Alk (Alk denotes a lower alkyl group). A typical example of this group is methylsulfonamide group.

An arylsulfonamide group is represented by —SO$_2$NH—Ar (Ar denotes an aryl group which may have a substituent). Typical examples of this group are phenylsulfonamide and 4-methylphenylsulfonamide groups.

A heterocyclic group which may have a substituent is a heterocyclic group which may be substituted with one or more, the same or different kinds of groups, e.g. lower alkyl group, halogen atom, amino group, hydroxy group, lower alkoxy group, etc. Included in this group are, for example, furyl, thienyl, pyridyl, thiazolyl, imidazolyl, 1-methylimidazolyl groups.

A carboxy protective group used in this invention means any alcohol moiety of a carboxylic acid ester which is cleaved without difficulty to produce the corresponding free carboxyl group. Examples of such a group are those cleaved, such as methyl, ethyl, benzyl group, and trialkyl silyl groups which are decomposed by a mild treatment such as catalytic reduction or hydrolysis; and those easily decomposed in a living body, such as acetoxymethyl, pivaloyloxymethyl, ethoxycarbonyloxyethyl, dimethylaminoethyl, 1-piperidinylethyl, trimethylaminoethyl, phthalidyl, and the like.

The compounds of this invention may form both acid addition salts and base addition salts. Examples of acid addition salts are, for example, (a) salts of inorganic acid such as hydrochloric acid, sulfuric acid, or the like, (b) salts of organic carboxylic acid such as formic acid, citric acid, trichloroacetic acid, trifluoroacetic acid, or the like, and (c) salts of sulfonic acid such as methanesulfonic acid, benzenesulfonic acid, p-toluenesulfonic acid, mesitylenesulfonic acid, naphthalenesulfonic acid, or the like. Examples of base addition salts are (a) salts of alkali metal such as sodium, potassium, or the like, (b) salts of alkaline earth metal such as calcium, magnesium, or the like, (c) salts of ammonia, and (d) salts of nitrogen-containing organic base such as trimethylamine, triethylamine, tributylamine, pyridine, N,N-dimethylaniline, N-methylpyperidine, N-methylmorphorine, diethylamine, dicyclohexylamine, procaine, dibenzylamine, N-benzyl-β-phenetylamine, 1-ephenamine, N,N'-dibenzylethylenediamine, or the like.

The compounds of this invention can be present in any molecular form containing or not containing a solvent combined therein. In other words, they are capable of taking any crystalline forms containing or not containing molecules of a solvent including water. Accordingly, the present invention encompasses all of crystal forms and hydrates of such compounds.

Among various types of the compounds of this invention, preferable compounds are those isoindoline derivatives having a hydrogen atom for $R^2$ and a hydroxy group for $R^3$ in formula (I), including their salts. Another preferable types are those having =CY—(Y has the same meaning as previously defined) for X in formula (I), including their salts.

Specifically, the compounds of the present invention can be produced from any arbitrary combination of the quinoline derivatives listed in Table 1 and the isoindoline derivatives listed in Table 2 by condensation.

TABLE 1

| | $R_1$ | $R_2$ | $R_3$ | $R_4$ | $R_5$ | X |
|---|---|---|---|---|---|---|
| 1 |  | H | OH | H | F | C—H |
| 2 |  | H | OH | H | F | C—F |
| 3 |  | H | OH | H | F | C—Cl |
| 4 |  | H | OH | H | F | C—Br |
| 5 |  | H | OH | H | F | C—CH$_3$ |
| 6 |  | H | OH | H | F | C—OCH$_3$ |
| 7 | C$_2$H$_5$ | H | OH | H | F | C—H |
| 8 | C$_2$H$_5$ | H | OH | H | F | C—F |
| 9 | CH$_2$CH$_2$F | H | OH | H | F | C—H |
| 10 | CH$_2$CH$_2$F | H | OH | H | F | C—F |
| 11 | NCH$_3$ | H | OH | H | F | C—H |
| 12 | NCH$_3$ | H | OH | H | F | C—F |
| 13 | OCH$_3$ | H | OH | H | F | C—H |
| 14 | OCH$_3$ | H | OH | H | F | C—F |
| 15 | * | H | OH | H | F | 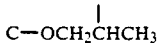 |
| 16 | * | H | OH | H | F | 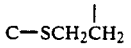 |
| 17 | * | H | OH | H | F | 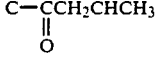 |
| 18 | * | H | OH | H | F | 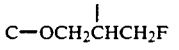 |
| 19 | * | H | OH | H | F | 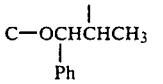 |
| 20 | *** | H | OH | H | F |  |
| 21 | * | H | OH | H | F | 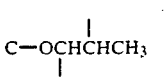 |

TABLE 1-continued

| | R₁ | R₂ | Formula (II) R₃ | R₄ | R₅ | X |
|---|---|---|---|---|---|---|
| 22 | *** | H | OH | H | F | C—OCH₂CH(OH)—CHCH₃ |
| 23 | * | H | OH | H | F | C—SCH₂CHCH₃ |
| 24 | * | H | OH | H | F | C—OCHCH₃ (with o-aminophenyl group, N) |
| 25 | cyclopropyl | H | OH | H | F | N |
| 26 | C₂H₅ | H | OH | H | F | N |
| 27 | 4-F-phenyl | H | OH | H | F | C—H |
| 28 | 4-F-phenyl | H | OH | H | F | C—F |
| 29 | 4-F-phenyl | H | OH | H | F | C—Cl |
| 30 | 3,4-di-F-phenyl | H | OH | H | F | C—H |
| 31 | 3,4-di-F-phenyl | H | OH | H | F | C—F |
| 32 | 4-OR'-phenyl | H | OH | H | F | C—H |
| 33 | 4-OR'-phenyl | H | OH | H | F | C—F |
| 34 | 4-NHR'-phenyl | H | OH | H | F | C—H |
| 35 | 4-NHR'-phenyl | H | OH | H | F | C—F |

TABLE 1-continued

Formula (II)

| | R₁ | R₂ | R₃ | R₄ | R₅ | X |
|---|---|---|---|---|---|---|
| 36 | phenyl(F, OR') | H | OH | H | F | C—H |
| 37 | phenyl(F, OR') | H | OH | H | F | C—F |
| 38 | phenyl(F, CH₂NHR') | H | OH | H | F | C—H |
| 39 | phenyl(F, CH₂NHR') | H | OH | H | F | C—F |
| 40 | phenyl(F) | H | OH | H | F | N |
| 41 | phenyl(F, F) | H | OH | H | F | N |
| 42 | phenyl(OR') | H | OH | H | F | N |
| 43 | phenyl(NHR') | H | OH | H | F | N |
| 44 | phenyl(F, OR') | H | OH | H | F | N |
| 45 | phenyl(F, CH₂NHR') | H | OH | H | F | N |
| 46 | cyclopropyl | H | OH | F | F | C—F |
| 47 | cyclopropyl | H | OH | NH₂ | F | C—F |
| 48 | cyclopropyl | H | OH | NHR¹ | F | C—F |
| 49 | cyclopropyl | H | OH | OH | F | C—F |
| 50 | cyclopropyl | H | OH | OCH₃ | F | C—F |

TABLE 1-continued
Formula (II)
| | $R_1$ | $R_2$ | $R_3$ | $R_4$ | $R_5$ | X |
|---|---|---|---|---|---|---|
| 51 |  | H | OH | $CH_3$ | F | C—H |
| 52 |  | H | OH | $CH_3$ | F | C—F |
| 53 | $-C_2H_5$ | H | OH | H | F | C—$CH_3$ |
| 54 |  | H | OH | F | F | C—$CH_3$ |
| 55 | $-C_2H_5$ | H | OH | H | F | C—$OCH_3$ |
| 56 |  | H | OH | F | F | C—$OCH_3$ |
| 57 |  | H | OH | $NH_2$ | F | C—$OCH_3$ |
| 58 |  | H | OH | H | Cl | C—Cl |
| 59 |  | H | OH | H | Cl | C—F |
| 60 |  | H | OH | H | Br | C—Cl |
| 61 |  | H | OH | Cl | Cl | C—Cl |
| 62 |  | H | OH | F | F | C—Cl |
| 63 |  | H | OH | H | $OCH_3$ | C—F |
| 64 |  | H | OH | F | $OCH_3$ | C—F |
| 65 |  | H | OH | F | F | C—F |
| 66 |  | H | OH | F | F | C—F |
| 67 |  | H | OH | F | F | C—F |
| 68 |  | H | OH | F | F | C—F |

TABLE 1-continued

| | R₁ | R₂ | R₃ | R₄ | R₅ | X |
|---|---|---|---|---|---|---|
| 69 | 4-fluorophenyl | H | OH | NH₂ | F | C—F |
| 70 | 3,4-difluorophenyl | H | OH | NH₂ | F | C—F |
| 71 | 4-fluorophenyl | H | OH | OH | F | C—F |
| 72 | 3,4-difluorophenyl | H | OH | OH | F | C—F |
| 73 | —CH₂-(4-fluorophenyl) | H | OH | H | F | C—H |
| 74 | —CH₂-(4-fluorophenyl) | H | OH | H | F | C—F |
| 75 | cyclopropyl | H | OH | F | F | N |
| 76 | cyclopropyl | H | OH | NH₂ | F | N |
| 77 | —CH=CH₂ | H | OH | H | F | C—H |
| 78 | —CH=CH₂ | H | OH | H | F | C—F |
| 79 | —CH=CH₂ | H | OH | F | F | C—F |
| 80 | —CH=CH₂ | H | OH | NH₂ | F | C—F |
| 81 | —CH=CH₂ | H | OH | H | F | N |
| 82 | * | H | OH | H | F | C—OCH=CH— |
| 83 | * | H | OH | H | F | C—OCH=C—CH₃ |
| 84 | * | H | OH | H | F | C—CH₂CH₂CHCH₃ |
| 85 | * | H | OH | H | F | C—CH=CHCHCH₃ |
| 86 | *** | H | OH | H | F | C—OCH₂CHCH—CH₃<br>NH₂ |
| 87 | * | H | OH | NH₂ | F | C—OCH₂CH—CH₃ |
| 88 | * | H | OH | F | F | C—OCH₂—CH—CH₃ |

TABLE 1-continued
| | R₁ | R₂ | Formula (II) R₃ | R₄ | R₅ | X |
|---|---|---|---|---|---|---|
| 89 | * | H | OH | OH | F | C—OCH₂CH(—CH₃)— |
| 90 |  | H | OH | NH₂ | F | C—Cl |
| 91 |  | H | OH | NH₂ | F | C—Br |
| 92 |  | H | OH | OH | F | C—Cl |
| 93 |  | H | OH | OH | F | C—Br |
| 94 |  | SCH₃ | OH | H | F | C—H |
| 95 |  | SCH₃ | OH | H | F | C—F |
| 96 |  | SCH₃ | OH | NH₂ | F | C—F |
| 97 |  | SCH₃ | OH | OH | F | C—F |
| 98 |  | ** | —NH—S— | H | F | C—H |
| 99 |  | ** | —NH—S— | H | F | C—F |
| 100 | C₂H₅ | ** | —NH—S— | H | F | C—F |
| 101 | 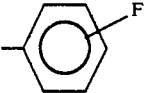 | ** | —NH—S— | H | F | C—F |
| 102 |  | ** | —NH—S— | NH₂ | F | C—F |
| 103 |  | ** | —NH—S— | OH | F | C—F |
| 104 |  | ** | —NH—S— | F | F | C—F |
| 105 | * | ** | —NH—S— | H | F | C—OCH₂CH(—CH₃)— |
| 106 | * | H | OH | H | F | C—O—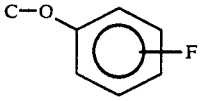—F |
| 107 | * | H | OH | H | F | C—N(CH₂CH(—CH₃))—R¹ |

TABLE 1-continued

Formula (II)

| | $R_1$ | $R_2$ | $R_3$ | $R_4$ | $R_5$ | X |
|---|---|---|---|---|---|---|
| 108 | * | ** | —NH—S— | H | F | C—O—C₆H₄—F (phenoxy with F) |
| 109 | cyclopropyl | H | OH | OCH₃ | F | C—Cl |
| 110 | cyclopropyl | H | OH | OCH₃ | F | C—Cl |
| 111 | cyclopropyl | H | OH | $NH_2$ | F | C—$CH_3$ |
| 112 | cyclopropyl | H | OH | OH | F | C—$CH_3$ |
| 113 | $CH_2CH_2F$ | H | OH | F | F | C—F |
| 114 | $CH_2CH_2F$ | H | OH | $NH_2$ | F | C—F |
| 115 | * | ** | —NH—S— | H | F | N |
| 116 | cyclopropyl | $SCH_3$ | OH | H | F | C—F |

*Form a six-membered ring together with X
**Form a five-membered ring together with $R^3$
R' hydrogen atom or lower alkyl group
***Form a seven-membered ring together with X

TABLE 2

Formula (III)

| | $R_6$ | $R_7$ | $R_8$ | $R_9$ |
|---|---|---|---|---|
| 1 | H | H | H | H |
| 2 | Hal | H | H | H |
|  | H | H | H | Hal |
| 3 | H | Hal | H | H |
|  | H | H | Hal | H |
| 4 | Hal | Hal | H | H |
|  | H | H | Hal | X |
| 5 | Hal | H | Hal | H |
|  | H | Hal | H | Hal |
| 6 | H | Hal | Hal | H |
| 7 | Hal | H | H | Hal |
| 8 | Hal | Hal | Hal | H |
|  | H | Hal | Hal | Hal |
| 9 | Hal | Hal | Hal | Hal |
| 10 | $NO_2$ | H | H | H |
|  | H | H | H | $NO_2$ |
| 11 | H | $NO_2$ | H | H |
|  | H | H | $NO_2$ | H |
| 12 | $NO_2$ | $NO_2$ | H | H |
|  | H | H | $NO_2$ | $NO_2$ |
| 13 | H | $NO_2$ | $NO_2$ | H |
| 14 | $NO_2$ | H | H | $NO_2$ |
| 15 | COOR' | H | H | H |
|  | H | H | H | COOR' |
| 16 | H | COOR' | H | H |
|  | H | H | COOR' | H |
| 17 | CN | H | H | H |
|  | H | H | H | CN |
| 18 | H | CN | H | H |
|  | H | H | CN | H |
| 19 | COR' | H | H | H |
|  | H | H | H | COR' |
| 20 | H | COR' | H | H |
|  | H | H | COR' | H |
| 21 | OPh | H | H | H |
|  | H | H | H | OPh |
| 22 | H | OPh | H | H |
|  | H | H | OPh | H |
| 23 | $SO_2R'$ | H | H | H |
|  | H | H | H | $SO_2R'$ |
| 24 | H | $SO_2R$ | H | H |
|  | H | H | $SO_2R$ | H |
| 25 | R | H | H | H |
|  | H | H | H | R |
| 26 | H | R | H | H |
|  | H | H | R | H |
| 27 | R | R | H | H |
|  | H | H | R | R |
| 28 | R | H | R | H |
|  | H | R | H | R |
| 29 | H | R | R | H |
| 30 | R | H | H | R |
| 31 | Ph | H | H | H |
|  | H | H | H | Ph |
| 32 | H | Ph | H | H |
|  | H | H | Ph | H |
| 33 | $CF_3$ | H | H | H |
|  | H | H | H | $CF_3$ |
| 34 | H | $CF_3$ | H | H |
|  | H | H | $CF_3$ | H |
| 35 | $CH_2NR'_2$ | H | H | H |
|  | H | H | H | $CH_2NR'_2$ |
| 36 | H | $CH_2NR'_2$ | H | H |
|  | H | H | $CH_2NR'_2$ | H |
| 37 | $CH_2OR'$ | H | H | H |
|  | H | H | H | $CH_2OR'$ |
| 38 | H | $CH_2OR'$ | H | H |
|  | H | H | $CH_2OR'$ | H |
| 39 | $CH_2CN$ | H | H | H |
|  | H | H | H | $CH_2CN$ |
| 40 | H | $CH_2CN$ | H | H |
|  | H | H | $CH_2CN$ | H |
| 41 | NHCOR' | H | H | H |
|  | H | H | H | NHCOR' |
| 42 | H | NHCOR' | H | H |
|  | H | H | NHCOR' | H |
| 43 | $OCF_3$ | H | H | H |
|  | H | H | H | $OCF_3$ |
| 44 | H | $OCF_3$ | H | H |
|  | H | H | $OCF_3$ | H |

TABLE 2-continued

| | Formula (III) | | | |
|---|---|---|---|---|
| | R6 | R7 | R8 | R9 |
| 45 | SR' | H | H | H |
| | H | H | H | SR' |
| 46 | H | SR' | H | H |
| | H | H | SR' | H |
| 47 | SCF3 | H | H | H |
| | H | H | H | SCF3 |
| 48 | H | SCF3 | H | H |
| | H | H | SCF3 | H |
| 49 | N+(CH3)3 | H | H | H |
| | H | H | H | N+(CH3)3 |
| 50 | H | N+(CH3)3 | H | H |
| | H | H | N+(CH3)3 | H |
| 51 | NR'2 | H | H | H |
| | H | H | H | NR'2 |
| 52 | H | NR'2 | H | H |
| | H | H | NR'2 | H |
| 53 | NR'2 | NR'2 | H | H |
| | H | H | NR'2 | NR'2 |
| 54 | NR'2 | H | NR2 | H |
| | H | NR'2 | H | NR'2 |
| 55 | NR'2 | H | H | NR'2 |
| 56 | H | NR'2 | NR'2 | H |
| 57 | OR' | H | H | H |
| | H | H | H | OR' |
| 58 | H | OR' | H | H |
| | H | H | OR' | H |
| 59 | OR' | OR' | H | H |
| | H | H | OR' | OR' |
| 60 | OR' | H | OR' | H |
| | H | OR' | H | OR' |
| 61 | OR' | H | H | OR' |
| 62 | H | OR' | OR' | H |
| 63 | NH2 | COOH | H | H |
| | H | H | COOH | NH2 |
| 64 | NH2 | H | COOH | H |
| | H | COOH | H | NH2 |
| 65 | H | NH2 | H | COOH |
| | COOH | H | NH2 | H |
| 66 | H | NH2 | COOH | H |
| 67 | CH2Ph | H | H | H |
| | H | H | H | CH2Ph |
| 68 | H | CH2Ph | H | H |
| | H | H | CH2Ph | H |
| 69 | COPh | H | H | H |
| | H | H | H | COPh |
| 70 | H | COPh | H | H |
| | H | H | COPh | H |
| 71 | NHCOPh | H | H | H |
| | H | H | H | NHCOPh |
| 72 | H | NHCOPh | H | H |
| | H | H | NHCOPh | H |
| 73 | NHCOPh | NHCOPh | H | H |
| | H | H | NHCOPh | NHCOPh |
| 74 | NHCOPh | H | NHCOPh | H |
| | H | NHCOPh | H | NHCOPh |
| 75 | H | NHCOPh | NHCOPh | H |
| 76 | NHCOPh | H | H | NHCOPh |
| 77 | OCOCH3 | H | H | H |
| | H | H | H | OCOCH3 |
| 78 | H | OCOCH3 | H | H |
| | H | H | OCOCH3 | H |
| 79 | OCOCH3 | OCOCH3 | H | H |
| | H | H | OCOCH3 | OCOCH3 |
| 80 | OCOCH3 | H | OCOCH3 | H |
| | H | OCOCH3 | H | OCOCH3 |
| 81 | OCOCH3 | H | H | OCOCH3 |
| 82 | H | OCOCH3 | OCOCH3 | H |
| 83 | OCOPh | H | H | H |
| | H | H | H | OCOPh |
| 84 | H | OCOPh | H | H |
| | H | H | OCOPh | H |
| 85 | CH2COOR' | H | H | H |
| | H | H | H | CH2COOR' |
| 86 | H | CH2COOR' | H | H |
| | H | H | CH2COOR' | H |
| 87 | SO2NHR' | H | H | H |
| | H | H | H | SO2NHR' |
| 88 | H | SO2NHR' | H | H |
| | H | H | SO2NHR' | H |
| 89 | SO2NHPh | H | H | H |
| | H | H | H | SO2NHPh |
| 90 | H | SO2NHPh | H | H |
| | H | H | SO2NHPh | H |
| 91 | 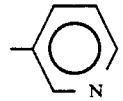 | H | H | H |
| | H | H | H |  |
| 92 | H |  | H | H |
| | H | H | 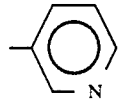 | H |
| 93 | 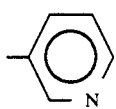 | H | H | H |
| | H | H | H |  |
| 94 | H |  | H | H |
| | H | H | 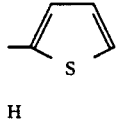 | H |
| 95 | 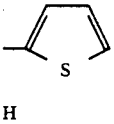 | H | H | H |
| | H | H | H |  |
| 96 | H | | H | H |
| | H | H | | H |
| 97 | Hal | NH2 | H | H |
| | H | H | NH2 | Hal |
| 98 | Hal | H | NH2 | H |
| | H | NH2 | H | Hal |

TABLE 2-continued

Formula (III)

| | R6 | R7 | R8 | R9 |
|---|---|---|---|---|
| 99 | Hal | H | H | NH2 |
| | NH2 | H | H | Hal |
| 100 | H | Hal | NH2 | H |
| | H | NH2 | Hal | H |
| 101 | Hal | OR' | H | H |
| | H | H | OR' | Hal |
| 102 | Hal | H | OR' | H |
| | H | OR' | H | Hal |
| 103 | Hal | H | H | OR' |
| | OR' | H | H | Hal |
| 104 | H | Hal | OR | H |
| | H | OR' | Hal | H |
| 105 | Hal | CH3 | H | H |
| | H | H | CH3 | Hal |
| 106 | Hal | H | CH3 | H |
| | H | CH3 | H | Hal |
| 107 | Hal | H | H | CH3 |
| | CH3 | H | H | Hal |
| 108 | H | Hal | CH3 | H |
| | H | CH3 | Hal | H |
| 109 | Hal | NHCOCH3 | H | H |
| | H | H | NHCOCH3 | Hal |
| 110 | Hal | H | NHCOCH3 | H |
| | H | NHCOCH3 | H | Hal |
| 111 | Hal | H | H | NHCOCH3 |
| | NHCOCH3 | H | H | Hal |
| 112 | H | Hal | NHCOCH3 | H |
| | H | NHCOCH3 | Hal | H |
| 113 | Hal | NO2 | H | H |
| | H | H | NO2 | Hal |
| 114 | Hal | H | NO2 | H |
| | H | NO2 | H | Hal |
| 115 | Hal | H | H | NO2 |
| | NO2 | H | H | Hal |
| 116 | H | Hal | NO2 | H |
| | H | NO2 | Hal | H |
| 117 | CH3 | NH2 | H | H |
| | H | H | NH2 | CH3 |
| 118 | H | CH3 | NH2 | H |
| | H | NH2 | CH3 | H |
| 119 | CH3 | H | NH2 | H |
| | H | NH2 | H | CH3 |
| 120 | CH3 | H | H | NH2 |
| | NH2 | H | H | CH3 |

Remarks for Table 2
Hal: represents a halogen atom selected from F, Cl, Br, or I.
R: represents a lower alkyl group.
R': represents a hydrogen atom or a lower alkyl group.
Ph: represents a phenyl group which may have a substituents.

Presented below are chemical structures of quinoline derivatives Nos. 15, 83, 99, and 106 listed in Table 1. These are the examples of quinoline derivatives in which $R^1$ and X or $R^2$ and $R^3$ form a ring in conjunction with each other.

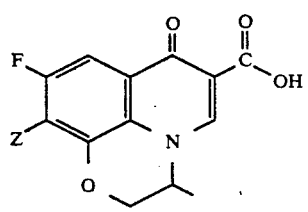

No. 15

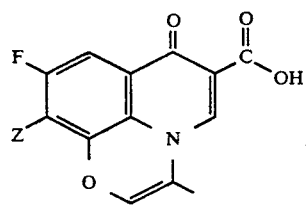

No. 83

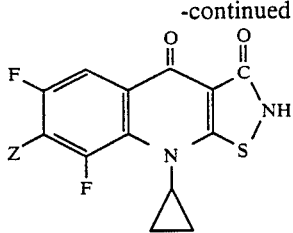

No. 99

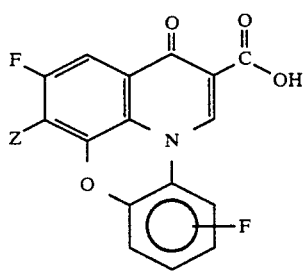

No. 106

In the preparation of the compounds of this invention, any appropriate methods can be used in forming chemical bonds in the compounds or in forming or introducing various substituents. A typical method comprises reacting a compound represented by the formula (II):

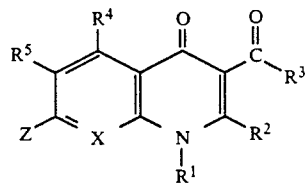

(II)

wherein $R^1$, $R^2$, $R^3$, $R^4$, $R^5$, and X have the same meanings as previously defined and Z represents a reactive leaving group, with a compound represented by the formula (III):

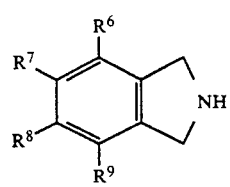

(III)

wherein $R^6$, $R^7$, $R^8$, and $R^9$ have the same meanings as previously defined to give a condensate and, if required, hydrolysis of said condensate.

Examples of the reactive leaving group represented by Z in formula (II) are halogen atoms, e.g. fluorine and chlorine, arylsulfonyl groups, e.g. phenylsulfonyl group, arylsulfonyloxy groups, e.g. phenylsulfonyloxy group, and the like.

The reaction is carried out in an inert solvent such as an aromatic hydrocarbon, e.g. benzene, toluene, xylene, etc., an alcohol, e.g. methanol, ethanol, etc., tetrahydrofuran, acetonitrile, pyridine, dimethylformamide, dimethylsulfoxide, N-methylpyrrolidone, or the like, at 20°–160° C. The reaction may be conducted in the presence of an acid-neutralizing agent such as sodium carbonate, calcium carbonate, sodium bicarbonate, triethylamine, 1,8-diazabicyclo[5,4,0]-7-undecene (DBU) or the like, at 20°-160° C. Under these conditions compounds of formulae (II) and (III) are reacted for several minutes to several days, preferably for 10 minutes to 24 hours.

When the starting compound of formula (III) contains an amino group which does not precipitate in the condensation reaction, such an amino group can be protected in advance. The protective group used can be removed by using a conventional method after the reaction. Any protective groups may be used for this purpose so far as the protective group can be removed after the reaction without decomposition of the target molecules. Such groups include those groups conventionally used in the chemistry of peptides, amino saccharides, nucleic acids, and the like.

The starting compounds (II) can be produced by any methods described in the following literatures, or the methods analogous or conforming to these methods.
1) J. Med. Chem., 23, 1358 (1980)
2) J. Med. Chem., 27, 1103 (1984)
3) J. Med. Chem., 28, 1558 (1985)
4) J. Med. Chem., 30, 504 (1987)
5) J. Med. Chem., 29, 2363 (1986)
6) J. Pharmacopeia, Jpn. 106, 802 (1986)
7) J. Pharmacopeia, Jpn. 106, 795 (1986)
8) J. Med. Chem., 30, 465 (1987)
9) J. Med. Chem., 29, 1531 (1986)
10) Chem. Pharm. Bull. Jpn. 34, 4098 (1986)
11) J. Med. Chem., 27, 292 (1984)
12) J. Med. Chem., 31, 503 (1988)
13) Japanese Patent Laid-open No. 47658/1980
14) Japanese Patent Laid-open No. 157068/1984
15) Japanese Patent Laid-open No. 212474/1984
16) Japanese Patent Laid-open No. 72885/1985
17) Japanese Patent Laid-open No. 260577/1985
18) Japanese Patent Laid-open No. 469/1987
19) Japanese Patent Laid-open No. 490/1987
20) Japanese Patent Laid-open No. 26272/1987
21) Japanese Patent Laid-open No. 59263/1987
22) Japanese Patent Laid-open No. 53987/1987
23) Japanese Patent Laid-open No. 84085/1987
24) Japanese Patent Laid-open No. 155282/1987
25) Japanese Patent Laid-open No. 167768/1987
26) Japanese Patent Laid-open No. 174054/1987
27) Japanese Patent Laid-open No. 175482/1987
28) Japanese Patent Laid-open No. 175484/1987
29) Japanese Patent Laid-open No. 175485/1987
30) Japanese Patent Laid-open No. 187472/1987
31) Japanese Patent Laid-open No. 187459/1987
32) Japanese Patent Laid-open No. 201869/1987
33) Japanese Patent Laid-open No. 205060/1987
34) Japanese Patent Laid-open No. 215572/1987
35) Japanese Patent Laid-open No. 226962/1987
36) Japanese Patent Laid-open No. 228063/1987
37) Japanese Patent Laid-open No. 39880/1988
38) Japanese Patent Laid-open No. 60990/1988

The compound having a hydrogen atom for $R^6$, $R^7$, $R^8$, and $R^9$ of formula (III) is a known compound and can be prepared according to the method described in Organic Synthesis Collective, 5, 1064 and 406. Other compounds of formula (III) can be prepared according to this method or the methods presented in Reference Examples hereinafter described.

When the compound prepared by the methods described above is an ester such a compound can be converted by a commonly well known method, for example, by hydrolysis using an acid or alkali or by reduction using hydrogen, into a compound having a hydroxy group for $R^3$ in formula (I). A compound having a hydroxy group for $R^3$ in formula (I), if necessary, can be converted into an ester using a conventional method. The compound of this invention thus prepared can be isolated and purified according to conventional methods. Depending on the conditions employed in the isolation and purification steps, the product may be obtained either as a salt, a free carboxylic acid, or a free amine. If necessary, these are converted into the another desired form, e.g. into a salt, a free carboxylic acid, or a free amine.

Other features of the invention will become apparent in the course of the following description of the exemplary embodiments which are given for illustration of the invention and are not intended to be limiting thereof.

In the examples the designation "ARM" for NMR spectrum absorption band represents "Aromatic band".

EXAMPLES

Example 1

7-(2-isoindolinyl-1-cyclopropyl-6,8-difluoro-1,4-dihydro-4-oxoquinoline-3-carboxylic acid

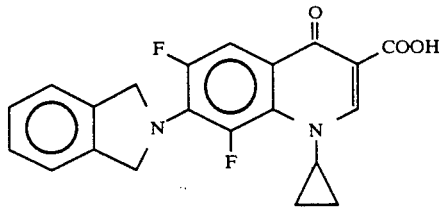

A mixture of 136 mg of 1-cyclopropyl-6,7,8-trifluoro-1,4-dihydro-4-oxoquinoline-3-carboxylic acid, 180 mg of isoindoline, and 1.5 ml of anhydrous DMF was heated at 120° C. for 1.5 hours while stirring. The resulting reaction mixture was evaporated under reduced pressure to dryness. The residue thus obtained was dissolved into 20 ml of chloroform. The solution was washed with 5% acetic acid and brine in this order, dried over anhydrous sodium sulfate, and condensed. The residue was crystallized by the addition of hot ethanol. After cooling the mixture, the crystals were collected by filtration and recrystallized from a mixed solvent of chloroform, methanol, and ethanol to obtain 123 mg of the target compound.

Melting point: 265°-269° C. (decomposed)

$^1$H-NMR (CMSO-d$_6$) δ: 8.67 (1H, s, C$_2$—H), 7.80 (1H, d, J=13Hz, C$_5$—H ), 7.25-7.50 (4H, m, AR-M—H), 5.18 (4H, s, 2 x—$\underline{CH_2}$N—), 4.08-4.25 (1H. m,

), 1.12-1.30 (4H, m,

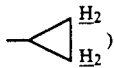)

Example 2

7-(4-amino-2-isoindolinyl)-1-cyclopropyl-6,8-difluoro-1,4-dihydro-4-oxoquinoline-3-carboxylic acid

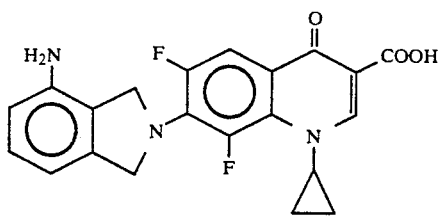

A mixture of 136 mg of 1-cyclopropyl-6,7,8-trifluoro-1,4-dihydro-4-oxoquinoline-3-carboxylic acid, 180 mg of 4-aminoisoindoline, and 1.5 ml of anhydrous DMF was heated at 120° C. for 1.5 hours while stirring. The resulting reaction mixture was evaporated under reduced pressure to dryness. 20 ml of chloroform and 10 ml of 5% acetic acid was added to the residue, and the mixture was stirred. Deposited crystals were collected by filtration, washed with water and ethanol. The chloroform layer was separated, washed with brine, dried over anhydrous sodium sulfate, and condensed. The residue was crystallized by the addition of hot ethanol. After cooling the mixture, the crystals were collected by filtration. These crystals were combined with those collected above and were recrystallized from a mixed solvent of chloroform, methanol, and ethanol to obtain 123 mg of the target compound.

Melting Point: 261°–264° C. (decomposed)

$^1$H-NMR (DMSO-d$_6$) δ: 8.63 (1H, s, C$_2$—H), 7.75 (1H, d, J=14Hz, C$_5$—H), 6.50–7.05 (3H, m, ARM—H), 4.95–5.20 (6H, m, 2x —C$\underline{H}_2$—N—, —N$\underline{H}_2$), 4.05–4.17 (1H, m,

), 1.10–1.30 (4H, m,

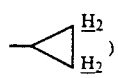)

Example 3

7-(5-amino-2-isoindolinyl)-1-cyclopropyl-6,8-difluoro-1,4-dihydro-4-oxoquinoline-3-carboxylic acid.

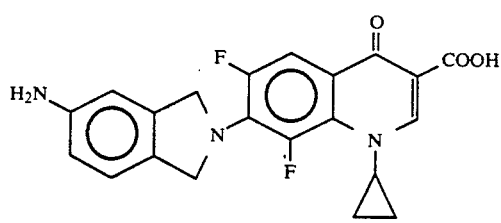

136 mg of 1-cyclopropyl-6,7,8-trifluoro-1,4-dihydro-4-oxoquinoline-3-carboxylic acid, 200 mg of isoindoline, and 1.5 ml of anhydrous DMF were processed in the same manner as in Example 2 to produce 130 mg of the target compound.

Melting Point: 266°–268° C. (decomposed)

$^1$H-NMR (DMSO-d$_6$) δ:8.65 (1H, s, C$_2$—H), 7.78 (1H, d, J=13Hz, C$_5$—H), 6.50–7.06 (3H, m, ARM—H), 4.95–5.15 (4H, m, 2 x —NC$\underline{H}_2$—), 4.05–4.20 (1H, m,

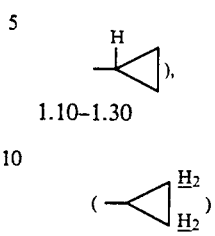), 1.10–1.30

(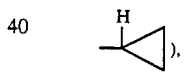)

Example 4

7-(4-methoxy-2-isoindolinyl)-1-cyclopropyl-6,8-difluoro-1,4-dihydro-4-oxoquinoline-3-carboxylic acid

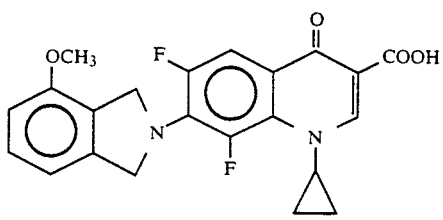

136 mg of 1-cyclopropyl-6,7,8-trifluoro-1,4-dihydro-4-oxoquinoline-3-carboxylic acid, 224 mg of 4-methoxyisoindoline, and 1.5 ml of anhydrous DMF were processed in the same manner as in Example 2 to produce 132 mg of the target compound.

Melting Point: 279°–281° C. (decomposed)

$^1$H-NMR (DMSO-d$_6$) δ:8.69 (1H, s, C$_2$—H), 7.80 (1H, d, J=14Hz, C$_5$—H), 6.95–7.36 (3H, m, ARM—H), 5.05–5.25 (4H, m, 2 x —C$\underline{H}_2$—N—), 4.10–4.20 (1H, m,

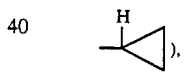), 3.85 (3H, s, —OC$\underline{H}_3$), 1.15–1.25 (4H, m,

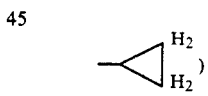)

Example 5

7-(5-ethylamino-2-isoindolinyl)-1-cyclopropyl-6,8-difluoro-1,4-dihydro-4-oxoquinoline-3-carboxylic acid

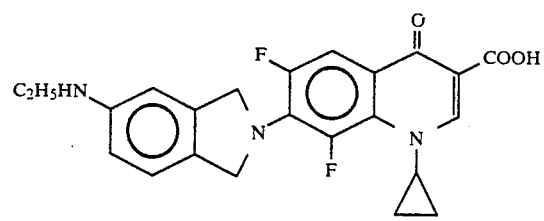

141 mg of 1-cyclopropyl-6,7,8-trifluoro-1,4-dihydro-4-oxoquinoline-3-carboxylic acid, 253 mg of 5-ethylaminoisoindoline, and 1.5 ml of anhydrous DMF were processed in the same manner as in Example 2 to produce 128 mg of the target compound.

Melting Point: 244°-247° C. (decomposed) ¹H-NMR (CDCl₃) δ:8.78 (1H, s, C₂—H), 7.90 (1H, d, J=14H$_Z$, C₅—H), 6.50-7.15 (3H, m, ARM—H), 5.10-5.20 (4H, m, 2 x —C$\underline{H}$₂N—), 3.90-4.10 (1H, m,

), 3.10 (2H, q, J=7H$_Z$, —C$\underline{H}$₂CH₃), 1.30 (3H, t, J=7H$_Z$, —CH₂C$\underline{H}$₃), 1.10-1.20 (4H, m,

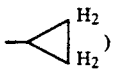)

Example 6

7-(4-hydroxy-2-isoindolinyl)-1-cyclopropyl-6,8-difluoro-1,4-dihydro-4-oxoquinoline-3-carboxylic acid

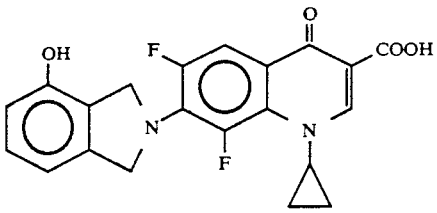

136 mg of 1-cyclopropyl-6,7,8-trifluoro-1,4-dihydro-4-oxoquinoline-3-carboxylic acid, 130 mg of 4-hydroxyisoindoline hydrobromide, 114 mg of 1,8-diazabicyclo[5,4,0]-7-undecene (DBU), and 1.5 ml of anhydrous DMF were processed in the same manner as in Example 1 to produce 37 mg of the target compound.

Melting Point: above 300° C.

¹H-NMR (DMSO-d₆) δ:8.65 (1H, s, C₂—H), 7.88 (1H, d, J=14H$_Z$, C₅—H), 6.70-7.20 (3H, m, ARM—H), 5.02-5.20 (4H, m, 2 x —C$\underline{H}$₂N—), 4.08-4.20 (1H, m,

), 1.05-1.25 (4H, m,

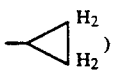)

Example 7

10-(2-isoindolinyl)-9-fluoro-2,3-dihydro-3-methyl-7-oxo-7H-pyrido[1,2,3-de][1,4]-benzoxazine-6-carboxylic acid

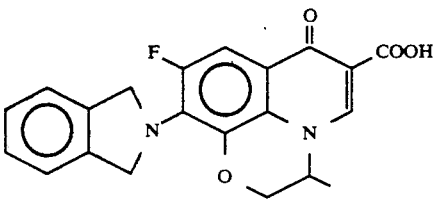

157 mg of 9,10-difluoro-2,3-dihydro-3-methyl-7-oxo-7H-pyrido[1,2,3-de]1,4]-benzoxazine-6-carboxylic acid, 215 mg of isoindoline, and anhydrous DMF were processed in the same manner as in Example 2 to produce 104 mg of the target compound.

Melting Point: above 300° C.

¹H-NMR (DMSO-d₆) δ:8.95 (1H, s, C₅—H), 7.62 (1H, d, J=13H$_Z$, C₈—H), 7.20-7.45 (4H, m, ARM—H), 4.98-5.20 (4H, m, —C$\underline{H}$₂N—), 4.30-4.97 (3H, m, C₂—H, C₃—H), 1.50 (3H, d, J=7H$_Z$, CH₃)

Example 8

10-(4-amino-2-isoindolinyl)-9-fluoro-2,3-dihydro-3-methyl-7-oxo-7H-pyrido[1,2,3-de][1,4]-benzoxazine-6-carboxylic acid

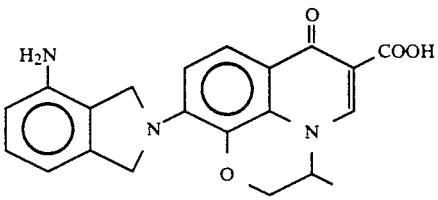

157 mg of 9,10-difluoro-2,3-dihydro-3-methyl-7-oxo-7H-pyrido[1,2,3-de][1,4]-benzoxazine-6-carboxylic acid, 242 mg of 4-aminoisoindoline, and 1.5 ml of anhydrous DMF were processed in the same manner as in Example 2 to produce 119 mg of the target compound.

Melting Point: above 244°247° C. (decomposed)

¹H-NMR (DMSO-d₆) δ:8.98 (1H, s, C₅—H), 7.65 (1H, d, J=13H$_Z$, C₈—H), 6.45-7.10 (3H, m, ARM-H), 4.99-5.20 (4H, m, 2 x —NC$\underline{H}$₂—), 4.30-4.95 (3H, m, C₂—H, C₃—H), 1.50 (3H, d, J=7H, CH₃)

Example 9

10-(5-amino-2-isoindolinyl)-9-fluoro-2,3-dihydro-3-methyl-7-oxo-7H-pyrido[1,2,3-de][1,4]-benzoxazine-6-carboxylic acid

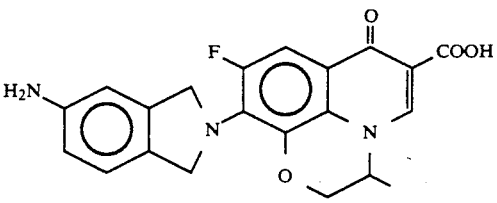

157 mg of 9,10-difluoro-2,3-dihydro-3-methyl-7-oxo-7H-pyrido[1,2,3-de][1,4]-benzoxazine-6-carboxylic acid, 242 mg of 5-aminoisoindoline, and 1.5 ml of anhydrous DMF were processed in the same manner as in Example 2 to produce 124 mg of the target compound.

Melting Point: 272°-276° C.

¹H-NMR (DMSO-d₆) δ:8.90 (1H, s, C₅—H), 7.58 (1H, d, J=14H$_Z$, C₈—H), 6.45-7.02 (3H, m, ARM-H), 4.80-5.20 (4H, m, 2 x —NC$\underline{H}$₂—,C₃—H), 4.25-4.65 (2H, m, C₂—H), 1.46 (3H, d, J=7H$_Z$, CH₃)

Example 10

10-(4-methoxy-2-isoindolinyl)-9-fluoro-2,3-dihydro-3-methyl-7-oxo-7H-pyrido[1,2,3-de][1,4]-benzoxazine-6-carboxylic acid

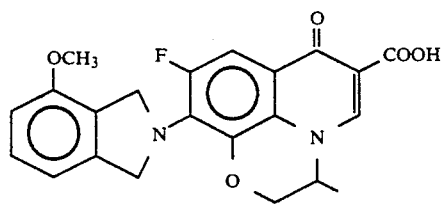

131 mg of 9,10-difluoro-2,3-dihydro-3-methyl-7-oxo-7H-pyrido[1,2,3-de][1,4]-benzoxazine-6-carboxylic acid, 224 mg of 4-methoxyisoindoline, and 1.5 ml of anhydrous DMF were processed in the same manner as in Example 2 to produce 99 mg of the target compound.

Melting Point: 262°–264° C.

$^1$H-NMR (DMSO-d$_6$) δ:8.95 (1H, s, C$_5$—H), 7.64 (1H, d, J=13Hz, C$_8$—H), 6.90–7.36 (3H, m, ARM-H), 4.95–5.20 (4H, m, 2 x —CH$_2$N—), 4.30–4.95 (3H, m, C$_2$—H, C$_3$—H), 3.82 (3H, s, OCH$_3$), 1.50 (3H, d, J=7Hz, CH$_3$)

Example 11

10-(5-ethylamino-2-isoindolinyl)-9-fluoro-2,3-dihydro-3-methyl-7-oxo-7H-pyrido [1,2,3-de][1,4]-benzoxazine-6-carboxylic acid

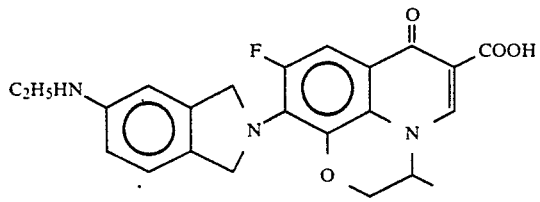

141 mg of 9,10-difluoro-2,3-dihydro-3-methyl-7-oxo-7H-pyrido [1,2,3-de][1,4]-benzoxazine-6-carboxylic acid, 97 mg of 5-ethylaminoisoindoline, 152 mg of DBU, and 1.5 ml of anhydrous DMF were processed in the same manner as in Example 1 to produce 109 mg of the target compound.

Melting Point: above 300° C.

$^1$H-NMR (DMSO-d$_6$) δ:8.95 (1H, s, C$_5$—H), 7.62 (1H, d, J=13Hz, C$_8$—H), 6.50–7.10 (3H, m, ARM-H), 4.80–5.10 (4H, m, 2 x —CH$_2$N—), 4.35 and 4.60 (each 1H, ABq, C$_2$—H), 3.05 (2H, q, J=7Hz, —CH$_2$CH$_3$), 1.50 (3H, d, J=7Hz, C$_2$-CH$_3$), 1.17 (3H, t, J=7Hz, —CH$_2$CH$_3$)

Example 12

7-(2-isoindolinyl)-1-ethyl-6-fluoro-1,4-dihydro-4-oxoquinoline-3-carboxylic acid

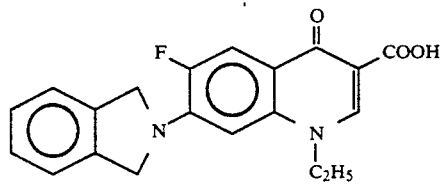

177 mg of 1-ethyl-6,7-difluoro-1,4-dihydro-4-oxoquinoline-3-carboxylic acid, 250 mg of isoindoline, and 1.5 ml of anhydrous DMF were processed in the same manner as in Example 2 to produce 110 mg of the target compound.

Melting Point: above 300° C.

Example 13

7-(4-amino-2-isoindolinyl)-1-ethyl-6-fluoro-1 4-dihydro-4-oxoquinoline-3-carboxylic acid

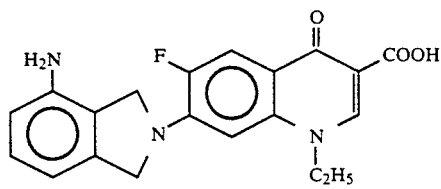

177 mg of 1-ethyl-6,7-difluoro-1,4-dihydro-4-oxoquinoline-3-carboxylic acid, 282 mg of 4-aminoisoindoline, and 1.5 ml of anhydrous DMF were processed in the same manner as in Example 2 to produce 141 mg of the target compound.

Melting Point: above 300° C.

Example 14

7-(5-amino-2-isoindolinyl)-1-ethyl-6-fluoro-1,4-dihydro-4-oxoquinoline-3-carboxylic acid

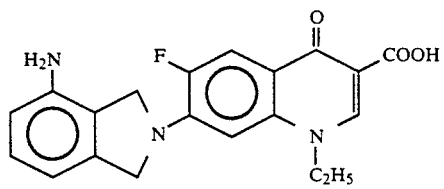

177 mg of 1-ethyl-6,7-difluoro-1,4-dihydro-4-oxoquinoline-3-carboxylic acid, 113 mg of 5-aminoisoindoline, 213 mg of DBU, and 1.5 ml of anhydrous DMF were processed in the same manner as in Example 2 to produce 63 mg of the target compound.

Melting Point: above 300° C.

$^1$H-NMR (DMSO-d$_6$δ:8.90 (1H, s, C$_2$—H), 7.90 (1H, d, J=14Hz, C$_5$—H), 6.75–7.50 (4H, m, C$_8$—H, ARM-H), 4.90–5.15 (4H, m, 2 x —CH$_2$N—), 4.58 (2H, q, J=7Hz, —CH$_2$CH$_3$), 1.45 (3H, t, J=7Hz, —CH$_2$CH$_3$)

Example 15

7-(5-ethylamino-2-isoindolinyl)-1-ethyl-6-fluoro-1,4-dihydro-4-oxoquinoline-3-carboxylic acid 177 mg of 1-ethyl-6,7-difluoro-1,4-dihydro-4-oxoquinoline-3-carboxylic acid, 136 mg of 5-ethylaminoisoindoline, 213 mg of DBU, and 1.5 ml of anhydrous DMF were processed in the same manner as in Example 1 to produce 138 mg of the target compound.

Melting Point: 246°–248° C.

Example 16

7-(2-isoindolinyl)-1-cyclopropyl-6-fluoro-1,4-dihydro-4-oxoquinoline-3-carboxylic acid

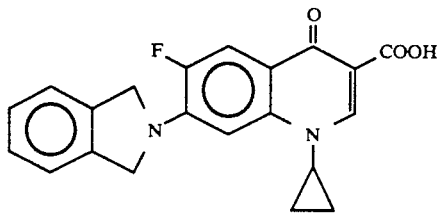

133 mg of 1-cyclopropyl-6,7-difluoro-1,4-dihydro-4-oxoquinoline-3-carboxylic acid, 83 mg of isoindoline, 152 mg of DBU, and 1.5 ml of anhydrous DMF were processed in the same manner as in Example 1 to produce 65 mg of the target compound.

Melting Point: above 262°–267° C. (decomposed)

$^1$H-NMR (DMSO-d$_6$) δ:8.63 (1H, s, C$_2$—H), 7.90 (1H, d, J=14H$_Z$, C$_5$—H), 7.20–7.50 (5H, C$_8$—H, ARM-H), 5.10 (4H, s, 2 x —CH$_2$N—), 3.80 (1H, m,

), 1.15–1.45 (4H, m,

)

Example 17

7-(4-amino-2-isoindolinyl)-1-cyclopropyl-6-fluoro-1,4-dihydro-4-oxoquinoline-3-carboxylic acid

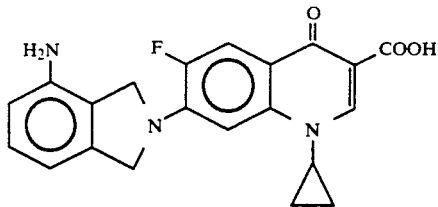

133 mg of 1-cyclopropyl-6,7-difluoro-1,4-dihydro-4-oxoquinoline-3-carboxylic acid, 81 mg of 4-aminoisoindoline, 182 mg of DBU, and 1.5 ml of anhydrous DMF were processed in the same manner as in Example 2 to produce 97 mg of the target compound.

Melting Point: 240°–244° C. (decomposed)

$^1$H-NMR (DMSO-d$_6$) δ:8.60 (1H, s, c$_2$—H), 7.86 (1H, d, J=14H$_Z$, C$_5$—H), 6.50–7.30 (4H, m, C$_8$—H, ARM-H), 4.70–5.10 (4H, m, 2 x —CH$_2$—N—), 3.80 (1H, m,

), 1.10–1.50 (4H, m,

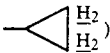)

Example 18

7-(2-isoindolinyl)-1-cyclopropyl-5-amino-6,8-difluoro-1,4-dihydro-4-oxoquinoline-3-carboxylic acid

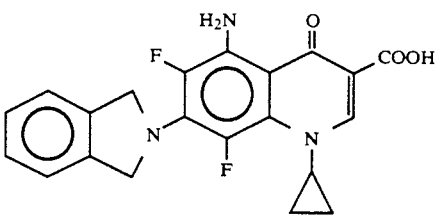

A mixture of 200 mg of 1-cyclopropyl-5-amino-6,7,8-trifluoro-1,4-dihydro-4-oxoquinoline-3-carboxylic acid, 87 mg of isoindoline, 200 mg of DBU, and 1.5 ml of anhydrous DMF was heated at 110°–115° C. for 20 minutes while stirring. After cooling, 30 ml of chloroform and 10 ml of 5% acetic acid were added to the resulting reaction mixture. The mixture was thoroughly stirred and the organic layer was separated. The water layer was extracted once more with 20 ml of chloroform. The extract, mixed with the organic layer, was dried over magnesium sulfate, and condensed. The residue was recrystallized from a mixed solvent of chloroform and methanol to obtain 144 mg of the target compound.

Melting Point: 263°–266° C. (decomposed) $^1$H-NMR (CDCl$_3$—CF$_3$COOD, 10:1) δ:8.90 (1H, s, C$_2$—H), 7.25–7.45 (4H, m, ARM-H), 5.33 (4H, s, 2 x —CH$_2$N—), 4.20 (1H, m,

), 1.15–1.45 (4H, m,

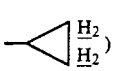)

Example 19

7-(2-isoindolinyl)-1-cyclopropyl-5,6,8-trifluoro-1 4-dihydro-4-oxoquinoline-3-carboxylic acid

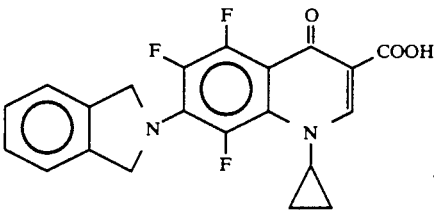

200 mg of 1-cyclopropyl-5,6,7,8-tetrafluoro-1,4-dihydro- 4-oxoquinoline-3-carboxylic acid, 87 mg of isoindoline, 200 mg of DBU, and 1.5 ml of anhydrous DMF were processed in the same manner as in Example 18 to produce 82 mg of the target compound.

Melting Point: 268°–273° C. (decomposed)

¹H-NMR (CDCl₃—CF₄COOD 10:1) δ:9.04 (1H, s, C₂—H), 7.30–7.45 (4H, m, ARM-H), 5.35–5.52 (4H, m, 2 x —CH₂N—), 4.23–4.38 (1H, m,

), 1.20–1.53 (4H, m,

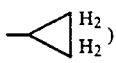)

Example 20

7-(5-chloro-2-isoindolinyl)-1-cyclopropyl-6-fluoro-1,4-dihydro-4-oxoquinoline-3-carboxylic acid

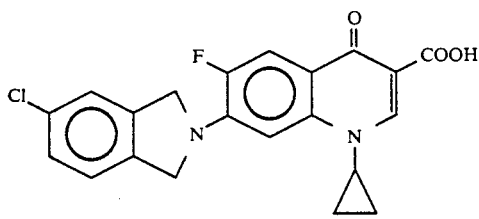

A mixture of 136 mg of 1-cyclopropyl-6,7-difluoro-1,4-dihydro-4-oxoquinoline-3-carboxylic acid, 123 mg of 5-chloroisoindoline, 122 mg of DBU, and 1.5 ml of anhydrous DMF was heated at 110° C. for 1.5 hours while stirring. The resulting reaction mixture was evaporated under reduced pressure to dryness. 20 ml of chloroform and 10 ml of 5% acetic acid were added to the residue thus obtained, and the mixture was stirred. The deposited crystals were collected by filtration and washed with water and then ethanol. The chloroform layer was separated, and washed with water, dried over anhydrous sodium sulfate, and condensed. The residue was crystallized by the addition of hot ethanol. After cooling the mixture, the crystals were collected by filtration. These crystals, combined with the crystals obtained above, were recrystallized from a mixed solvent of chloroform, methanol, and ethanol to obtain 128 mg of the target compound.

Melting Point: 278°–282° C. (decomposed)

¹H-NMR (DMSO-d₆) δ:8.60 (1H, s, C₂—H), 7.86 (1H, d, J=15Hz, C₅—H), 7.35–7.60 (3H, m, ARM-H), 7.20 (1H, d, J=8Hz, C₈—H), 4.90–5.10 (4H, m, 2 x —CH₂N—), 3.78 (1H, m,

), 1.10–1.40 (4H, m,

)

Example 21

7-(4-fluoro-2-isoindolinyl)-1-cyclopropyl-6-fluoro 1,4-dihydro-4-oxoquinoline-3-carboxylic acid

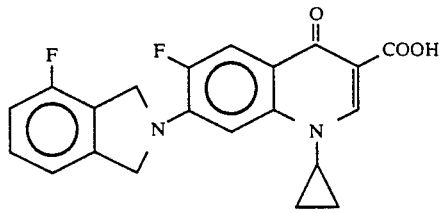

A mixture of 136 mg of 1-cyclopropyl-6,7-difluoro-1,4-dihydro-4-oxoquinoline-3-carboxylic acid, 206 mg of 4-fluoroisoindoline, and 1.5 ml of anhydrous DMF was heated at 110° C. for 1.5 hours while stirring. The resulting reaction mixture was evaporated under reduced pressure to dryness. 20 ml of chloroform and 10 ml of 5% acetic acid were added to the residue thus obtained, and the mixture was stirred. The deposited crystals were collected by filtration and washed with water and then ethanol. The chloroform layer was separated, washed with water, dried over anhydrous sodium sulfate, and condensed. The residue was crystallized by the addition of hot ethanol. After cooling the mixture, the crystals were collected by filtration. These crystals, combined with the crystals obtained above, were recrystallized from a mixed solvent of chloroform, methanol, and ethanol to obtain 85 mg of the target compound.

Melting Point: 294°–299° C. (decomposed)

¹H-NMR (DMSO-d₆) δ:8.65 (1H s, C₂—H) 7.94 1H, d,

J=14Hz, C₅—H), 7.20–7.50 (4H, m, C₈—H, ARM-H), 5.15 (4H, brs, 2 x —CH₂N—), 3.85 (1H, m,

), 1.15–1.45 (4H, m,

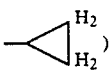)

Example 22

10-(4-fluoro-2-isoindolinyl)-9-fluoro-2,3-dihydro-3-methyl-7-oxo-7H-pyrido[1,2,3-de][1,4]-benzoxazine-6-carboxylic acid

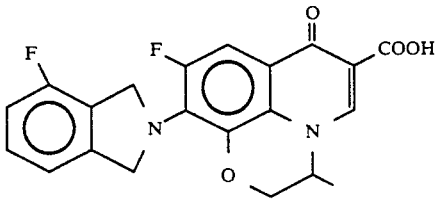

141 mg of 9,10-difluoro-2,3-dihydro-3-methyl-7-oxo-7H-pyrido[1,2,3-de][1,4]-benzoxazine-6-carboxylic acid, 206 mg of 4-fluoroisoindoline, and 1.5 ml of anhydrous DMF were processed in the same manner as in Example 20 to produce 71 mg of the target compound.

Melting Point: above 300° C.

$^1$H-NMR (DMSO-$d_6$) δ:8.95 (1H, s, $C_5$—H), 7.65 (1H, d, J=14Hz, $C_8$—H), 7.10-7.50 (3H, m, ARM-H), 5.00-5.30 (4H, m, 2 x —$CH_2$N—), 4.30-5.00 (3H, m, $C_2$—H, $C_3$—H), 1.50 (3H, d, J=7Hz, $CH_3$)

Example 23

-(5-chloro-2-isoindolinyl)-9-fluoro-2,3-dihydro-3-methyl-7-oxo-7H-pyrido[1,2,3-de][1,4]-benzoxazine-6-carboxylic acid

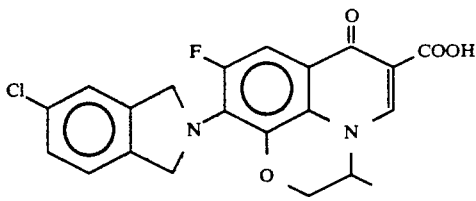

136 mg of 9,10-difluoro-2,3-dihydro-3-methyl-7-oxo-7H-pyrido[1,2,3-de][1,4]-benzoxazine-6-carboxylic acid, 101 mg of 5-chloroisoindoline, 152 mg of DBU, and 1.5 ml of anhydrous DMF were processed in the same manner as in Example 20 to produce 63 mg of the target compound.

Melting Point: 294°-300° C. (decomposed)

$^1$H-NMR (DMSO-$d_6$) δ:8.95 (1H, s, $C_5$—H), 7.60 (1H, d, J=15Hz, $C_8$—H), 7.30-7.50 (3H, m, ARM-H), 4.95-5.20 (4H, m, 2 x —$CH_2$N—), 4.30-4.95 (3H, m, $C_2$—H, $C_3$—H) 1.48 (3H, d, J=7Hz, $CH_3$)

Example 24

7(4-fluoro-2-isoindolinyl)-1-cyclopropyl-6,8-difluoro-1,4-dihydro-4-oxoquinoline-3-carboxylic acid

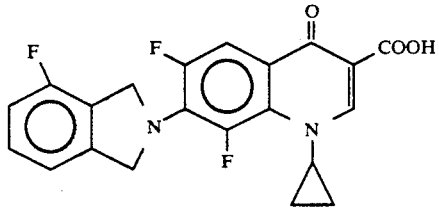

136 mg of 1-cyclopropyl-6,7,8-trifluoro-1,4-dihydro-4-oxoquinoline-3-carboxylic acid, 206 mg of 4-fluoroisoindoline, and 1.5 ml of anhydrous DMF were processed in the same manner as in Example 20 to produce 127 mg of the target compound.

Melting Point: 285°-287° C. (decomposed)

$^1$H-NMR (DMSO-$d_6$) δ:8.65 (1H, s, $C_2$—H), 7.83 (1H, d, J=14Hz, $C_5$—H), 7.10-7.45 (3H, m, ARM-H), 5.20 (4H, s, 2 x —$CH_2$N—), 4.15 (1H, m,

), 1.20 (4H, m,

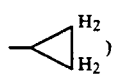)

Example 25

7-(4-chloro-2-isoindolinyl]-1-cyclopropyl-6,8-difluoro-1,4-dihydro-4-oxoquinoline-3-carboxylic acid

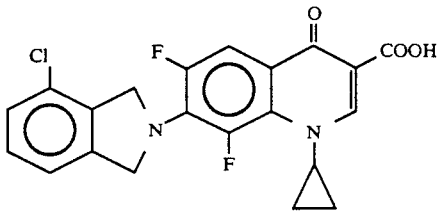

136 mg of 1-cyclopropyl-6,7,8-trifluoro-1,4-dihydro-4-oxoquinoline-3-carboxylic acid, 230 mg of 4-chloroisoindoline, and 1.5 ml of anhydrous DMF were processed in the same manner as in Example 20 to produce 100 mg of the target compound.

Melting Point: 294°-298° C. (decomposed)

$^1$H-NMR (DMSO-$d_6$) δ:8.67 (1H, s, $C_2$—H), 7.82 (1H, d, J=14Hz, $C_5$—H], 7.40 (3H, s, ARM-H), 5.10-5.25 (4H, m, 2x —$CH_2$N—), 4.10-4.25 (1H, m,

), 1.05-1.27 (4H, m,

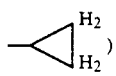)

Example 26

7-5-chloro-2-isoindolinyl)-1-cyclopropyl-6,8-difluoro-1,4-dihydro-4-oxoquinoline-3-carboxylic acid

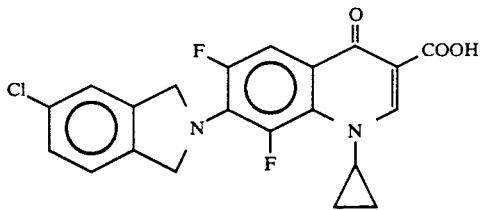

136 mg of 1-cyclopropyl-6,7,8-trifluoro-1,4-dihydro-4-oxoquinoline-3-carboxylic acid, 115 mg of 5-chloroisoindoline, 114 mg of DBU, and 1.5 ml of anhydrous DMF were processed in the same manner as in Example 20 to produce 54 mg of the target compound.

Melting Point: 260°-264° C. (decomposed)

$^1$H-NMR (DMSO-$d_6$) δ:8.68 (1H, s, $C_2$—H), 7.80 (1H, d, J=14Hz, $C_5$—H), 7.35-7.65 (3H, m, ARM-H), 5.15 (4H, brs, 2 x —$CH_2$N—), 4.05-4.20 (1H, m,

), 1.25 (4H, brs,

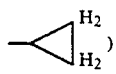

Example 27

10-(4-chloro-2-isoindolinyl)-9-fluoro-2,3-dihydro-3-methyl-7-oxo-7H-pyrido[1,2,3-de][1,4]-benzoxazine-6-carboxylic acid

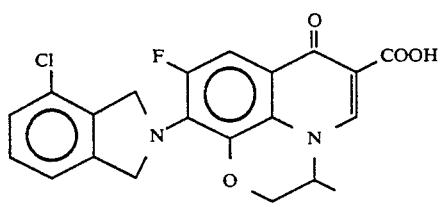

141 mg of 9,10-difluoro-2,3-dihydro-3-methyl-7-oxo-7H-pyrido[1,2,3-de][1,4]-benzoxazine-6-carboxylic acid, 115 mg of 4-chloroisoindoline, 114 mg of DBU, and 1.5 ml of anhydrous DMF were processed in the same manner as in Example 20 to produce 70 mg of the target compound.

Melting Point: 281°–285° C. (decomposed)

$^1$H-NMR (DMSO-$d_6$) δ:8.95 (1H, s, $C_5$—H), 7.63 (1H, d, J=14Hz, $C_8$—H), 7.35 (3H, brs, ARM-H), 4.95-5.30 (4H, m, 2 x —$CH_2$N—), 4.30-4.95 (3H, m, $C_2$—H, $C_3$—H), 1.45 (3H, d, J=7Hz, $CH_3$)

Example 28

7-(5-fluoro-2-isoindolinyl)-1-cyclopropyl-6,8-difluoro-1,4-dihydro-4-oxoquinoline-3-carboxylic acid

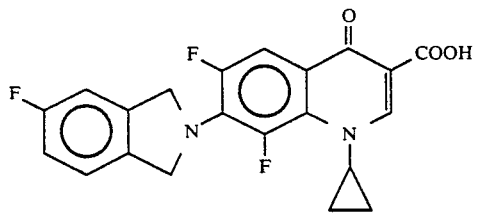

170 mg of 1-cyclopropyl-6,7,8-trifluoro-1,4-dihydro-4-oxoquinoline-3-carboxylic acid, 247 mg of 5-fluoroisoindoline, and 1.5 ml of anhydrous DMF were processed in the same manner as in Example 20 to produce 109 mg of the target compound.

Melting Point: 278°–281° C. (decomposed)

$^1$H-NMR (DMSO-$d_6$) δ:8.68 (1H $C_2$—H) 7.83 (1H, d, J=14Hz, $C_5$—H), 7.15-7.55 (3H, m, ARM-H), 5.05-5.35 (4H, m, 2 x —$CH_2$N—), 4.05-4.25 (1H, m,

1.26 (4H, brs,

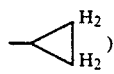

Example 29

10-5-fluoro-2-isoindolinyl)-9-fluoro-2,3-dihydro-3-methyl-7-oxo-7H-pyrido[1,2,3-de][1,4]-benzoxazine-6-carboxylic acid

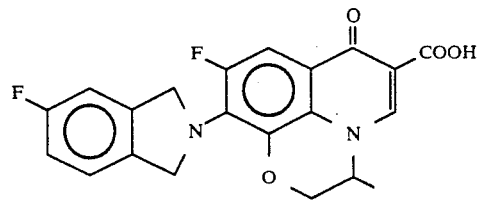

169 mg of 9,10-difluoro-2,3-dihydro-3-methyl-7-oxo-7H-pyrido[1,2,3-de][1,4]-benzoxazine-6-carboxylic acid, 123 mg of 5-fluoroisoindoline, 137 mg of DBU, and 1.5 ml of anhydrous DMF were processed in the same manner as in Example 20 to produce 116 mg of the target compound.

Melting Point: above 300° C.

$^1$H-NMR (DMSO-$d_6$) δ:8.98 (1H, s, $C_5$—H), 7.65 (1H, d, J=14Hz, $C_8$—H) 7.08-7.50 (3H m, ARM-H) 5.00-5.25 (4H, m, 2 x —$CH_2$N—), 4.33-5.00 (3H, m, $C_2$—H, $C_3$—H), 1.52 (3H, d, J=7Hz, $CH_3$)

Example 30

7-(4-bromo-2-isoindolinyl)-1-cyclopropyl-6,8-difluoro-1,4-dihydro-4-oxoquinoline-3-carboxylic acid

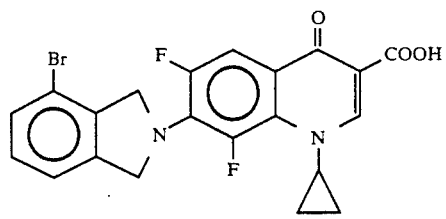

142 mg of 1-cyclopropyl-6,7,8-trifluoro-1,4-dihydro-4-oxoquinoline-3-carboxylic acid, 149 mg of 4-bromoisoindoline, 114 mg of DBU, and 1.5 ml of anhydrous DMF were processed in the same manner as in Example 20 to produce 43 mg of the target compound.

Melting Point: 288°–294° C. (decomposed)

$^1$H-NMR (DMSO-$d_6$) δ:8.70 (1H, s, $C_2$—H), 7.85 (1H, d, J=14Hz, $C_5$—H), 7.20-7.65 (3H, m, ARM-H), 5.10-5.35 (4H, m, 2 x —$CH_2$N—), 4.20 (1H, m,

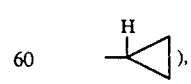

1.20 (4H, m,

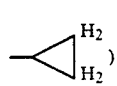

Example 31

10-(4-bromo-2-isoindolinyl)-9-fluoro-2,3-dihydro-3-methyl-7-oxo-7H-pyrido[1,2,3-de][1,4]-benzoxazine-6-carboxylic acid

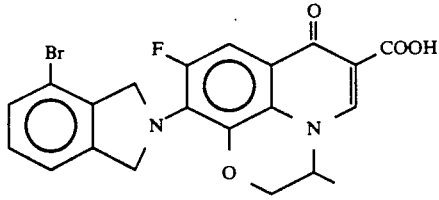

142 mg of 9,10-difluoro-2,3-dihydro-3-methyl-7--oxo-7H-pyrido[1,2,3-de][1,4]-benzoxazine-6-carboxylic acid, 149 mg of 4-bromoisoindoline, 114 mg of DBU, and 1.5 ml of anhydrous DMF were processed in the same manner as in Example 20 to produce 103 mg of the target compound.

Melting Point: 291°–295° C. (decomposed)

$^1$H-NMR (DMSO-d$_6$) δ:8.95 (1H, s, C$_5$—H), 7.20–7.70 (4H, m, C$_8$—H, ARM-H), 4.96–5.30 (4H, m, 2 x —CH$_2$N—), 4.30–4.96 (C$_2$—H, C$_3$—H), 1.45 (3H, brs, CH$_3$)

Example 32

7(5-bromo-2-isoindolinyl)-1-cyclopropyl-6,8-difluoro-1,4- dihydro-4-oxoquinoline-3-carboxylic acid

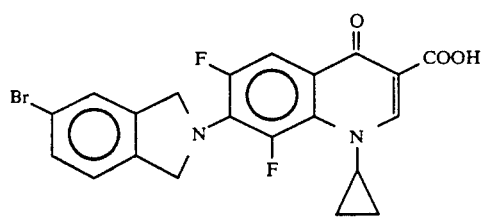

142 mg of 1-cyclopropyl-6,7,8-trifluoro-1,4-dihydro-4- oxoquinoline-3-carboxylic acid, 150 mg of 5-bromoisoindoline, 114 mg of DBU, and 1.5 ml of anhydrous DMF were processed in the same manner as in Example 20 to produce 82 mg of the target compound.

Melting Point: 243°–251° C. (decomposed)

$^1$H-NMR (DMSO-d$_6$) δ:8.63 1H, s, C$_2$—H), 7.78 (1H, d, J=14Hz, C$_5$—H), 7.32–7.70 (3H, m, ARM-H), 5.00–5.20 (4H, m, 2 x —CH$_2$N—), 4.00–4.16 (1H, m,

1.20 (4H, brs,

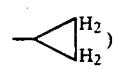

Example 33

10-(5-bromo-2-isoindolinyl)-9-fluoro-2,3-dihydro-3-methyl-7-oxo-7H-pyrido[1,2,3-de][1,4]-benzoxazine-6-carboxylic acid

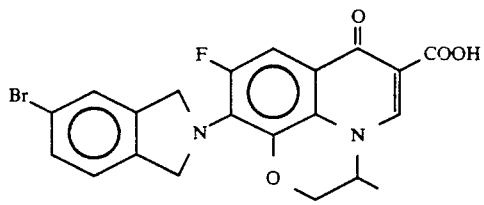

142 mg of 9,10-difluoro-2,3-dihydro-3-methyl-7-oxo-7H-pyrido[1,2,3-de][1,4]-benzoxazine-6-carboxylic acid, 150 mg of 5-bromoisoindoline, 114 mg of DBU, and 1.5 ml of anhydrous DMF were processed in the same manner as in Example 20 to produce 63 mg of the target compound.

Melting Point: 290°–294° C. (decomposed)

$^1$H-NMR (DMSO-d$_6$) δ:8.95 (1H, s, C$_5$—H), 7.30–7.70 (4H, $^1$H-NMR (DMSO-d$_6$) δ:8.95 (1H, s, C$_5$—H), 7.30–7.70 (4H, m, C$_8$—H, ARM-H), 4.96–5.23 (4H, m, 2 x —CH$_2$N—), 4.30–4.96 (3H, m, C$_2$—H, C$_3$—H), 1.48 (3H, d, J=7H$_Z$)

Example 34

7-(2-isoindolinyl)-1-ethyl-6,8-difluoro-1,4-dihydro-4-oxoquinoline-3-carboxylic acid

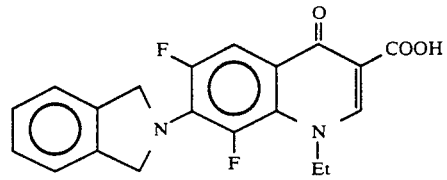

136 mg of 1-ethyl-6,7,8-trifluoro-1,4-dihydro-4- oxoquinoline-3-carboxylic acid, 179 mg of isoindoline, 152 mg of DBU, and 1.5 ml of anhydrous DMF were processed in the same manner as in Example 20 to produce 68 mg of the target compound.

Melting Point 255°–258° C. (decomposed)

$^1$H-NMR (DMSO-d$_6$) δ:8.85 (1H, s, C$_2$—H), 7.85 (1H, d, J=14Hz, C$_5$—H), 7.25–7.45 (4H, m, ARM-H), 5.15 (4H, brs, 2 x —CH$_2$N—), 4.58 (2H q, J=7Hz, —CHHD 2 CH$_3$), 1.48 (3H, t, J=7Hz, —CH$_2$CH$_3$)

Example 35

7-(4-amino-2-isoindolinyl)-1-ethyl-6,8-difluoro-1,4-dihydro-4-oxoquinoline-3-carboxylic acid

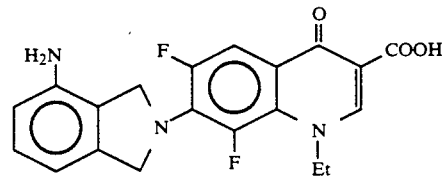

136 mg of 1-ethyl-6,7,8-trifluoro-1,4-dihydro-4-oxoquinoline-3-carboxylic acid, 100 mg of 4-aminoisoindoline, 114 mg of DBU, and 1.5 ml of anhydrous DMF were processed in the same manner as in Example 20 to produce 80 mg of the target compound.
Melting Point: 278°–280° C. (decomposed)
$^1$H-NMR (DMSO-d$_6$) δ:8.88 (1H, s, C$_2$—H), 7.83 (1H, d, (4H, m, 2 x —CH$_2$N—), 4.60 (2H, q, J=7H$_Z$, —CH$_2$CH$_3$), 1.50 (3H, t, J=7H$_Z$, —CH$_2$CH$_3$)

Example 36

7-(5-methoxy-2-isoindolinyl)-1-cyclopropyl-6,8-difluoro-1,4- dihydro-4-oxoquinoline-3-carboxylic acid

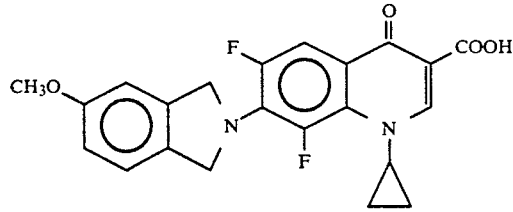

170 mg of 1-cyclopropyl-6,7,8-trifluoro-1,4-dihydro-4- oxoquinoline-3-carboxylic acid, 268 mg of 5-methoxyisoindoline, and 1.5 ml of anhydrous DMF were processed in the same manner as in Example 20 to produce 154 mg of the target compound.
Melting Point: 250°–252° C. (decomposed)
$^1$H-NMR (DMSO-d$_6$) δ:8.65 (1H, s, C$_2$—H), 7.80 (1H, d, J=14H$_Z$, C$_5$—H), 6.85–7.35 (3H, m, ARM-H), 5.00-5.20 (4H, m, 2 x —CH$_2$N—), 4.15 (2H, m,

3.78 (3H, s, OCH$_3$), 1.21 (4H, m,

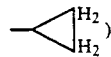

Example 37

10-(5-methoxy-2-isoindolinyl)-9-fluoro-2,3-dihydro-3-methyl-7-oxo-7H-pyrido[1,2,3-de][1,4]-benzoxazine-6-carboxylic acid

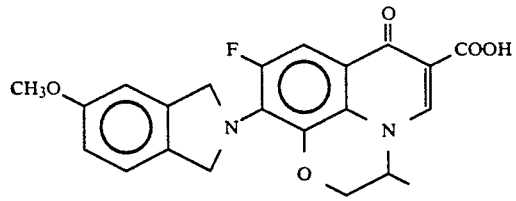

141 mg of 9,10-difluoro-2,3-dihydro-3-methyl-7-oxo-7H-pyrido[1,2,3-de][1,4]-benzoxazine-6-carboxylic acid, 104 mg of 5-methoxyisoindoline, 121 mg of DBU, and 1.5 ml of anhydrous DMF were processed in the same manner as in Example 20 to produce 105 mg of the target compound.
Melting Point: 251°–256° C. (decomposed)
$^1$H-NMR (DMSO-d$_6$) δ:8.95 (1H, s, C$_5$—H), 7.62 (1H, d, J=14H$_Z$, C$_8$—H), 6.83–7.30 (3H, m, ARM-H), 4.97–5.15 (4H, m, 2 x —CH$_2$N—), 4.30-4.96 (3H, m, C$_2$—H, C$_3$—H), 3.78 (3H, s, OCH$_3$), 1.48 (3H, d, J=7H$_Z$, —CH$_3$)

Example 38

7(5-methoxy-2-isoindolinyl)-1-ethyl-6,8-difluoro-1,4-dihydro-4-oxoquinoline-3-carboxylic acid

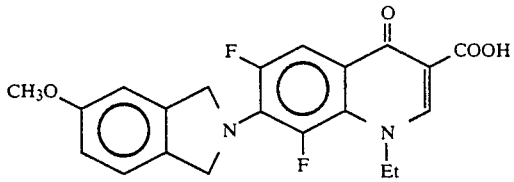

135 mg of 1-ethyl-6,7,8-trifluoro-1,4-dihydro-4- oxoquinoline-3-carboxylic acid, 104 mg of 5-methoxyisoindoline, 121 mg of DBU, and 1.5 ml of anhydrous DMF were processed in the same manner as in Example 20 to produce 63 mg of the target compound.
Melting Point: 261°–264° C. (decomposed)
$^1$H-NMR (DMSO-d$_6$) δ:8.80 (1H, s, C$_2$—H), 7.82 (1H, d, J=14H$_Z$, C$_5$—H), 6.80–7.05 (3H, m, ARM-H), 5.00–5.20 (4H, m, 2 x —CH$_2$N—), 4.58 (2H, q, J=7H$_Z$, —CH$_2$CH$_3$), 3.80 (3H, s, OCH$_3$), 1.47 (3H, t, J=7H$_Z$, CH$_3$)

Example 39

7-(4-methoxy-2-isoindolinyl)-1-cyclopropyl-5-amino-6,8- difluoro-1,4-dihydro-4-oxoquinoline-3-carboxylic acid

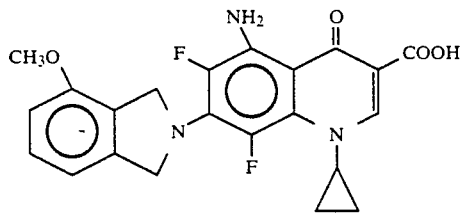

4.16 g of 1-cyclopropyl-5-amino-6,7,8-trifluoro-1,4-dihydro-4-oxoquinoline-3-carboxylic acid, 2.5 g of 4-methoxyisoindoline, 6.4 g of DBU, and 28 ml of anhydrous DMF were processed in the same manner as in Example 20 to produce 3.64 g of the target compound.
Melting Point 251°–255° C. (decomposed)
$^1$H-NMR (CDCl$_3$—CF$_3$COOD, 10:1) δ:8.86 (1H, s, C$_2$—H), 6.81–7.36 (3H, m, ARM-H), 5.24–5.30 (4H, m, 2 x —CH$_2$N—), 4.16 (1H, m,

3.89 (3H, s, OCH$_3$), 1.20–1.38 (4H m,

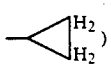

Example 40

7-4-amino-2-isoindolinyl)-1-cyclopropyl-5-amino-6,8-difluoro-1,4-dihydro-4-oxoquinoline-3-carboxylic acid

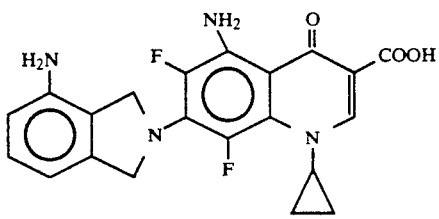

7.45 g of 1-cyclopropyl-5-amino-6,7,8-trifluoro-1,4-dihydro-4-oxoquinoline-3-carboxylic acid, 4.02 g of 4-aminoisoindoline, 11.4 g of DBU, and 50 ml of anhydrous DMF were processed in the same manner as in Example 20 to produce 5.92 g of the target compound.

Melting Point 238°–242° C. (decomposed)

1H-NMR (DMSO-$d_6$) δ:8.47 (1H, s, $C_2$—H), 6.50.–7.03 (3H, m, ARM-H), 4.90–5.02 (4H, m, 2 x —$CH_2N$—), 4.01 (1H, m,

1.11 (4H, m,

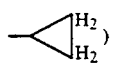

Example 41

7-(5-amino-2-isoindolinyl)-1-cyclopropyl-5-amino-6,8-difluoro-1,4-dihydro-4-oxoquinoline-3-carboxylic acid

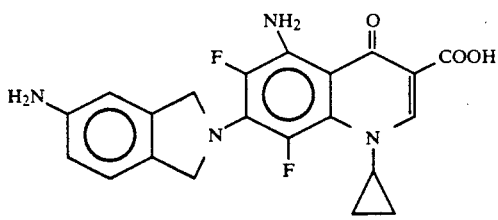

200 mg of 1-cyclopropyl-5-amino-6,7,8-trifluoro-1,4-dihydro-4-oxoquinoline-3-carboxylic acid, 99 mg of 5-aminoisoindoline, 200 mg of DBU, and 1.5 ml of anhydrous DMF were processed in the same manner as in Example 20 to produce 117 mg of the target compound.

Melting Point 270°–275° C. (decomposed)

1H-NMR (DMSO-$d_6$) δ:8.44 (1H, s, $C_2$—H), 6.98–7.14 (3H, m, ARM-H), 4.93–4.95 (4H, m, 2 x —$CH_2N$—), 3.98 (1H, m,

1.07 (4H, m,

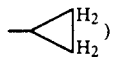

Example 42

7-(4-fluoro-2-isoindolinyl)-1-cyclopropyl-5-amino-6,8-difluoro-1,4-dihydro-4-oxoquinoline-3-carboxylic acid

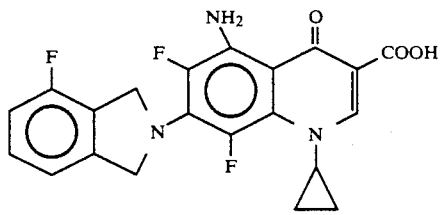

200 mg of 1-cyclopropyl-5-amino-6,7,8-trifluoro-1,4-dihydro-4-oxoquinoline-3-carboxylic acid, 101 mg of 4-fluoroisoindoline, 200 mg of DBU, and 1.5 ml of anhydrous DMF were processed in the same manner as in Example 20 to produce 59 mg of the target compound.

Melting Point: 270°–275° C. (decomposed)

$^1$H-NMR (CDCl$_3$—CF$_3$COOD, 10:1) δ:8.92 (1H, s, $C_2$—H), 7.01–7.40 (3H, m, ARM-H), 5.34 (4H, brs, 2 x —$CH_2N$—), 4.20 (1H, m,

1.23–1.42 (4H, s,

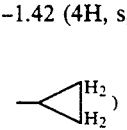

Example 43

7-(5-fluoro-2-isoindolinyl)-1-cyclopropyl-5-amino-6,8-difluoro-1,4-dihydro-4-oxoquinoline-3-carboxylic acid

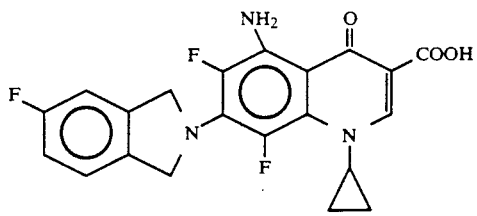

268 mg of 1-cyclopropyl-5-amino-6,7,8-trifluoro-1,4-dihydro-4-oxoquinoline-3-carboxylic acid, 137 mg of 5-fluoroisoindoline, 274 mg of DBU, and 2 ml of anhydrous DMF were processed in the same manner as in Example 20 to produce 266 mg of the target compound.

Melting Point: 240°–245° C. (decomposed)

$^1$H-NMR (CDCl$_3$—CF$_3$COOD, 10:1) δ:8.86 (1H, s, $C_2$—H), 7.00–7.29 (3H, m, ARM-H), 5.26 (4H, brs, 2 x —$CH_2N$—), 4.15 (1H, m,

1.20–1.37 (4H, m,

)

Example 44

7-(4-chloro-2-isoindolinyl)-1-cyclopropyl-5-amino-6,8-difluoro-1,4-dihydro-4-oxoquinoline-3-carboxylic acid

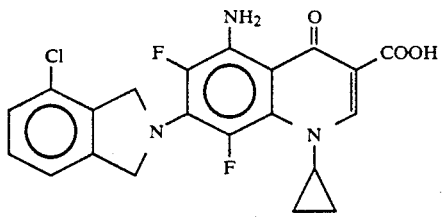

268 mg of 1-cyclopropyl-5-amino-6,7,8-trifluoro-1,4-dihydro-4-oxoquinoline-3-carboxylic acid, 154 mg of 4-chloroisoindoline, 274 mg of DBU, and 2 ml of anhydrous DMF were processed in the same manner as in Example 20 to produce 93 mg of the target compound.

Melting Point: above 280° C.

$^1$H-NMR (CDCl$_3$—CF$_3$COOD, 10:1) δ:8.91 (1H, s, C$_2$—H), 7.21–7.34 (3H, m, ARM-H), 5.31–5.37 (4H, m, 2 x —CH$_2$N—), 4.20 (1H, m,

), 1.23–1.40 (4H, m,

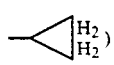)

Example 45

7-(5-chloro-2-isoindolinyl)-1-cyclopropyl-5amino-6,8-difluoro-1,4-dihydro-4-oxoquinoline-3-carboxylic acid

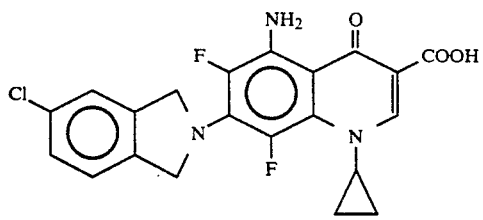

268 mg of 1-cyclopropyl-5-amino-6,7,8-trifluoro-1,4-dihydro-4-oxoquinoline-3-carboxylic acid, 154 mg of 5-chloroisoindoline, 274 mg of DBU, and 2 ml of anhydrous DMF were processed in the same manner as in Example 20 to produce 270 mg of the target compound.

Melting Point: 261°–265° C. (decomposed)

$^1$H-NMR (CDCl$_3$—CF$_3$COOD, 10:1) δ:8.88 (1H, s, C$_2$—H), 7.23–7.33 (3H, m, ARM-H), 5.26 (4H, brs, 2 x —CH$_2$N—), 4.17 (1H, m,

, 1.21–1.38 (4H, m,

)

Example 46

7(4-bromo-2-isoindolinyl)-1-cyclopropyl-5-amino-6,8-difluoro-1,4-dihydro-4-oxoquinoline-3-carboxylic acid

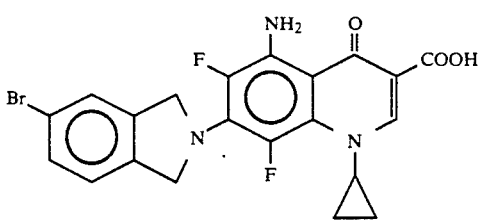

268 mg of 1-cyclopropyl-5-amino-6,7,8-trifluoro-1,4-dihydro-4-oxoquinoline-3-carboxylic acid, 198 mg of 4-bromoisoindoline, 274 mg of DBU, and 2 ml of anhydrous DMF were processed in the same manner as in Example 20 to produce 147 mg of the target compound.

Melting Point: above 280° C. (decomposed)

$^1$H-NMR (CDCl$_3$—CF$_3$COOD, 10:1) δ:8.91 (1H, s, C$_2$—H), 7.21–7.49 (3H, m, ARM-H), 5.26–5.40 (4H, m, 2 x —CH$_2$N—), 4.20 (1H, m,

), 1.22–1.41 (4H, m,

)

Example 47

7-(5-bromo-2-isoindolinyl)-1-cyclopropyl-5-amino-6,8-difluoro-1,4-dihydro-4-oxoquinoline-3-carboxylic acid

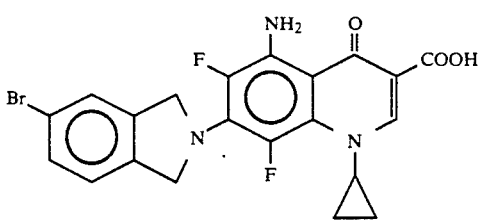

290 mg of 1-cyclopropyl-5-amino-6,7,8-trifluoro-1,4-dihydro-4-oxoquinoline-3-carboxylic acid, 200 mg of 5-bromoisoindoline, 290 mg of DBU, and 2 ml of anhydrous DMF were processed in the same manner as in Example 20 to produce 220 mg of the target compound.

Melting Point: 266°–267° C. (decomposed)

$^1$H-NMR (CDCl$_3$—CF$_3$COOD, 10:1) δ:8.90 (1H, s, C$_2$—H), 7.19–7.50 (3H, m, ARM-H), 5.20–5.40 (4H, m, 2 x —CH$_2$N—), 4.19 (1H, m,

1.20–1.40 (4H, m,

Example 48

7-(5-methoxy-2-isoindolinyl)-1-cyclopropyl-5-amino-6,8-difluoro-1,4-dihydro-4-oxoquinoline-3-carboxylic acid

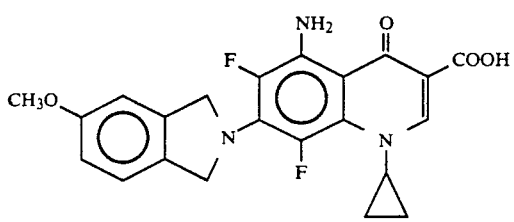

298 mg of 1-cyclopropyl-5-amino-6,7,8-trifluoro-1,4-dihydro-4-oxoquinoline-3-carboxylic acid, 230 mg of 5-methoxyisoindoline, 300 mg of DBU, and 2 ml of anhydrous DMF were processed in the same manner as in Example 20 to produce 300 mg of the target compound.

Melting Point: 252°–255° C. (decomposed)

$^1$H-NMR (CDCl$_3$—CF$_3$COOD, 10:1) δ:8.88 (1H, s, C$_2$—H), 6.89 –7.26 (3H, m, ARM-H), 5.20–5.35 (4H, m, 2 x —CH$_2$N—), 4.17 (1H, m,

1.20–1.45 (4H, m,

Example 49

7-(4-methoxy-2-isoindolinyl)-1-cyclopropyl-5,6,8-trifluoro-1,4-dihydro-4-oxoquinoline-3-carboxylic acid

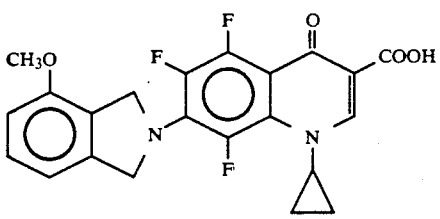

210 mg of 1-cyclopropyl-5,6,7,8-tetrafluoro-1,4-dihydro-4-oxoquinoline-3-carboxylic acid, 115 mg of 4-methoxyisoindoline, 213 mg of DBU, and 1.5 ml of anhydrous DMF were processed in the same manner as in Example 20 to produce 138 mg of the target compound.

Melting Point: above 280° C.

$^1$H-NMR (CDCl$_3$—CF$_3$COOD, 10:1) δ:9.02 (1H, s, C$_2$—H), 6.84–7.39 (3H, m, ARM-H), 5.32–5.38 (4H, m, 2 x —CH$_2$N—), 4.29 (1H, m,

3.91 (3H, s, OCH$_3$), 1.27–1.45 (4H, m,

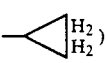

Example 50

7-(4-fluoro-2-isoindolinyl)-1-cyclopropyl-5,6,8-trifluoro-1,4-dihydro-4-oxoquinoline-3-carboxylic acid

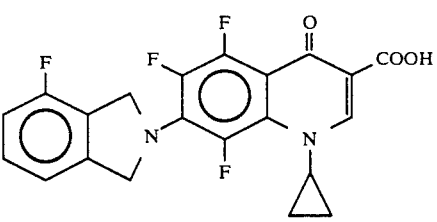

210 mg of 1-cyclopropyl-5,6,7,8-tetrafluoro-1,4-dihydro-4-oxoquinoline-3-carboxylic acid, 106 mg of 4-fluoroisoindoline, 213 mg of DBU, and 1.5 ml of anhydrous DMF were processed in the same manner as in Example 20 to produce 35 mg of the target compound.

Melting Point: 238°–245° C. (decomposed)

$^1$H-NMR (CDl$_3$—CF$_3$COOD, 10:1) δ:8.97 (1H, s, C$_2$—H), 7.02–7.41 (3H, m, ARM-H), 5.37 (4H, brs, 2 x —CH$_2$N—),, 4.22 (1H, m,

1.24–1.42 (4H, m,

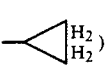

Example 51

7(5-fluoro-2-isoindolinyl)-1-cyclopropyl-5,6,8-trifluoro-1,4-dihydro-4-oxoquinoline-3-carboxylic acid

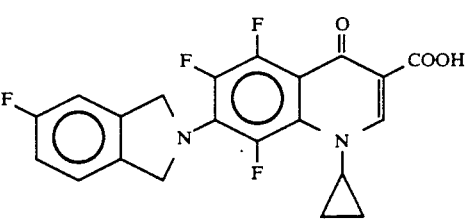

210 mg of 1-cyclopropyl-5,6,7,8-tetrafluoro-1,4-dihydro-4-oxoquinoline-3-carboxylic acid, 106 mg of 5-fluoroisoindoline, 213 mg of DBU, and 1.5 ml of anhydrous DMF were processed in the same manner as in Example 20 to produce 108 mg of the target compound.

Melting Point: 266°–272° C. (decomposed)

¹H-NMR (CDCl₃—CF₃COOD, 10:1) δ:9.03 (1H, s, C₂—H), 7.03–7.33 (3H, m, ARM-H), 5.36 (4H, brs, 2 x —CH₂N—), 4.30 (1H, m,

1.27–1.44 (4H, m,

Example 52

7-(4-chloro-2-isoindolinyl)-1-cyclopropyl-5,6,8-trifluoro-1,4-dihydro-4-oxoquinoline-3-carboxylic acid

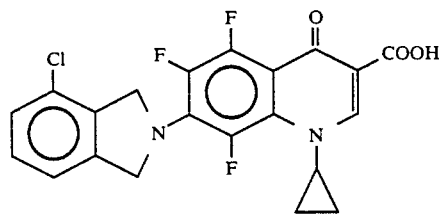

210 mg of 1-cyclopropyl-5,6,7,8-tetrafluoro-1,4-dihydro-4-oxoquinoline-3-carboxylic acid, 120 mg of 4-chloroisoindoline, 213 mg of DBU, and 1.5 ml of anhydrous DMF were processed in the same manner as in Example 20 to produce 64 mg of the target compound.

Melting Point: 279°–284° C. (decomposed)

¹H-NMR (CDCl₃—CF₃COOD, 10:1) δ:9.05 (1H, s, C₂—H), 7.26–7.36 (3H, m, ARM-H), 5.39–5.45 (4H, m, 2 x —CH₂N—), 4.31 (1H, m,

1.29–1.47 (4H, m,

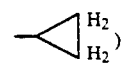

Example 53

7-(2-isoindolinyl)-1-cyclopropyl-5(2-hydroxyethylamino)-6,8-difluoro-1,4-dihydro-4-oxoquinoline-3-carboxylic acid

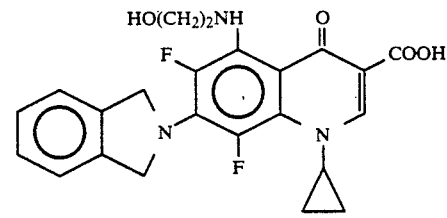

205 mg of 1-cyclopropyl-5(2-hydroxyethylamino)-6,7,8-trifluoro-1,4-dihydro-4-oxoquinoline-3-carboxylic acid, 119 mg of isoindoline, 182 mg of DBU, and 1.5 ml of anhydrous DMF were processed in the same manner as in Example 20 to produce 113 mg of the target compound.

¹H-NMR (CDCL₃—CF₃COOD, 10:1) δ:8.92 (1H, s, C₂—H), 7.25–7.39 (4H, m, ARM-H), 5.31 (4H, brs, 2 x —CH₂N—), 4.24 (2H, m, —CH₂OH), 4.15 (1H, m,

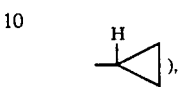

3.77 (2H, m, —NHCH₂—), 1.22–1.40 (4H, m,

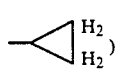

Example 54

7-(4-methoxy-2-isoindolinyl)-1-cyclopropyl-5-(2-hydroxyethylamino)-6,8-difluoro-1,4-dihydro-4-oxoquinoline-3-carboxylic acid

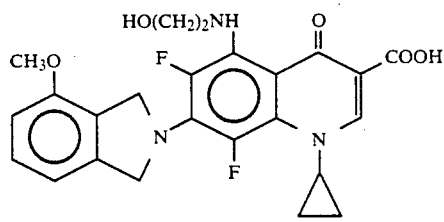

205 mg of 1-cyclopropyl-5-(2-hydroxyethylamino)-6,7,8- trifluoro-1,4-dihydro-4-oxoquinoline-3-carboxylic acid, 150 mg of 4-methoxyisoindoline, 182 mg of DBU, and 1.5 ml of anhydrous DMF were processed in the same manner as in Example 20 to produce 131 mg of the target compound.

¹H-NMR (CDCl₃—CF₃COOD 10:1) δ:8.90 (1H, s, C₂—H), 6.82–7.36 (3H, m, ARM-H), 5.24–5.29 (4H, m, 2 x —CH₂N—), 4.23 (2H, m, —CH₂OH), 4.15 (1H, m,

3.89 (3H, s, OCH₃), 3.76 (2H, m, —NHCH₂—), 1.20–1.39 (4H, m,

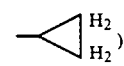

Example 55

7-(4-amino-2-isoindolinyl)-1-cyclopropyl-5-(2-hydroxyethylamino)-6,8-difluoro-1,4-dihydro-4-oxoquinoline-3-carboxylic acid

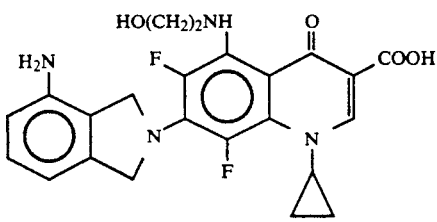

205 mg of 1-cyclopropyl-5-(2-hydroxyethylamino)-6,7,8-trifluoro-1,4-dihydro-4-oxoquinoline-3carboxylic acid, 100 mg of 4-aminoisoindoline, 182 mg of DBU, and 1.5 ml of anhydrous DMF were processed in the same manner as in Example 20 to produce 97 mg of the target compound.

$^1$H-NMR (DMSO-d$_6$) δ:8.62 (1H, s, C$_2$—H), 6.48–6.98 (3H, m, ARM-H), 4.82–4.94 (4H, m, 2 x —CH$_2$N—), 4.00 (1H, m,

1.16 (4H, m,

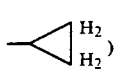

Example 56

7(4-fluoro-2-isoindolinyl)-1-cyclopropyl-5-(2-hydroxyethylamino)-6,8-difluoro-1,4-dihydro-4-oxoquinoline-3-carboxylic acid

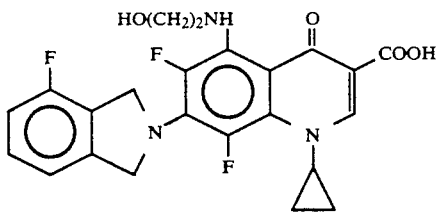

205 mg of 1-cyclopropyl-5-(2-hydroxyethylamino)-6,7,8-trifluoro-1,4-dihydro-4-oxoquinoline-3-carboxylic acid, 91 mg of 4-fluoroisoindoline, 182 mg of DBU, and 1.5 ml of anhydrous DMF were processed in the same manner as in Example 20 to produce 97 mg of the target compound.

$^1$H-NMR (CDCl$_3$—CF$_3$COOD, 10:1) δ:8.93 (1H, s, C$_2$—H), 7.00–7.40 (3H, m, ARM-H), 5.32 (4H, brs, 2 x —CH$_2$N—), 4.24 (2H, m, —CH$_2$OH), 4.18 (1H, m,

3.78 (2H, m, —NHCH$_2$—), 1.21–1.40 (4H, m,

Example 57

7-(4-chloro-2-isoindolinyl)-1-cyclopropyl-5-(2-hydroxyethylamino)-6,8-difluoro-1,4-dihydro-4-oxoquinoline-3-carboxylic acid

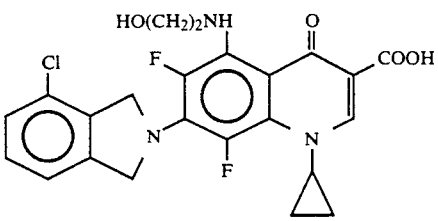

205 mg of 1-cyclopropyl-5-(2-hydroxyethylamino)-6,7,8- trifluoro-1,4-dihydro-4-oxoquinoline-3-carboxylic acid, 101 mg of 4-chloroisoindoline, 182 mg of DBU, and 1.5 ml of anhydrous DMF were processed in the same manner as in Example 20 to produce 100 mg of the target compound.

$^1$H-NMR (CDCl$_3$—CF$_3$COOD, 10:1) δ:8.93 (1H, s, C$_2$—H), 7.22–7.33 (3H, m, ARM-H), 5.30–5.35 (4H, m, 2 x —CH$_2$N—), 4.25 (2H, —CH$_2$OH), 4.19 (1H, m,

3.78 (2H, m, —NHCH$_2$—), 1.22–1.41 (4H, m,

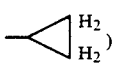

Example 58

7-(4-bromo-2-isoindolinyl) 1-cyclopropyl-5-(2-hydroxyethylamino)-6,8-difluoro-1,4-dihydro-4-oxoquinoline-3-carboxylic acid

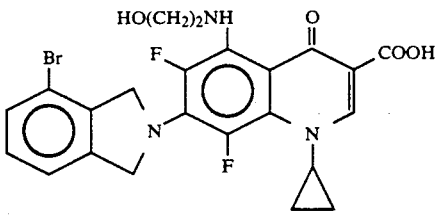

205 mg of 1-cyclopropyl-5-(2-hydroxyethylamino)-6,7,8- trifluoro-1,4-dihydro-4-oxoquinoline-3-carboxylic acid, 131 mg of 4-bromoisoindoline, 182 mg of DBU, and 1.5 ml of are anhydrous DMF were processed in the same manner as in Example 20 to produce 102 mg of the target compound.

$^1$H-NMR (CDCl$_3$—CF$_3$COOD, 10:1) δ:8.93 (1H, s, C$_2$—H), 7.22–7.51 (3H, m, ARM-H), 5.25–5.38 (4H, m, 2 x —CH$_2$N—), 4.24 (2H, m, —CH$_2$OH), 4.19 (1H, m,

3.78 (2H, m, —NHC$\underline{H}_2$—), 1.22–1.41 (4H, m,

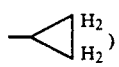

Example 59

7-(4-nitro-2-isoindolinyl)-1-cyclopropyl-6,8-difluoro-1,4- dihydro-4-oxoquinoline-3-carboxylic acid

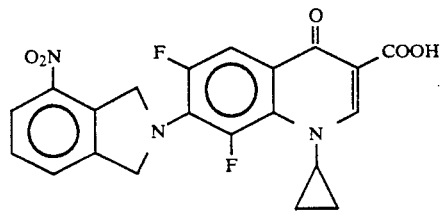

171 mg of 1-cyclopropyl-6,7,8-trifluoro-1,4-dihydro-4- oxoquinoline-3-carboxylic acid, 176 mg of 4-nitroisoindoline hydrobromide, 164 mg of DBU, and 1.5 ml of anhydrous DMF were processed in the same manner as in Example 20 to produce 55 mg of the target compound.

Example 60

7-(4-nitro-2-isoindolinyl)-1-ethyl-6,8-difluoro-1,4-dihydro- 4-oxoquinoline-3-carboxylic acid

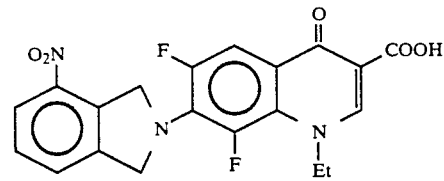

147 mg of 1-ethyl-6,7,8-trifluoro-1,4-dihydro-4- oxoquinoline-3-carboxylic acid, 176 mg of 4-nitroisoindoline hydrobromide, 164 mg of DBU, and 1.5 ml of anhydrous DMF were processed in the same manner as in Example 20 to produce 97 mg of the target compound.

Example 61

7-(4-nitro-2-isoindolinyl)-1-(4-fluorophenyl)-6,8-difluoro-1,4-dihydro-4-oxoquinoline-3-carboxylic acid

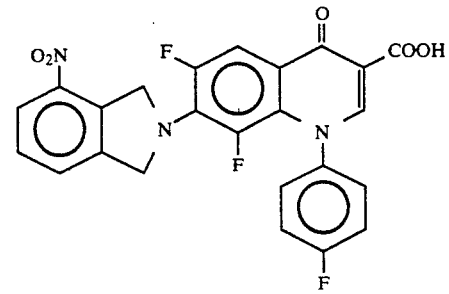

200 mg of 1-(4-fluorophenyl)-6,7,8-trifluoro-1,4-dihydro-4-oxoquinoline-3-carboxylic acid, 176 mg of 4-nitroisoindoline, 164 mg of DBU, and 1.5 ml of anhydrous DMF were processed in the same manner as in Example 20 to produce 102 mg of the target compound.

Example 62

10-(4-nitro-2-isoindolinyl)-9-fluoro-2,3-dihydro-3-methyl-7-oxo-7H-pyrido[1,2,3-de][1,4]-benzoxazine-6-carboxylic acid

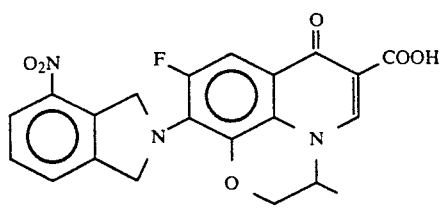

185 mg of 9,10-difluoro-2,3-dihydro-3-methyl-7-oxo-7H-pyrido[1,2,3-de][1,4]-benzoxazine-6-carboxylic acid, 176 mg of 4-nitroisoindoline hydrobromide, 164 mg of DBU, and 1.5 ml of anhydrous DMF were processed in the same manner as in Example 20 to produce 131 mg of the target compound.

Example 63

7-(4-nitro-2-isoindolinyl)-1-(2,4-difluorophenyl)-6,8-difluoro-1,4-dihydro-4-oxoquinoline-3-carboxylic acid

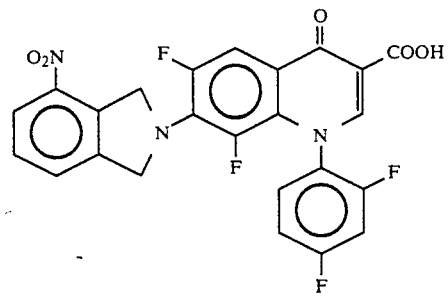

213 mg of 1-(2,4-difluorophenyl)-6,7,8-trifluoro-1,4-dihydro-4-oxoquinoline-3-carboxylic acid, 176 mg of 4-nitroisoindoline hydrobromide, 164 mg of DBU, and 1.5 ml of anhydrous DMF were processed in the same manner as in Example 20 to produce 47 mg of the target compound.

Example 64

7-(4-nitro-2-isoindolinyl)-1-cyclopropyl-6-fluoro-1,4-dihydro-4-oxoquinoline-3-carboxylic acid

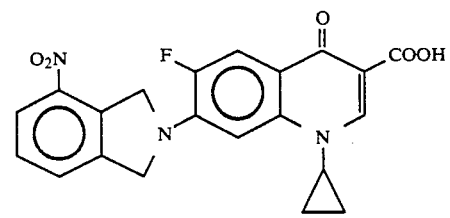

159 mg of 1-cyclopropyl-6,7-difluoro-1,4-dihydro-4-oxoquinoline-3-carboxylic acid, 176 mg of 4-nitroisoindoline hydrobromide, 164 mg of DBU, and 1.5 ml of anhydrous DMF were processed in the same manner as in Example 20 to produce 82 mg of the target compound.

Example 65

7-(4-nitro-2-isoindolinyl)-1-ethyl-6-fluoro-1,4-dihydro-4-oxoquinoline-3-carboxylic acid

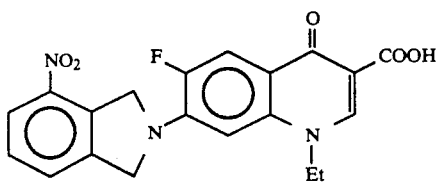

151 mg of 1-ethyl-6,7-difluoro-1,4-dihydro-4-oxoquinoline-3-carboxylic acid, 176 mg of 4-nitroisoindoline hydrobromide, 164 mg of DBU, and 1.5 ml of anhydrous DMF were processed in the same manner as in Example 20 to produce 133 mg of the target compound.

Example 66

7-(4-bromo-2-isoindolinyl)-1-(4-fluorophenyl)-6,8-difluoro-1,4-dihydro-4-oxoquinoline-3-carboxylic acid

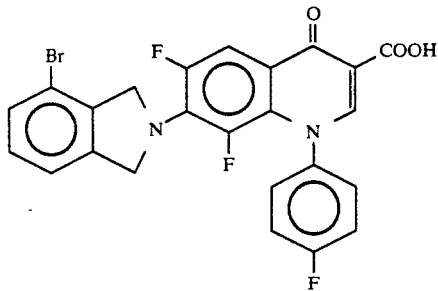

170 mg of 1-(4-fluorophenyl)-6,7,8-trifluoro-1,4-dihydro-4-oxoquinoline-3-carboxylic acid, 300 mg of 4-bromoisoindoline, and 1.5 ml of anhydrous DMF were processed in the same manner as in Example 20 to produce 162 mg of the target compound.

Melting Point: 279°–290° C. (decomposed)

Example 67

7-(4-bromo-2-isoindolinyl)-1-(2,4-difluorophenyl)-6,8-difluoro-1,4-dihydro-4-oxoquinoline-3-carboxylic acid

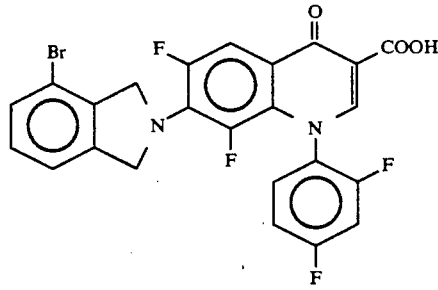

178 mg of 1-(2,4-fluorophenyl)-6,7,8-trifluoro-1,4-dihydro-4-oxoquinoline-3-carboxylic acid, 119 mg of 4-bromoisoindoline, 137 mg of DBU, and 1.5 ml of anhydrous DMF were processed in the same manner as in Example 20 to produce 43 mg of the target compound.

Melting Point: 258°–268° C. (decomposed)

$^1$H-NMR (CDCl$_3$) δ:8.48 (1H, s, C$_2$—H), 7.98 (1H, d, 14Hz, C$_5$—H), 7.05–7.60 (6H, m, ARM-H), 4.95–5.25 (4H, m, 2 x —CH$_2$N—)

Example 68

7-(4-fluoro-2-isoindolinyl)-1-(4-fluorophenyl)-6,8-difluoro-1,4-dihydro-4-oxoquinoline-3-carboxylic acid

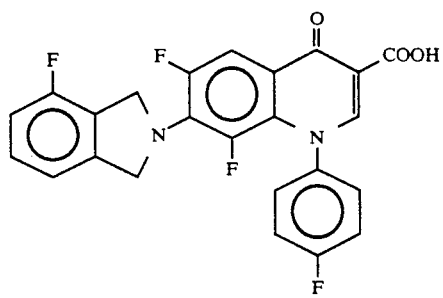

170 mg of 1-(4-fluorophenyl)-6,7,8-trifluoro-1,4-dihydro-4-oxoquinoline-3-carboxylic acid, 210 mg of 4-fluoroisoindoline, and 1.5 ml of anhydrous DMF were processed in the same manner as in Example 20 to produce 190 mg of the target compound.

Melting Point: above 300° C.

$^1$H-NMR (DMSO-d$_6$) δ:8.42 (1H, s, C$_2$—H), 7.89 (1H, d, J=14Hz, C$_5$—H), 7.05–7.85 (7H, m, ARM-H), 5.05 (4H, brs, 2 x —CH$_2$N—)

Example 69

7-(4-fluoro-2-isoindolinyl)-1-(2,4-difluorophenyl)-6,8-difluoro-1,4-dihydro-4-oxoquinoline-3-carboxylic acid

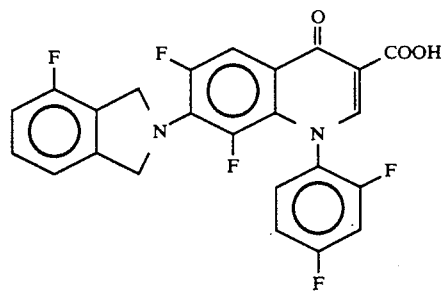

180 mg of 1-(2,4-difluorophenyl)-6,7,8-trifluoro-1,4-dihydro-4-oxoquinoline-3-carboxylic acid, 210 mg of 4-fluoroisoindoline, and 1.5 ml of anhydrous DMF were processed in the same manner as in Example 20 to produce 196 mg of the target compound.

Melting Point: above 300° C.

$^1$H-NMR (DMSO-d$_6$) δ:8.63 (1H s, C$_2$—H), 7.05–8.10 (7H, m, C$_5$—H, ARM-H) 5.05 (4H, brs, 2 x —CH$_2$—N—)

Example 70

7-(5-bromo-2-isoindolinyl)-1-(4-fluorophenyl)-6,8-difluoro-1,4-dihydro-4-oxoquinoline-3-carboxylic acid

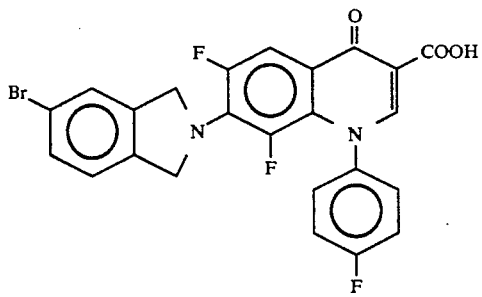

170 mg of 1-(4-fluorophenyl)-6,7,8-trifluoro-1,4-dihydro-4-oxoquinoline-3-carboxylic acid, 300 mg of 5-bromoisoindoline, and 1.5 ml of anhydrous DMF were processed in the same manner as in Example 20 to produce 144 mg of the target compound.

Melting Point: above 300° C.

Example 71

7-(5-bromo-2-isoindolinyl)-1-(2,4-difluorophenyl)-6,8-difluoro-1,4-dihydro-4-oxoquinoline-3-carboxylic acid

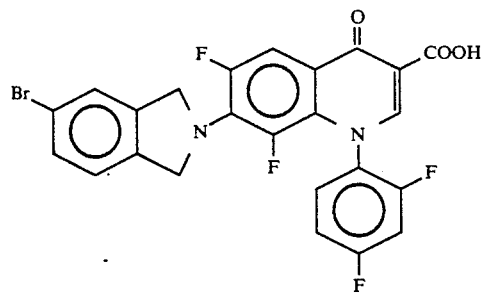

178 mg of 1-(2,4-difluorophenyl)-6,7,8-trifluoro-1,4-dihydro-4-oxoquinoline-3-carboxylic acid, 119 mg of 5-bromoisoindoline, 137 mg of DBU, and 1.5 ml of anhydrous DMF were processed in the same manner as in Example 20 to produce 44 mg of the target compound.

Melting Point: 251°-257° C.

$^1$H-NMR (CDCl$_3$) δ:8.48 (1H, s, C$_2$—H), 7.98 (1H, d, J=13H$_z$, C$_5$—H), 7.05-7.60 (6H, m, ARM-H), 4.95-5.10 (4H, m, 2 x —CH$_2$N—)

Example 72

7-(5-fluoro-2-isoindolinyl)-1-(4-fluorophenyl)-6,8-difluoro-1,4-dihydro-4-oxoquinoline-3-carboxylic acid

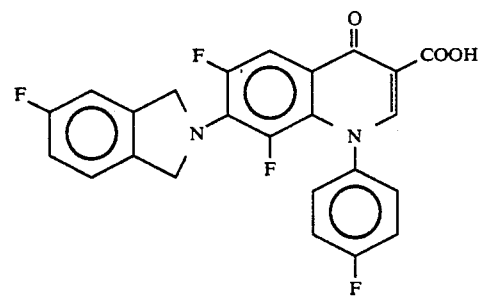

170 mg of 1-(4-fluorophenyl]-6,7,8-trifluoro-1,4-dihydro-4-oxoquinoline-3-carboxylic acid, 210 mg of 5-fluoroisoindoline, and 1.5 ml of anhydrous DMF were processed in the same manner as in Example 20 to produce 177 mg of the target compound.

Melting Point: above 300° C.

Example 73

7-(5 fluoro-2-isoindolinyl)-1-(2,4-fluorophenyl)-6,8-difluoro-1,4-dihydro-4-oxoquinoline-3-carboxylic acid

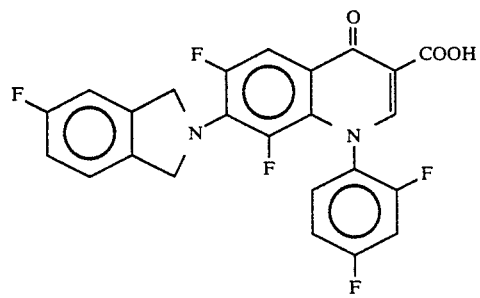

180 mg of 1-(2,4-difluorophenyl)-6,7,8-trifluoro-1,4-dihydro-4-oxoquinoline-3-carboxylic acid, 210 mg of 5-fluoroisoindoline, and 1.5 ml of anhydrous DMF were processed in the same manner as in Example 20 to produce 193 mg of the target compound.

Melting Point: 277°-282° C. (decomposed)

Example 74

7-(2-isoindolinyl)-1-(4-fluorophenyl)-6,8-difluoro-1,4-dihydro-4-oxoquinoline-3-carboxylic acid

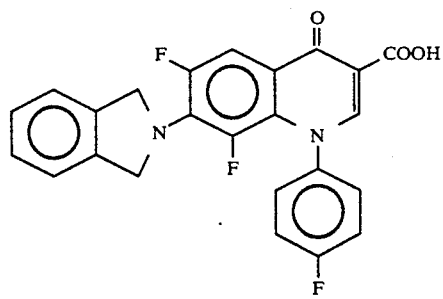

170 mg of 1-(4-fluoropnenyl)-6,7,8-trifluoro-1,4-dihydro-4-oxoquinoline-3-carboxylic acid, 180 mg of isoindoline, and 1.5 ml of anhydrous DMF were processed in the same manner as in Example 20 to produce 125 mg of the target compound.

Melting Point: above 300° C.

Example 75

7-(2-isoindolinyl)-1-(2,4-difluorophenyl)-6,8-difluoro-1,4-dihydro-4-oxoquinoline-3-carboxylic acid

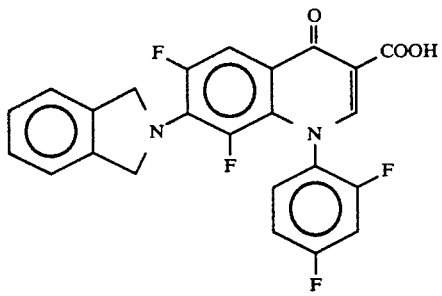

178 mg of 1-(2,4-difluorophenyl)-6,7,8-trifluoro-1,4-dihydro-4-oxoquinoline-3-carboxylic acid, 179 mg of isoindoline, and 1.5 ml of anhydrous DMF were processed in the same manner as in Example 20 to produce 76 mg of the target compound.

Melting Point: 264°–268° C.

$^1$H-NMR (CDCl$_3$) δ:8.48 (1H, s, C$_2$—H), 7.95 (1H, d, J=14Hz, C$_5$—H), 7.05–7.55 (7H, m, ARM-H), 5.10 (4H, s, 2 x —CH$_2$N—)

Example 76

7-(4-amino-2-isoindolinyl)-1-(4-fluorophenyl)-6,8-difluoro-1,4-dihydro-4-oxoquinoline-3-carboxylic acid.

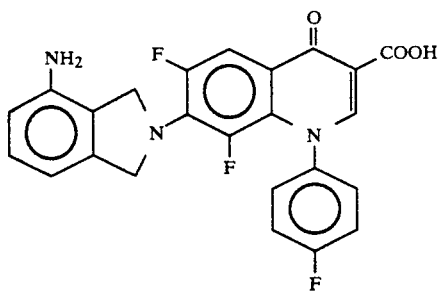

170 mg of 1-(4-fluorophenyl)-6,7,8-trifluoro-1,4-dihydro-4-oxoquinoline-3-carboxylic acid, 81 mg of 4-amino isoindoline, 137 mg of DBU, and 1.5 ml of anhydrous DMF were processed in the same manner as in Example 20 to produce 98 mg of the target compound.

Melting Point: 269°–274° C.

Example 77

7-(4-amino-2-isoindolinyl)-1-(2,4-difluorophenyl)-6,8-difluoro-1,4-dihydro-4-oxoquinoline-3-carboxylic acid

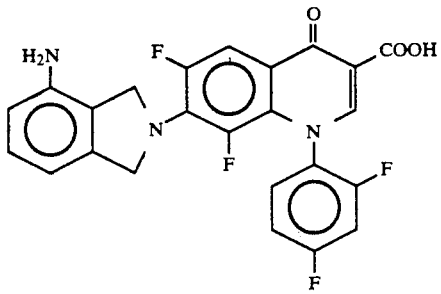

178 mg of 1-(2,4-difluorophenyl)-6,7,8-trifluoro-1,4-dihydro-4-oxoquinoline-3-carboxylic acid, 81 mg of 4-aminoisoindoline, 137 mg of DBU, and 1.5 ml of anhydrous DMF were processed in the same manner as in Example 20 to produce 75 mg of the target compound.

Melting Point: 264°–266° C.

$^1$H-NMR (CDCl$_3$) δ:8.48 (1H, s, C$_2$—H), 7.95 (1H, d, J=14Hz, C$_5$—H), 6.55–7.60 (6H, m, ARM-H), 4.90–5.16 (4H, m, 2 x —CH$_2$N—)

Example 78

7-(5-amino-2-isoindolinyl)-1-(4-fluorophenyl)-6,8-difluoro-1,4-dihydro-4-oxoquinoline-3-carboxylic acid

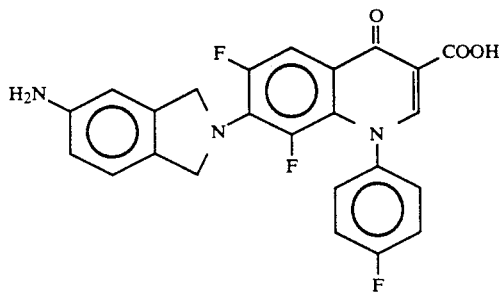

170 mg of 1-(4-fluorophenyl)-6,7,8-trifluoro-1,4-dihydro-4-oxoquinoline-3-carboxylic acid, 81 mg of 5-aminoisoindoline, 137 mg of DBU, and 1.5 ml of anhydrous DMF were processed in the same manner as in Example 20 to produce 78 mg of the target compound.

Melting Point: 249°–260° C. (decomposed)

1H-NMR (DMSO-D$_6$) δ:8.40 (1H, s, C$_2$—H), 6.45–7.95 (8H, m, C$_5$—H, ARM-H), 4.75–4.95 (4H, m, 2 x —CH$_2$N—)

Example 79

7-(5-amino-2-isoindolinyl)-1-(2,4-difluorophenyl)-6,8-difluoro-1,4-dihydro-4-oxoquinoline-3-carboxylic acid

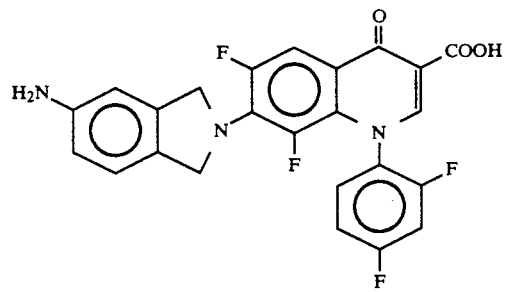

178 mg of 1-(2,4-difluorophenyl)-6,7,8-trifluoro-1,4-dihydro-4-oxoquinoline-3-carboxylic acid, 81 mg of 5-aminoisoindoline, 137 mg of DBU, and 1.5 ml of anhydrous DMF were processed in the same manner as in Example 20 to produce 47 mg of the target compound.

Melting Point: above 300° C.

$^1$H-NMR (CDCl$_3$) δ:8.47 (1H, s, C$_2$—H), 7.93 (1H, d, J=13Hz, C$_5$—H), 6.50–7.60 (6H, m, ARM-H), 4.98 (4H, brs, 2 x —CH$_2$N—)

Example 80

7-(4-hydroxy-2-isoindolinyl)-1-(4-fluorophenyl)-6,8-difluoro-1,4-dihydro-4-oxoquinoline-3-carboxylic acid

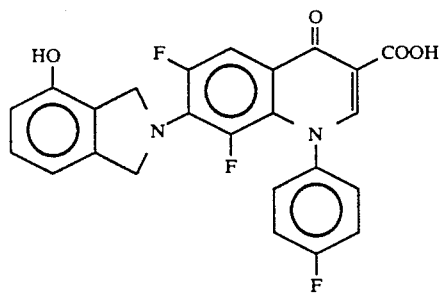

178 mg of 1-(4-fluorophenyl)-6,7,8-trifluoro-1,4-dihydro-4-oxoquinoline-3-carboxylic acid, 130 mg of 4-hydroxyisoindoline hydrobromide, 137 mg of DBU, and 1.5 ml of anhydrous DMF were processed in the same manner as in Example 20 to produce 56 mg of the target compound.

Melting Point: above 300° C.

Example 81

7-(4-methoxy-2-isoindolinyl)-1-(4-fluorophenyl)-6,8-difluoro-1,4-dihydro-4-oxoquinoline-3-carboxylic acid

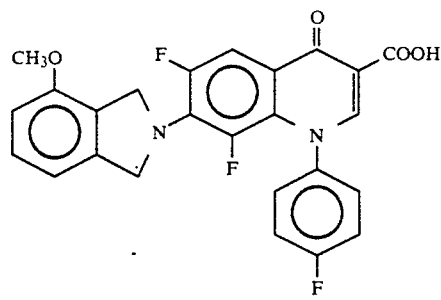

170 mg of 1-(4-fluorophenyl)-6,7,8-trifluoro-1,4-dihydro-4-oxoquinoline-3-carboxylic acid, 90 mg of 4-methoxyisoindoline, 137 mg of DBU, and 1.5 ml of anhydrous DMF were processed in the same manner as in Example 20 to produce 77 mg of the target compound.

Melting Point: 278°-284° C.

Example 82

7-(4-methoxy-2-isoindolinyl)-1-(2,4-difluorophenyl)-6,8-difluoro-1,4-dihydro-4-oxoquinoline-3-carboxylic acid

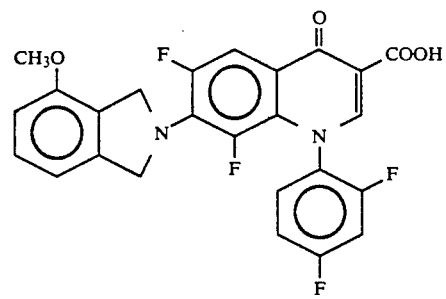

178 mg of 1-(2,4-difluorophenyl)-6,7,8-trifluoro-1,4-dihydro-4-oxoquinoline-3-carboxylic acid, 90 mg of 4-methoxyisoindoline, 137 mg of DBU, and 1.5 ml of anhydrous DMF were processed in the same manner as in Example 20 to produce 75 mg of the target compound.

Melting Point: 262°-271° C.

Example 83

7-(4-chloro-2-isoindolinyl)-1-(4-fluorophenyl)-6,8-difluoro-1,4-dihydro-4-oxoquinoline-3-carboxylic acid

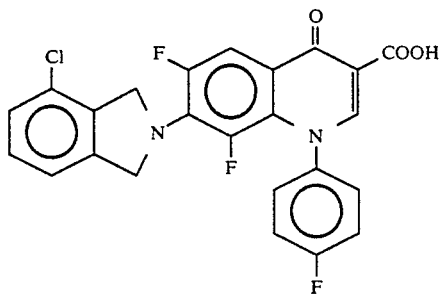

170 mg of 1-(4-fluorophenyl)-6,7,8-trifluoro-1,4-dihydro-4-oxoquinoline-3-carboxylic acid, 260 mg of 4-chloroisoindoline, and 1.5 ml of anhydrous DMF were processed in the same manner as in Example 20 to produce 82 mg of the target compound.

Melting Point: 283°-291° C.

Example 84

7-(4-chloro-2-isoindolinyl)-1-(2,4-difluorophenyl)-6,8-difluoro-1,4-dihydro-4-oxoquinoline-3-carboxylic acid

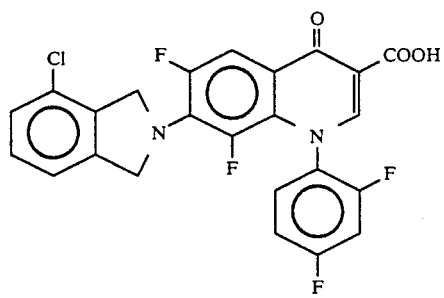

178 mg of 1-(2,4-difluorophenyl)-6,7,8-trifluoro-1,4-dihydro-4-oxoquinoline-3-carboxylic acid, 89 mg of 4-chloroisoindoline, 137 mg of DBU, and 1.5 ml of anhydrous DMF were processed in the same manner as in Example 20 to produce 60 mg of the target compound.

Melting Point: 256°-260° C.

Example 85

7-(5-chloro-2-isoindolinyl)-1-(4-fluorophenyl)-6,8-difluoro-1,4-dihydro-4-oxoquinoline-3-carboxylic acid

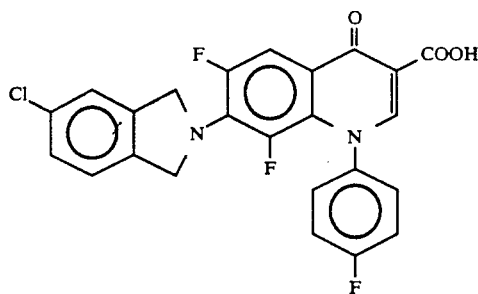

170 mg of 1-(4-fluorophenyl)-6,7,8-trifluoro-1,4dihydro-4-oxoquinoline-3-carboxylic acid, 260 mg of 5-chloroisoindoline, and 1.5 ml of anhydrous DMF were processed in the same manner as in Example 20 to produce 154 mg of the target compound.

Melting Point: above 300° C.

Example 86

7(5-chloro-2-isoindolinyl)-1-(2,4-difluorophenyl)-6,8-difluoro-1,4-dihydro-4-oxoquinoline-3-carboxylic acid

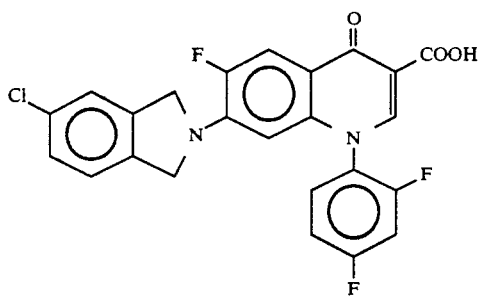

178 mg of 1-(2,4-difluorophenyl)-6,7,8-trifluoro-1,4-dihydro-4-oxoquinoline-3-carboxylic acid, 89 mg of 5-chloroisoindoline, 137 mg of DBU, and 1.5 ml of anhydrous DMF were processed in the same manner as in Example 20 to produce 25 mg of the target compound.

Melting Point: 242°–247° C.

Example 87

7-(5-methoxycarbonyl-2-isoindolinyl)-1-(4-fluorophenyl)-6,8-difluoro-1,4-dihydro-4-oxoquinoline-3-carboxylic acid

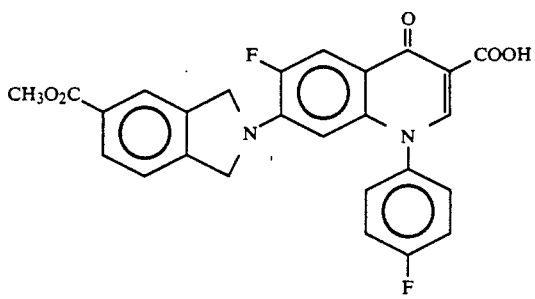

170 mg of 1-(4-fluorophenyl)-6,7,8-trifluoro-1,4-dihydro-4-oxoquinoline-3-carboxylic acid, 109 mg of 5-methoxycarbonylisoindoline hydrochloride, 228 mg of DBU, and 1.5 ml of anhydrous DMF were processed in the same manner as in Example 20 to produce 24 mg of the target compound.

Melting Point: 236°–240° C.

Example 88

7-(5-methoxycarbonyl-2-isoindolinyl]-1-(2,4-difluorophenyl)-6,8-difluoro-1,4-dihydro-4-oxoquinoline-3-carboxylic acid

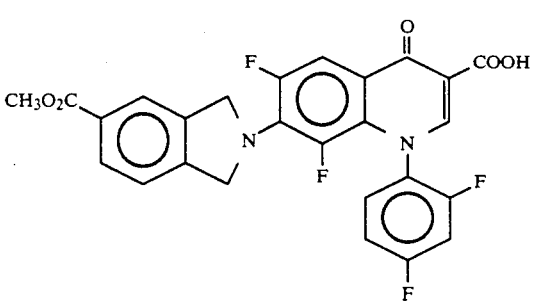

180 mg of 1-(2,4-difluorophenyl)-6,7,8-trifluoro-1,4-dihydro-4-oxoquinoline-3-carboxylic acid, 109 mg of 5-methoxycarbonylisoindoline hydrochloride, 228 mg of DBU, and 1.5 ml of anhydrous DMF were processed in the same manner as in Example 20 to produce 52 mg of the target compound.

Melting Point: 248°–251° C.

Example 89

7-(4-methoxycarbonyl-2-isoindolinyl)-1-(2,4-difluorophenyl)-6,8-difluoro-1,4-dihydro-4-oxoquinoline-3-carboxylic acid

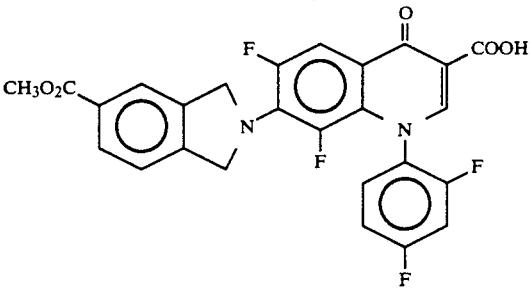

180 mg of 1-(2,4-fluorophenyl)-6,7,8-trifluoro-1,4-dihydro-4-oxoquinoline-3-carboxylic acid, 109- mg of 5-methoxycarbonylisoindoline hydrochloride, 228 mg of DBU, and 1.5 ml of anhydrous DMF were processed in the same manner as in Example 20 to produce 108 mg of the target compound.

Melting Point: 291°–296° C. (decomposed)

Example 90

7-(4-methoxycarbonyl-2-isoindolinyl)-1-(4-fluorophenyl)-6,8-difluoro-1,4-dihydro-4-oxoquinoline-3-carboxylic acid

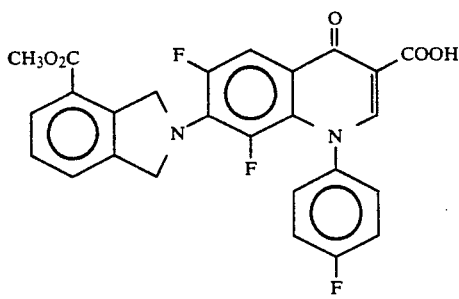

170 mg of 1-(4-fluorophenyl)-6,7,8-trifluoro-1,4-dihydro-4-oxoquinoline-3-carboxylic acid, 109 mg of 4-methoxycarbonylisoindoline hydrochloride, 228 mg of DBU, and 1.5 ml of anhydrous DMF were processed in the same manner as in Example 20 to produce 65 mg of the target compound.

Melting Point: 283°–287° C.

Example 91

7-(5-methoxycarbonyl-2-isoindolinyl)-1-ethyl-6-fluoro-1,4-dihydro-4-oxoquinoline-3-carboxylic acid

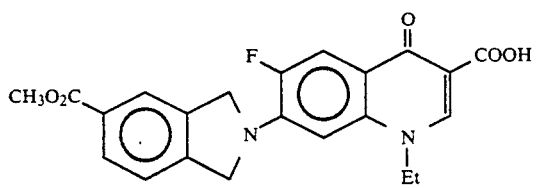

128 mg of 1-ethyl-6,7-difluoro-1,4-dihydro-4-oxoquinoline-3-carboxylic acid, 109 mg of 5-methoxycarbonylisoindoline hydrochloride, 228 mg of DBU, and 1.5 ml of anhydrous DMF were processed in the same manner as in Example 20 to produce 104 mg of the target compound.

Melting Point: above 300° C.

$^1$H-NMR (DMSO-$d_6$) δ:8.92 (1H, s, $C_2$—H), 7.58 (1H, d, J=7Hz, $C_8$—H), 6.80–8.05 (4H, m, $C_5$—H, ARM-H), 5.08 (4H, s, 2 x —CH$_2$N—), 4.58 (2H, q, J=7Hz, —C$\underline{H}_2$CH$_3$), 3.88 (3H, s, OCH$_3$), 1.48 (3H, t, J=7Hz, —CH$_2$C$\underline{H}_3$)

Example 92

7-(5-methoxycarbonyl-2-isoindolinyl)-1-cyclopropyl-6-fluoro-1,4-dihydro-4-oxoquinoline-3-carboxylic acid

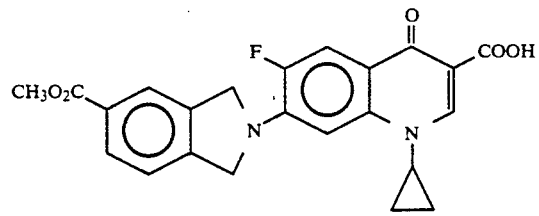

133 mg of 1-cyclopropyl-6,7-difluoro-1,4-dihydro-4-oxoquinoline-3-carboxylic acid, 109 mg of 5-methoxycarbonylisoindoline hydrochloride, 228 mg of DBU, and 1.5 ml of anhydrous DMF were processed in the same manner as in Example 20 to produce 74 mg of the target compound.

Melting Point: 279°–285° C.

$^1$H-NMR (DMSO-$d_6$) δ:8.62 (1H, s, $C_2$—H), 7.60 (1H, d, J=7Hz, $C_8$—H), 7.20–8.10 (4H, m, $C_5$—H, ARM-H), 5.10 (4H, brs, 2 x —CH$_2$N—), 3.85 (3H, s, OCH$_3$), 3.82 (1H, m,

), 1.10–1.40 (4H, m,

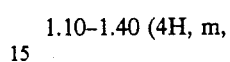

)

Example 93

7-(5-methoxycarbonyl-2-isoindolinyl)-1-ethyl-6,8-difluoro-1,4-dihydro-4-oxoquinoline-3-carboxylic acid

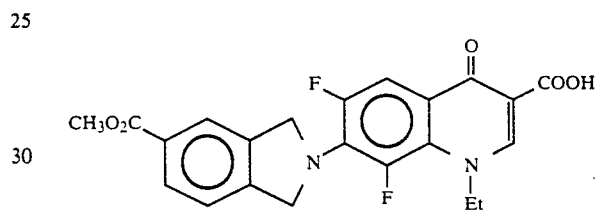

271 mg of 1-ethyl-6,7,8-trifluoro-1,4-dihydro-4-oxoquinoline-3-carboxylic acid, 217 mg of 5-methoxycarbonylisoindoline hydrochloride, 457 mg of DBU, and 3ml of anhydrous DMF were processed in the same manner as in Example 20 to produce 122 mg of the target compound.

Melting Point: 264°–267° C.

$^1$H-NMR (DMSO-$d_6$) δ:8.63 (1H, s, $C_2$—H), 7.30–8.10 (4H, m, $C_5$—H, ARM-H), 5.25 (4H, s, 2 x —CH$_2$N—), 4.5 (2H, q, J=7Hz, —C$\underline{H}_2$CH$_3$), 3.95 (3H, s, OCH$_3$), 1.60 (3H, t, J=7Hz, —CH$_2$C$\underline{H}_3$)

Example 94

10-(5-methoxycarbonyl-2-isoindolinyl)-9-fluoro-2,3-dihydro-3-methyl-7-oxo-7H-pyrido[1,2,3-de][1,4]-benzoxazine-6-carboxylic acid

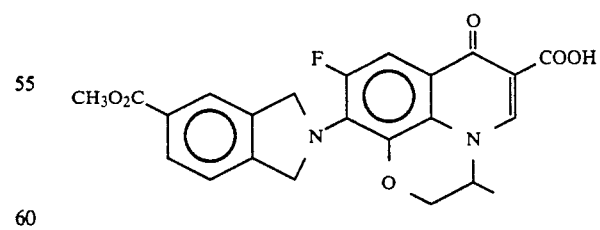

142 mg of 9,10-difluoro-2,3-dihydro-3-methyl-7-oxo-7H-pyrido[1,2,3-de][1,4]-benzoxazine-6-carboxylic acid, 109 mg of 5-methoxycarbonylisoindoline hydrochloride, 228 mg of DBU, and 1.5 ml of anhydrous DMF were processed in the same manner as in Example 20 to produce 45 mg of the target compound.

Melting Point: 257°–262° C.

Example 95

7-(4-methoxycarbonyl-2-isoindolinyl)-1-cyclopropyl-5-amino-6,8-difluoro-1,4-dihydro-4-oxoquinoline-3-carboxylic acid

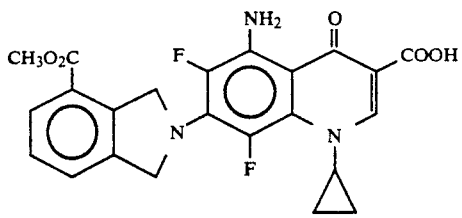

298 mg of 1-cyclopropyl-5-amino-6,7,8-trifluoro-1,4-dihydro-4-oxoquinoline-3-carboxylic acid, 257 mg of 4-methoxycarbonylisoindoline hydrochloride, 532 mg of DBU, and 2ml of anhydrous DMF were processed in the same manner as in Example 20 to produce 181 mg of the target compound.

Melting Point: 268°-272° C. (decomposed)

$^1$H-NMR (CDCl$_3$—CF$_3$COOD, 10 : 1) δ: 8.90 (1H, s, C$_2$—H), 7.47-8.06 (3H, m, ARM-H), 5.62 and 5.34 (each 2H, brs, 2 x —CH$_2$N—), 4.19 (1H, m,

4.01 (3H, s, —COOCH$_3$), 1.21-1.41 (4H, m,

Example 96

7-(5-hydroxymethyl-2-isoindolinyl)-1-cyclopropyl-5-amino-6,8-difluoro-1,4-dihydro-4-oxoquinoline-3-carboxylic acid

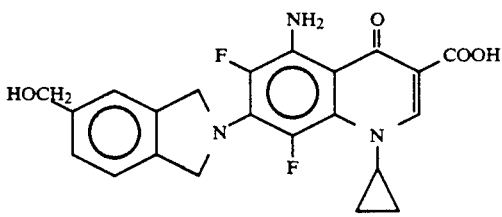

298 mg of 1-cyclopropyl-5-amino-6,7,8-trifluoro-1,4-dihydro-4-oxoquinoline-3-carboxylic acid, 179 mg of 5-hydroxymethylisoindoline, 304 mg of DBU, and 2 ml of anhydrous DMF were processed in the same manner as in Example 20 to produce 106 mg of the target compound.

Melting Point: 237°-240° C. (decomposed)

$^1$H-NMR (DMSO-d$_6$) δ: 8.48 (1H, s, C$_2$—H) 7.23-7.42 (5H, m, ARM-H, —NH$_2$), 5.08 (4H, brs, 2 x —CH$_2$N—), 4.52 (2H, d, J=5H/, —CH$_2$OH), 4.01 (1H, m,

1.08-1.12 (4H, m,

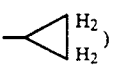

Example 97

7-(5-hydroxymethyl-2-isoindolinyl)-1-cyclopropyl-6 8-difluoro-1,4-dihydro-4-oxoquinoline-3-carboxylic acid

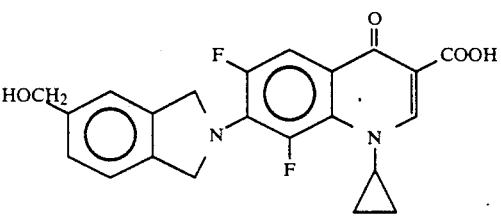

283 mg of 1-cyclopropyl-6,7,8-trifluoro-1,4- dihydro-4-oxoquinoline-3-carboxylic acid, 179 mg of 5-hydroxymethylisoindoline, 304 mg of DBU, and 2 ml of anhydrous DMF were processed in the same manner as in Example 20 to produce 140 mg of the target compound.

Melting Point: 262°-266° C. (decomposed)

$^1$H-NMR (DMSO-d$_6$) δ: 8.63 (1H, s, C$_2$—H), 7.77 (1H, d, J=14H$_z$, C$_5$—H), 7.77-7.34 (3H, m, ARM-H), 5.14 (4H, brs, 2 x —CH$_2$N—), 4.52 (2H, brs, —CH$_2$OH), 4.13 (1H, m,

1.21 (4H, brs,

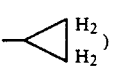

Example 98

10-(5-hydroxymethyl-2-isoindolinyl)-9-difluoro-2,3-dihydro-3-methyl-7-oxo-7H-pyrido[1,2,3-de][1,4]-benzoxazine-6-carboxylic acid

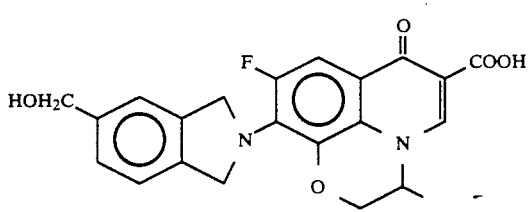

281 mg of 9,10-difluoro-2,3-dihydro-3-methyl-7-oxo-7H-pyrido[1,2,3,-de][1,4]-benzoxazine-6-carboxylic acid, 179 mg of 5-hydroxymethylisoindoline, 304 mg of DBU, and 2 ml of anhydrous DMF were processed in the same manner as in Example 20 to produce 75 mg of the target compound.

Melting Point: 248°–252° C. (decomposed) ¹H-NMR (DMSO-d₆) δ: 8.95 (1H, s, C₅—H), 7.62 (1H, d, J=14Hz, C₈—H), 7.25–7.32 (3H, m, ARM-H), 4.90–5.25 (6H, m, 2 x —CH₂N—, C₃—H, —OH), 4.34–4.68 (4H, m, —CH₂OH, C₂—H), 1.50 (3H, brs, CH₃)

Example 99

7-(4-hydroxymethyl-2-isoindolinyl)-1-cyclopropyl-5-amino-6,8-difluoro-1,4-dihydro-4-oxoquinoline-3-carboxylic acid

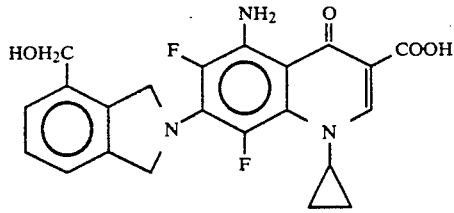

298 mg of 1-cyclopropyl-5-amino-6,7,8-trifluoro-1,4-dihydro-4-oxoquinoline-3-carboxylic acid, 179 mg of 4-hydroxymethylisoindoline, 304 mg of DBU, and 2 ml of anhydrous DMF were processed in the same manner as in Example 20 to produce 250 mg of the target compound.

Melting Point: 252°–255° C. (decomposed)

¹H-NMR (DMSO-d₆) δ: 8.47 (1H, s, C₂—H), 7.28 (3H, brs, ARM-H), 7.21 (2H, brs, —NH₂), 5.23 (1H, t, J=5Hz, OH), 5.10 (4H, brs, 2 x —CH₂N—), 4.52 (2H, d, J=5Hz, —CH₂OH), 4.01 (1H, m,

1.08 (4H, m,

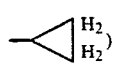

Example 100

7-(4-hydroxymethyl-2-isoindolinyl)-1-cyclopropyl-6,8-difluoro-1,4-dihydro-4-oxoquinoline-3-carboxylic acid

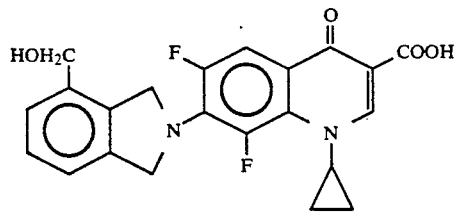

283 mg of 1-cyclopropyl-6,7,8-trifluoro-1,4-dihydro-4-oxoquinoline-3-carboxylic acid, 179 mg of 4-hydroxymethylisoindoline, 304 mg of DBU, and 2 ml of anhydrous DMF were processed in the same manner as in Example 20 to produce 170 mg of the target compound.

Melting Point: 223°–227° C. (decomposed) 1H-NMR (DMSO-d₆) δ: 8.64 (1H, s, C₂—H), 7.79 (1H, d, J=14Hz, C₅—H), 7.30 (3H, m, ARM-H), 5.24 (1H, t, J=5Hz, OH), 5.16 (4H, brs, 2 x —CH₂N—), 4.53 (2H, d, J=5Hz, —CH₂OH), 4.13 (1H, m,

1.20 (4H, m,

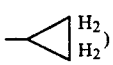

Example 101

10-(4-hydroxymethyl-2-isoindolinyl)-9-fluoro-2,3-dihydro-3-methyl-7-oxo-7H-pyrido [1,2,3-de][1,4]-benzoxazine-6-carboxylic acid

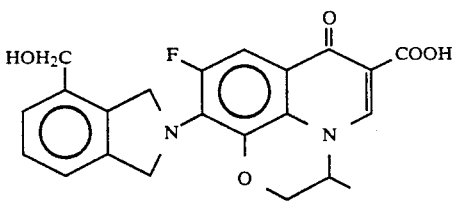

281 mg of 9,10-difluoro-2,3-dihydro-3-methyl-7-oxo-7H-pyrido [1,2,3-de][1,4]-benzoxazine-6-carboxylic acid, 179 mg of 4-hydroxymethylisoindoline, 304 mg of DBU, and 2 ml of anhydrous DMF were processed in the same manner as in Example 20 to produce 120 mg of the target compound.

Melting Point: 205°–209° C. (decomposed)

¹H-NMR (DMSO-d₆) δ: 8.95 (1H, s, C₅—H), 7.62 (1H, d, J=14Hz, C₈—H), 7.27 (3H, brs, ARM-H), 4.91–5.21 (6H, m, 2 x —CH₂N—, C₃—H, OH), 4.34–4.64 (4H, m, —CH₂OH, C₂—H), 1.49 (3H, J=7Hz, CH₃)

Example 102

7-(4-aminomethyl-2-isoindolinyl)-1-cyclopropyl-6,8-difluoro-1,4-dihydro-4-oxoquinoline-3-carboxylic acid

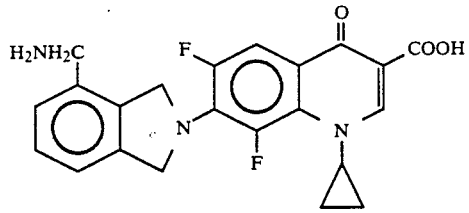

(1) 283 mg of 1-cyclopropyl-6,7,8-trifluoro-1,4-dihydro-4-oxoquinoline-3-carboxylic acid, 300 mg of 4-(t-butyloxycarbonylaminomethyl)isoindoline, 300 mg of DBU, and 2 ml of anhydrous DMF were processed in the same manner as in Example 20 to produce 300 mg of 7-[4-(t-butyloxycarbonyl aminomethyl)-2-isoindolinyl]-1-cyclopropyl-6,8-difluoro-1,4-dihydro-4-oxoquinoline-3-carboxylic acid.

(2) 140 mg of [4-(t-butyloxycarbonylaminomethyl)-2-isoindolinyl]-1-cyclopropyl-6,8-difluoro-1,4-dihydro-4-oxoquinoline-3-carboxylic acid was added to 10 ml of 4 N hydrochloric acid - acetic acid solution, and stirred at room temperature for 10 minutes. After the solution was concentrated under reduced pressure, methanol was added to it. The solution was evaporated twice under reduced pressure to remove excessive hydrochloric acid. The residue was recrystallized from ethanol to obtain 97 mg of 7-(4-aminomethyl-2-isoindolinyl)-1-cyclopropyl-6,8-difluoro-1,4-dihydro-4-oxoquinoline-3-carboxylic acid hydrochloride.

Melting Point: 243°-247 °C. (decomposed) $^1$H-NMR (DMSO-$d_6$) δ: 8.67 (1H, s, $C_2$—H), 7.84 (1H, d, J=15$H_z$, $C_5$—H), 7.44 (3H, brs, ARM-H), 5.21 and 5.29 (each 2H, brs, 2 x —$CH_2$N—), 4.15 (1H, m,

4.04 (2H, brs, C$\underline{H}_2$NH$_2$), 1.23 (4H, m,

Example 103

7-(5-aminomethyl-2-isoindolinyl)-1-cyclopropyl-6,8-difluoro-1,4-dihydro-4-oxoquinoline-3-carboxylic acid

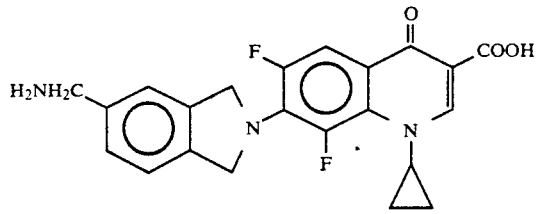

(1) 283 mg of 1-cyclopropyl-6,7,8-trifluoro-1,4-dihydro-4-oxoquinoline-3-carboxylic acid, 325 mg of 5-acetamidomethylisoindoline hydrobromide, 536 mg of DBU, and 2 ml of anhydrous DMF were processed in the same manner as in Example 20 to produce 154 mg of 7-(5-acetamidomethyl-2-isoindolinyl)-1-cyclopropyl-6,8-difluoro-1,4-dihydro-4-oxoquinoline-3-carboxylic acid. $^1$H-NMR (CDCl$_3$) δ: 8.74 (1H, s, $C_2$—H), 7.89 (1H, d, J=14$H_z$, $C_5$—H), 7.26-7.30 (3H, brs, ARM-H), 5.15 (4H, brs, 2 x —$CH_2$N—), 4.47 (2H, d, J=6$H_z$, C$\underline{H}_2$NH$_2$), 4.00 (1H, m,

2.06 (3H, s, —COCH$_3$), 1.17-1.31 (4H, m,

(2) 130 mg of 7-(5-acetamidomethyl-2-isoindolinyl)-1-carboxylic-6,8-difluoro-1,4-dihydro-4-oxoquinoline-3-carboxylic acid was added to a mixed solution of 6 ml of concentrated HCl, 1 ml of water, and 2 ml of ethanol, and the mixture was refluxed under heating for 18 hours. After the mixture was concentrated under reduced pressure, the residue was recrystallized from ethanol to obtain 56 mg of 7-(5-aminomethyl-2-isoindolinyl)-1-cyclopropyl-6,8-difluoro-1,4-dihydro-4-oxoquinoline-3-carboxylic acid hydrochloride.

Melting Point: 270°-274° C. (decomposed)

$^1$H-NMR (DMSO-$d_6$) δ: 8.66 (1H, s, $C_2$—H), 7.81 (1H, d, J=14$H_z$, $C_5$—H), 7.46°-7.51 (3H, m, ARM-H), 5.16 (4H, brs, 2 x —$CH_2$N—), 4.15 (1H, m,

4.06 (2H, s, C$\underline{H}_2$NH$_2$), 1.20-1.22 (4H, m,

Example 104

10-(5-aminomethyl-2-isoindolinyl)-9-fluoro-2,3-dihydro-3-methyl-7-oxo-7H-pyrido [1,2,3-de][1,4]-benzoxazine-6-carboxylic acid

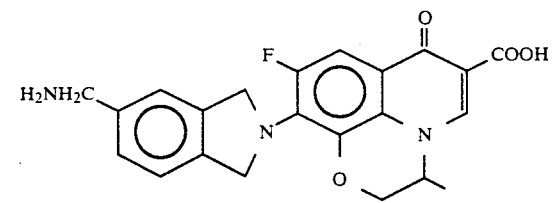

(1) 422 mg of 9,10-difluoro-2,3-dihydro-3methyl-7-oxo-7H-pyrido[1,2,3-de][1,4]-benzoxazine-6-carboxylic acid, 490 mg of 5-acetamidomethylisoindoline hydrobromide, 795 mg of DBU, and 3 ml of anhydrous DMF were processed in the same manner as in Example 20 to produce 382 mg of 10-(5-acetamidomethyl-2-isoindolinyl)-9-fluoro-2,3-dihydro-3-methyl-7-oxo-7H-pyrido[1,2,3-de][1,4]-benzoxazine-6-carboxylic acid.

(2) 315 mg of 10-(5-acetamidomethyl-2-isoindolinyl)-9-fluoro-2,3-dihydro-3-methyl-7-oxo-7H-pyrido[1,2,3-de][1,4]-benzoxazine-6carboxylic acid was added to a mixed solution of 12 ml of concentrated HCl, 2.5 ml of water, and 5 ml of ethanol, and the mixture was heated under reflux for 15 hours. After the mixture was concentrated under reduced pressure, the residue was recrystallized from ethanol to obtain 170 mg of 10-(5-aminomethyl-2-isoindolinyl)-9-fluoro-2,3-dihydro-3-methyl-7-oxo-7H-pyrido[1,2,3-de]1,4]-benzoxazine-6-carboxylic acid.

Melting Point: above 300° C. $^1$H-NMR (DMSO-$d_6$) δ: 8.96 (1H, s, $C_5$—H), 8.37 (2H, brs, NH$_2$), 7.63 (1H, d, J=14$H_z$, $C_8$—H), 7.43-7.49 (3H, m, ARM-H), 4.95-5.15 (5H, m, 2 x —$CH_2$N—, $C_3$—H), 4.35-4.65 (2H, m, $C_2$—H), 4.05 (2H, brs, —C$\underline{H}$HD 2 NH$_2$), 1.48 (3H, J=7$H_z$, CH$_3$)

Example 105

7-(5-aminomethyl-2-isoindolinyl)-1-cyclopropyl-6-fluoro-1,4- dihydro-4-oxoquinoline-3-carboxylic acid carboxylic acid.

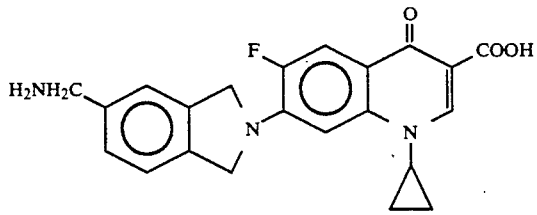

(1) 398 mg of 1-cyclopropyl-6,7-difluoro-1,4-dihydro-4-oxoquinoline-3-carboxylic acid, 490 mg of 5-acetamidomethylisoindoline hydrobromide, 795 mg of DBU, and 3 ml of anhydrous DMF were processed in the same manner as in Example 20 to produce 485 mg of 7-(5-acetamidomethyl-2-isoindolinyl)-1-cyclopropyl-6-fluoro-1,4-dihydro-4-oxoquinoline-3-carboxylic acid.

(2) 304 mg of 7-(5-acetamidomethyl-2-isoindolinyl)-1-cyclopropyl-6--fluoro-1,4-dihydro--4-oxoquinoline-3-carboxylic acid was added to a mixed solution of 12 ml of concentrated HCl, 2.5 ml of water, and 5 ml of ethanol, and the mixture was heated under reflux for 15 hours. After cooling under atmosphere, the crystals deposited were collected by filtration and washed with ethanol to obtain 264 mg of 7-(5-aminomethyl-2-isoindolinyl)-1-cyclopropyl-6-fluoro-1,4-dihydro-4-oxoquinoline-3-carboxylic acid hydrochloride.

Melting Point: 248°-251° C. (decomposed)

$^1$H-NMR (DMSO-d$_6$) δ: 8.61 (1H, s, C$_2$—H), 8.44 (2H, brs, NH$_2$), 7.89 (1H, d, J=14H$_z$, C$_5$—H), 7.49-7.55 (3H, m, ARM-H), 7.24 (1H, d, J=8H$_z$, C$_8$—H), 5.04 (4H, brs, 2 x —CH$_2$N—), 4.07 (2H, brs, CH$_2$NH$_2$), 1.19-1.38 (4H,

Example 106

7-(5-aminomethyl-2-isoindolinyl)-1-cyclopropyl-5-amino-6,8-difluoro-1,4-dihydro-4-oxoquinoline-3-carboxylic acid

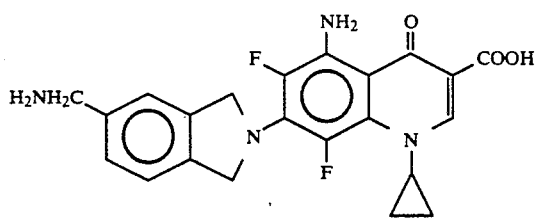

(1) 447 mg of 1-cyclopropyl-5-amino-6,7,8-trifluoro-1,4-dihydro-4-oxoquinoline-3-carboxylic acid, 490 mg of 5-acetamidomethylisoindoline hydrobromide, 795 mg of DBU, and 3 ml of anhydrous DMF were processed in the same manner as in Example 20 to produce 436 mg of 7-(5-acetamidomethyl-2-isoindolinyl)-1-cyclopropyl-5-amino-6,8-difluoro-1,4-dihydro-4-oxoquinoline-3-carboxylic acid.

(2) 327 mg of 7-(5-acetamidomethyl-2-isoiniolinyl)-1-cyclopropyl-5-amino-6,8-difluoro-1,4-dihydro-4-oxoquinoline-3-carboxylic acid was added to a mixed solution of 12 ml of concentrated HCl, 2.5 ml of water, and 5 ml of ethanol, and the mixture was heated under reflux for 19 hours. After the mixture was concentrated under reduced pressure, the residue was recrystallized from ethanol to obtain 62 mg of 7-(5-aminomethyl-2-isoindolinyl)-1-cyclopropyl-5-amino-6,8-difluoro-1,4-dihydro-4-oxoquinoline-3-carboxylic acid hydrochloride.

Melting Point: 253°-257° C. (decomposed)

$^1$H-NMR (DMSO-d$_6$) δ: 8.46 (1H, s, C$_2$—H), 8.45 (4H, brs, 2 x NH$_2$), 7.47-7.53 (3H, m, ARM-H), 4.98 (4H, brs 2 x —CH$_2$N—), 4.06 (2H, m, CH$_2$NH$_2$), 1.11-1.36 (4H, m,

Example 107

7-(2-isoindolinyl)-1-cyclopropyl-6-fluoro-1,4-dihydro-4-oxo-1,8-naphthyridine-3-carboxylic acid

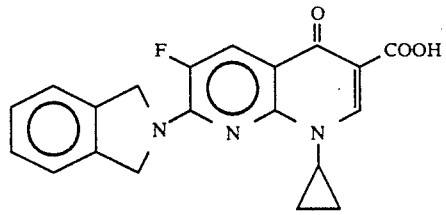

(1) A mixture of 310 mg of 1-cyclopropyl-(-fluoro-7-chloro-1,4-dihydro-4-oxo-1,8-naphthyridine-3-carboxylic acid ethylester, 600 mg of isoindoline, and 5 ml of anhydrous chloroform was heated at 60°-70° C. for 0.5 hours while stirring. The resulting reaction mixture was diluted with 25 ml of chloroform. The mixture was washed with 5% acetic acid and brine in this order, dried over anhydrous sodium sulfate, and condensed. The residue was crystallized by the addition of hot ethanol. After cooling the mixture, the crystals were collected by filtration and recrystallized from a mixed solvent of chloroform, methanol, and ethanol to give 215 mg of 7-(2-isoindolinyl)-1-cyclopropyl-6-fluoro-1,4-dihydro-4-oxo-1,8-naphthyridine-3-carboxylic acid ethyl ester.

(2) 150 mg of 7-(2-isoindolinyl)-1-cyclopropyl-6-fluoro-1,4-dihydro-4-oxo-1,8-naphthyridine-3-carboxylic acid ethyl ester was dissolved in a mixture of 10 ml of 10% hydrochloric acid and 10 ml of ethanol. The mixture was heated under reflux for 2 hours. The precipitates deposited were collected by filteration, and washed with water and ethanol in this order to obtain 107 mg of 7-(2- isoindolinyl)-1-cyclopropyl-6-fluoro-1,4-dihydro-4-oxo-1,8- naphthyridine-3-carboxylic acid.

Melting point: above 300° C.

$^1$H-NMR (DMSO-d$_6$) δ: 8.62 (1H, s, C$_2$—H), 8.06 (1H, d, C$_5$—H), 7.3-7.55 (4H, m, ARM-H), 5.20 (4H, brs, 2 x—CH$_2$N—), 3.83 (1H. m,

1.10–1.40(4H, m,

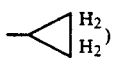

Example 108

7-(4-amino-2-isoindolinyl)-1-cyclopropyl-6-fluoro-1,4-dihydro-4-oxo-1,8-naphthyridine-3-carboxylic acid

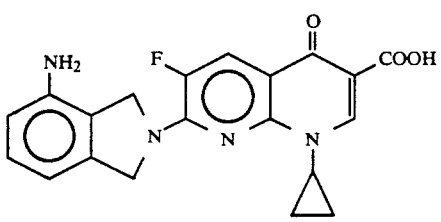

310 mg of 1 cyclopropyl-6-fluoro-7-chloro-1,4-dihydro-4-oxo-1,8-naphthyridine-3-carboxylic acid ethyl ester, 270 mg of 4-aminoisoindoline, 0.42 ml of triethylamine, and 5 ml of anhydrous chloroform were processed in a similar manner as in Example 107 to produce 88 mg of 7-(4-amino-2- isoindolinyl)-1-cyclopropyl-6-fluoro-1,4-dihydro-4-oxo-1,8- naphthyridine-3-carboxylic acid.

Melting point: above 300° C.

$^1$H-NMR (DMSO-$d_6$) δ: 8.62 (1H, s, $C_2$—H), 8.06 (1H, d, $C_5$—H), 6.78–7.25 (3H, m, ARM-H), 5.2 (4H, brs, 2 x—$CH_2$N—), 3.83 (1H. m,

1.10–1.40 (4H, m,

Example 109

7-(4-chloro-2-isoindolinyl)-1-cyclopropyl-6-flurro-1,4-dihydro-4-oxo-1,8-naphthyridine-3-carboxylic acid

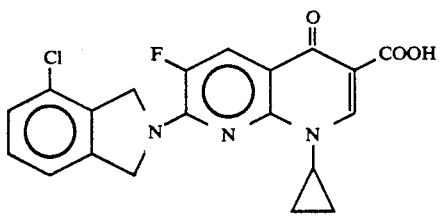

310 mg of 1-cyclopropyl-6-fluoro-7-chloro-1,4-dihydro-4- oxo-1,8-naphthyridine-3-carboxylic acid ethyl ester, 660 mg of 4-chloroisoindoline, 0.42 ml of triethylamine, and 5 ml of anhydrous chloroform were processed in the same manner as in Example 107 to produce 75 mg of 7-(4-chloro-2- isoindolinyl)-1-cyclopropyl-6-fluoro-1,4-dihydro-4-oxo-1,8- naphthyridine-3-carboxylic acid.

Melting point: above 300° C.

$^1$H-NMR (DMSO-$d_6$) δ: 8.68 (1H, s, $C_2$—H), 8.06 (1H, d, $C_5$—H), 7.45–7.55 (3H, m, ARM-H), 5.3 (4H, br, s, 2 x—$CH_2$N—), 3.83 (1H. m,

1.10–1.40 (4H, m,

Example 110

7-(4-aminomethyl-2-isoindolinyl)-1-cyclopropyl-6-fluoro-1,4-dihydro-4-oxo-1,8-naphthyridine-3-carboxylic acid

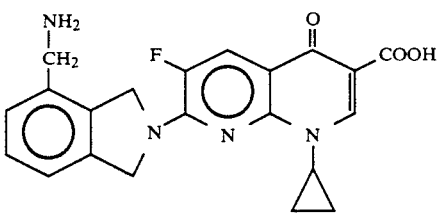

(1) A mixture of 310 mg of 1-cyclopropyl-6-fluoro-7-chloro-1,4-dihydro-4-oxo-1,8-naphthyridine-3-carboxylic acid ethyl ester, 524 mg of 4-(t-butyloxycarbonylaminomethyl)isoindoline, 0.42 ml of triethylamine, and 5 ml of anhydrous chloroform was heated at 60°–70° C. for 0.5 hours while stirring. The resulting reaction mixture was diluted with 25 ml of chloroform. The mixture was washed with 5% acetic acid and brine in this order, dried over anhydrous sodium sulfate, and condensed. The residue was crystallized by the addition of ethylether. The crystals were collected by filtration and recrystallized from a mixed solvent of chloroform, methanol, and ethanol to obtain 417 mg of 7-[4- (t-butoxycarbonylaminomethyl)-2-isoindolinyl]-1-cyclopropyl-6-fluoro-1,4-dihydro-4-oxo-1,8-naphthyridine-3-carboxylic acid ethyl ester.

(2) 150 mg of 7-[4-t-butoxycarbonylaminomethyl)-2-isoindolinyl]-1-cyclopropyl-6-fluoro-1,4-dihydro-4-oxo-1,8- naphthyridine-3-carboxylic acid ethyl ester was dissolved in a mixture of 10 ml of 10% hydrochloric acid and 10 ml of ethanol. The mixture was heated under reflux for 2 hours. The precipitates deposited were collected by filteration and washed with water and ethanol in this order to obtain 94 mg of 7-(4-aminomethyl-2-isoindolinyl)-1-cyclopropyl-6-fluoro-1,4-dihydro-4-oxo-1,8-naphthyridine-3-carboxylic acid as hydrochloride salt.

Melting point: above 300° C.

$^1$H-NMR (DMSO-$d_6$) δ: 8.60 (1H, s, $C_2$—H), 8.57 (2H, brs, $NH_2$), 8.06 (1H, d, $C_5$—H), 7.40–7.60 (3H, m, ARM-H), 5.25 (4H, br, 2 x —$CH_2$N—), 4.08 (2H, m, —$CH_2NH_2$), 3.83 (1H, m,

1.10–1.40 (4H, m,

Example 111

7-(5-aminomethyl-2-isoindolinyl)-1-cyclopropyl-6-fluoro-1,4-dihydro-4-oxo-1,8-naphthyridine-3-carboxylic acid

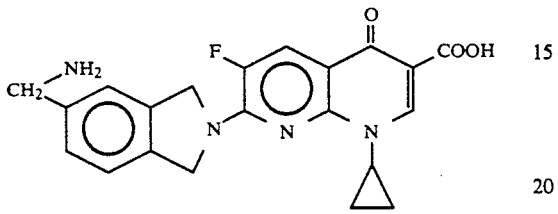

(1) A mixture of 310 mg of 1-cyclopropyl-6-fluoro-7-chloro-1,4-dihydro-4-oxo-1,8-naphthyridine-3-carboxylic acid ethyl ester, 745 mg of 5-acetamidomethylisoindoline, 0.56 ml of triethylamine, and 5 ml of anhydrous chloroform was heated at 60°–70° C. for 0.5 hours while stirring. The resulting reaction mixture was diluted with 25 ml of chloroform. The mixture was washed with 5% acetic acid and brine in this order, dried over anhydrous sodium sulfate, and condensed. The residue was crystallized by the addition of ethylether. The crystals were collected by filtration and recrystallized from a mixed solvent of chloroform, methanol, and ethanol to obtain 260 mg of 7-(5- acetamidomethyl-2-isoindolinyl)-1-cyclopropyl-6-fluoro-1,4- dihydro-4-oxo-1,8-naphthyridine-3-carboxylic acid ethyl ester.

(2) 80 mg of 7-(5-acetamidomethyl-2-isoindolinyl)-1-cyclopropyl-6-fluoro-1,4-dihydro-4-oxo-1,8-naphthyridine-3-carboxylic acid ethyl ester was dissolved in a mixture of 10 ml of 10% hydrochloric acid and 10 ml of ethanol. The mixture was heated under reflux for 24 hours. The precipitates deposited were collected by filtration and washed with water and ethanol in this order to obtain 68 mg of 7-(5-aminomethyl-2-isoindolinyl)-1-cyclopropyl-6-fluoro-1,4-dihydro-4-oxo-1,8-naphthyridine-3-carboxylic acid hydrochloride salt.

Melting point: above 300° C.

$^1$H-NMR (DMSO-d$_6$) δ: 8.62 (1H, s, C$_2$—H) 8.40 (2H, m, NH$_2$), 8.06 (1H, d, C$_5$—H), 7.4–7.55 (4H, m, ARM-H), 5.2 (4H, br, s, 2 x -C$\underline{H}_2$N—), 4.08 (2H, brs, —C$\underline{H}_2$NH$_2$), 3.83 (1H. m,

1.10–1.40 (4H, m,

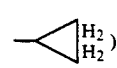

Example 112

7-(4-hydroxymethyl-2-isoindolinyl)-1-cyclopropyl-6-fluoro-1,4-dihydro-4-oxo-1,8-naphthyridine-3-carboxylic acid

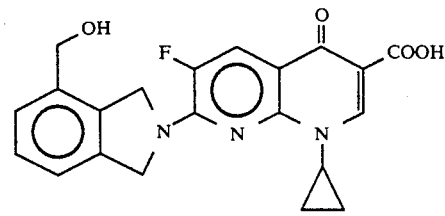

310 mg of 1-cyclopropyl-6-fluoro-7-chloro-1,4-dihydro-4- oxo-1,8-naphthyridine-3-carboxylic acid ethyl ester, 298 mg of 4-hydroxymethylisoindoline, 0.42 ml of triethylamine, and 5 ml of anhydrous chloroform were processed in a similar manner as in Example 107 to produce 75 mg of 7-(4- hydroxymethyl-2-isoindolinyl)-1-cyclopropyl-6-fluoro-1,4- dihydro-4-oxo-1,8-naphthyridine-3-carboxylic acid.

Melting point: above 300° C.

$^1$H-NMR (DMSO-d$_6$) δ: 8.62 (1H, s, C$_2$—H), 8.06 (1H, d, C$_5$—H), 7.35 (3H, brs, ARM-H), 5.08–5.32 (5H, brs, OH, 2 x—C$\underline{H}_2$N—), 4.61 (2H, brs, C$\underline{H}_2$OH) 3.78 (1H. m,

1.10–1.40 (4H, m,

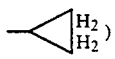

Example 113

7-(5-hydroxymethyl-2-isoindolinyl)-1-cyclopropyl-6-fluoro-1,4-dihydro-4-oxo-1,8-naphthyridine-3-carboxylic acid

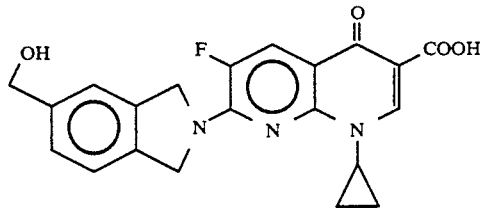

310 mg of 1-cyclopropyl-6-fluoro-7-chloro-1,4-dihydro-4- oxo-1,8-naphthyridine-3-carboxylic acid ethyl ester, 298 mg of 5-hydroxymethylisoindoline, 0.42 ml of triethylamine, and 5 ml of anhydrous chloroform were processed in a similar manner as in Example 107 to produce 88 mg of 7-(5- hydroxymethyl-2-isoindolinyl)-1-cyclopropyl-6-fluoro-1,4- dihydro-4-oxo-1,8-naphthyridine-3-carboxylic acid.

Melting point: above 300° C.

$^1$H-NMR (DMSO-d$_6$) δ: 8.62 (1H, s, C$_2$—H), 8.01 (1H, d, C$_5$—H), 7.28–7.55 (3H, m, ARM-H), 5.2 (5H, br, OH, 2 x-C$\underline{H}_2$N—), 4.55 (2H, s, C$\underline{H}_2$OH), 3.78 (1H. m, 1.10–1.40 (4H, m, 

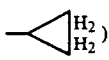)

Example 114

7-(4-methoxy-2-isoindolinyl)-1-cyclopropyl-6-fluoro-1,4-dihydro-4-oxo-1,8-naphthyridine-3-carboxylic acid

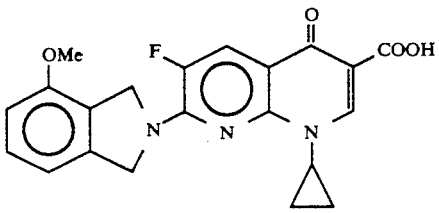

310 mg of 1-cyclopropyl-6-fluoro-7-chloro-1,4-dihydro-4-oxo-1,8-naphthyridine-3-carboxylic acid ethyl ester, 298 mg of 4-methoxyisoindoline, 0.42 ml of triethylamine, and 5 ml of anhydrous chloroform were processed in the same manner as in Example 107 to produce 118 mg of 7-(4-methoxy-2-isoindolinyl)-1-cyclopropyl-6-fluoro-1,4-dihydro-4-oxo-1,8-naphthyridine-3-carboxylic acid.

Melting point: above 300° C.

$^1$H-NMR (DMSO-$d_6$) δ: 8.57 (1H, s, $C_2$—H), 8.01 (1H, d, $C_5$—H ), 6.95–7.35 (3H, m, ARM-H), 5.12 (4H, brs, 2 x—$\underline{CH_2}$N—), 3.84 (3H, s, $OCH_3$), 3.78 (1H. m,

1.10°–1.40 (4H, m,

)

Reference Example 1

4-aminoisoindoline (1) A mixture of 40 g of 2,3-dimethylnitrobenzene, 94 g of N-bromosuccinimide, and 500 mg of benzoyl peroxide was refluxed in 400 ml of carbontetrachloride for 20 hours. After cooling, the insoluble material was filtered off and washed with a small amount of carbontetrachloride. The filtrate and carbontetrachloride used for the washing were mixed and concentrated under reduced pressure to give an oily residue containing 2,3-bis(bromomethyl)-nitrobenzene as a major product.

(2) The above oily material was dissolved in 700 ml of acetone and 175 ml of water. 177 g of sodium carbonate was added to the solution. To the mixture thus obtained was added 28.4 g of benzylamine dissolved in 90 ml of acetone dropwise over 3 hours while stirring vigorously at room temperature. After the addition, the stirring was continued overnight at room temperature. Inorganic salts produced were removed by filtration and the filtrate was concentrated under reduced pressure. The residue was dissolved to ethyl acetate and extracted with 3 N hydrochloric acid three times. The hydrochloric acid layers were combined and basified with sodium carbonate and extracted two times with ethyl acetate. The organic layer was washed with brine and concentrated. The residue was purified by chromatography on silica gel (benzene/ethyl acetate=15/1) and recrystallized from isopropyl ether to afford 15 g of 2-benzyl-4-nitroisoindoline.

Melting Point: 77.5°–78° C.

$^1$H-NMR (CDCl$_3$) δ: 3.95 (2H, s), 4.02 (2H, s), 4.45 (2H, s), 7.20–7.60 (6H, m), 8.05 (2H, d, J=11H$_z$)

(3) 11.5 g of 2-benzyl-4-nitroisoindoline was dissolved in 150 ml of methanol and to the solution was added 1.5 g of 10% palladium on carbon. The mixture was stirred under a hydrogen gas stream under atmospheric pressure for one day at room temperature and for another 5 days at 40° C.. The catalyst was removed by filtration and the filtrate was concentrated. The residue was purified by a vacuum distillation (bath temperature: 150°–180° C., pressure: 0.1 mmHg) to obtain 3.74 g of 4-aminoisoindoline.

Melting Point: 81°–85° C.

$^1$H-NMR (CDCl$_3$) δ: 4.10 (2H, s), 4.25 (2H, s), 6.50–7.10 (3H, m)

Reference Example 2

5-aminoisoindoline

1) An oily material containing 3,4-bis(bromomethyl)-nitrobenzene as the major component was prepared in the same manner as in Reference Example 1 using 70 g of 3,4-dimethylnitrobenzene, 165 g of N-bromosuccinimide, 1.5 g of benzoyl peroxide, and 700 ml of carbontetrachloride.

(2) The above oily material and 184 g of sodium carbonate were added to a mixture of 900 ml of acetone and 225 ml water. To the mixture was added 50 g of benzylamine dissolved in 110 ml of acetone dropwise over 3 hours while stirring at room temperature. After the addition, the stirring was continued overnight at room temperature. The mixture was processed in a similar manner in Reference Example 1 to give 8.3 g of 2-benzyl-5-nitroisoindoline.

Melting Point: 80.5°–81° C.

(3) 7.23 g of 2-benzyl-5-nitroisoindoline was dissolved into 100 ml of methanol and to the solution was added 1.5 g of 10% palladium on carbon. The mixture was stirred under a hydrogen gas stream under atmospheric pressure for 2 days at room temperature and another 5 days at 40° C. The catalyst was removed by filtration and the filtrate was concentrated. The residue was purified by vacuum distillation (bath temperature: 150°–180° C., pressure: 0.1 mmHg) to obtain 2.94 g of 5-aminoisoindoline.

Melting Point: 113°–119° C.

$^1$H-NMR (CDCl$_3$-CD$_3$OD) δ: 4.10 (4H s), 6.50–6.70 (2H, m), 7.02 (1H, d, J=8H$_z$)

Reference Example 3

5-ethylaminoisoindoline (1) 4.0 g of 2-benzyl-5-nitroisoindoline prepared in Reference Example 2-(2) was dissolved in 40 ml of methanol and 800 mg of 10% palladium on carbon was added to the solution. The catalytic hydrogenation was performed for 32 hours at room temperature and under atmospheric pressure. After removing the catalyst by filtration, the filtrate was concentrated to obtain 2.88 g of 2-benzyl-5-aminoisoindoline.

(2) 2-benzyl-5-aminoisoindoline prepared above was dissolved in 50 ml of anhydrous benzene, and 1.77 g of acetic anhydride was added. After standing for 2 hours at room temperature, the mixture was washed with 5% sodium bicarbonate and brine. The organic layer was concentrated to afford 2-benzyl-5-acetamidoisoindoline.

(3) 2-benzyl-5-acetamidoisoindoline prepared above was dissolved in 30 ml of anhydrous tetrahydrofuran and to the solution was dropwise added 600 mg of lithium aluminum hydride dissolved in 10 ml of tetrahydrofuran over 10 minutes. After the mixture was refluxed for 2 hours, ether saturated with water was added to it. The resulting precipitatess were removed by filtration and the filtrate was concentrated. The residue was purified by column chromatography on silica gel (chloroform/methanol =25/1) to obtain 2.19 g of 2-benzyl-5-ethylaminoisoindoline as a dark brown oil.

(4) 400 mg of 10% palladium on carbon was added to 2.17 g of 2-benzyl-5-ethylaminoisoindoline prepared above in 30 ml of methanol and catalytic hydrogenation was carried out at 45° C. for 7 days. After removing the catalyst by filtration, the filtrate was concentrated and purified by vacuume distillation (bath temperature: 160°–200° C., pressure: 0.1 mmHg) to obtain 950 mg of 5-ethylaminoisoindoline.

Melting Point: 69°–71° C.

$^1$H-NMR (CDCl$_3$) δ: 1.25 (3H, t, J=7.5H$_z$), 3.15 (2H, q, J=7.5H$_z$), 4.05–4.20 (4H, m), 6.40–6.55 (2H, m), 7.02 (1H, d, J=9H$_z$)

Reference Example 4

4-methoxyisoindoline (1) 25 g of 2,3-dimethylanisole, 65 g of N-bromosuccinimide, 600 mg of benzoyl peroxide, and 500 ml of carbontetrachloride were processed in the same manner as in Reference Example 1, (1) to give a mixture containing 2,3-bis-(bromomethyl)anisole as a major component.

(2) The 2,3-bis-(bromomethyl)anisole prepared above and 1.5 g of benzyltriethylammonium chloride were dissolved in a mixture of 80 ml of aqueous 50% sodium hydroxide and 350 ml of toluene. To the solution was dropwise added 21.6 g of benzylamine over 15 minutes while stirring at room temperature. After stirring for one day for one day, the organic layer was separated and washed with brine. After concentration, the residue was purified by chromatography on silica gel (benzene/ethyl acetate=15/1) to give 15.2 g of 2-benzyl-4-methoxyisoindoline as an oily substance.

$^1$H-NMR (CDCl$_3$) δ: 3.78 (3H, s), 4.94 (2H, s), 6.65–7.50 (8H, m)

(3) 1.5 g of 10% palladium on carbon was added to a solution of 8.5 g of 2-benzyl-4-methoxyisoindoline in 100 ml of methanol and hydrogenation was performed at 45° C. for 7 days. After removing the catalyst by filtration, the filtrate was concentrated and purified by vacuum distillation (bath temperature: 160°–180 ° C., pressure: 0.1 mmHg) to obtain 3.44 g of 4-methoxyisoindoline.

Melting Point: 58.5°–60° C.

$^1$H-NMR (CDCl$_3$) δ: 3.83 (3H, s), 4.15–4.35 (4H, m), 6.65–7.30 (3H, m)

Reference Example 5

4-hydroxyisoindoline hydrobromide 1.1 g of 4-methoxyisoindoline was dissolved in a mixture of 10 ml of 48% bydrobromic acid and 10 ml of acetic acid, and the solution was refluxed for 18 hours. After concentration, the residue was recrystallized from methanol to obtain 790 mg of the target compound.

Melting Point: 221°–231° C. (decomposed)

$^1$H-NMR (CD$_3$OD) δ: 4.55 (2H, s), 4.60 (2H, s), 6.75–6.25 (3H, m)

Reference Example 6

5-chloroisoindoline (1) A mixture of 2.0 g of 3,4-dimethylchlorobenzene, 5.06 g of N-bromosuccinimide, and 30 mg of benzoyl peroxide was refluxed in 20 ml of carbontetrachloride for 18 hours. After cooling, the insoluble material was filtered off and washed with a small amount of carbontetrachloride. The filtrate and the washing were combined and concentrated under reduced pressure to obtain an oily product containing 3,4-bis(bromomethyl)-chlorobenzene as a major component.

(2) To a suspension of 1.30 g of 55% sodium hydride in mineral oil in 50 ml of anhydrous DMF was dropwise added a solution of 2.44 g of p-toluenesulfonamide in 10 ml of anhydrous DMF over 1 hour under vigorous stirring at room temperature. After the addition, the mixture was stirred for 1 hour at room temperature and another 1 hour under reflux. To this mixture was added dropwise a solution of the compound produced above [Reference Example 6-(1)]in 30 ml of anhydrous DMF at 58°–62° C.. After the addition, the mixture was stirred for 1 hour at 60° C. and overnight at room temperature. The resultant mixture was poured over ice and the resulting precipitates were collected by filtration. The precipitates were washed with water and dissolved in chloroform. This solution was washed with 1 N hydrochloric acid, 5% sodium carbonate, and then brine. Concentration and recrystallization from ethnol gave 1.13 g of 2-(p-toluenesulfonyl)-5-chloroisoindoline was obtained by recrystallization in ethanol.

$^1$H-NMR (CDCl$_3$) δ: 7.35 and 7.76 (each 2H, ABq, J=10H$_z$, tosyl group ARM-H), 7.05–7.30 (3H, m, isoindoline ARM-H), 4.60 (4H, s, 2 x —CH$_2$N—), 2.24 (3H, s, CH$_3$)

(3) 1.0 g of 2-(p-toluenesulfonyl)-5-chloroisoindoline and 1.0 g of phenol were added to a mixture of 8 ml of 48% hydrobromic acid and 1.4 ml of propionic acid, and the mixture was refluxed for 6 hours. The resultant reaction mixture was diluted with 10 ml of water and extracted 2 times with 50 ml of ether. The water layer was basified with aqueous sodium hydroxide solution and extracted with 50 ml of ether 4 times. The extract was concentrated and the residue was purified by vacuum distillation (bath temperature: 130°–140 ° C., pressure: 7 mmHg) to obtain 256 mg of 5-chloroisoindoline.

Melting Point: 49°–50° C.

$^1$H-NMR (CDCl$_3$) δ: 7.10–7.30 (3H, m, ARM-H), 4.21 (4H, brs, 2 x —CH$_2$N—)

Reference Example 7

4-fluoroisoindoline (1) 3.0 g of 2,3-dimethylfluorobenzene, 8.6 g of N-bromosuccinimide, 50 mg of benzoyl peroxide, and 30 ml of carbontetrachloride were processed in the same manner as in Reference Example 6-(1) to prepare an oily product containing 2,3-bis-(bromomethyl)-fluorobenzene as a major component.

(2) The whole product prepared above, 2.21 g of 55% sodium hydride, and 4.14 g of p-toluenesulfonamide were processed in a similar manner as in Reference Example 6-(2) to give 2.60 g of 2-(p-toluenesulfonyl)-4-fluoroisoindoline.

$^1$H-NMR (CDCl$_3$) δ: 7.35 and 7.80 (each 2H, ABq, J=10H$_z$, tosyl group ARM-H), 6.85-7.30 (3H, m, isoindoline ARM-H), 4.66 (4H, s, 2 x —CH$_2$N—), 2.43 (3H, s, CH$_3$)

(3) The procedure described in Reference Example 6-(3) was followed using 2.30 g of 2-(p-toluenesulfonyl)-4-fluoroisoindoline, 2.30 g of phenol, 20 ml of 48% hydrobromic acid, and 3.5 ml of propionic acid. Purification of the crude product by vacuum distillation (bath temperature: 110°-150° C., pressure: 7 mmHg) gave 604 mg of 4-fluoroisoindoline.

Melting Point: 46.5°-48.5° C.

$^1$H-NMR (CDCl$_3$) δ: 6.82-7.30 (3H, m, ARM-H), 4.25 and 4.30 (each 2H, s, 2x —CH$_2$N—)

Reference Example 8

4-chloroisoindoline (1) 28.1 g of 2,3-dimethylchlorobenzene, 71.2 g of N-bromosuccinimide, 300 mg of benzoyl peroxide, and 300 ml of carbontetrachloride were processed in a similar manner as in Reference Example 6-(1) to prepare an oily product containing 2,3-bis-(bromomethyl)-chlorobenzene as a major component.

(2) The whole product prepared above, 18.33 g of 5% sodium hydride, and 34.24 g of p-toluenesulfonamide were processed in a similar manner as in Reference Example 6-(2) to give 24.1 g of 2-(p-toluenesulfonyl)-4-chloroisoindoline.

$^1$H-NMR (CDCl$_3$) δ: 7.33 and 7.76 (each 2H, ABq, J=10H$_z$, tosyl group ARM-H), 7.08-7.25 (3H, m, isoindoline ARM-H), 4.58 (4H, s, 2 x —CH$_2$N—), 2.40 (3H, s, CH$_3$) (3) The procedure of Reference Example 6-(3) was followed using 12.32 g of 2-(p-toluenesulfonyl)-4-chloroisoindoline, 10 g of phenol, 150 ml of 48% hydrobromic acid, and 20 ml of propionic acid. Through purification of the crude product by vacuum distillation 3.1 g of 4-chloroisoindoline was produced.

Boiling Point: 140°-145° C./2 mmHg $^1$H-NMR (CDCl$_3$) δ: 7.05-7.20 (3H, m, ARM-H), 4.28 and 4 30 (each 2H, s, 2 x —CH$_2$N—)

Reference Example 9

5-fluoroisoindoline (1) 24.82 g of 3,4-dimethylfluorobenzene, 71.2 g of N-bromosuccinimide, 400 mg of benzoyl peroxide, and 300 ml of carbontetrachloride were processed in a similar manner as in Reference Example 6-(1) to give an oily product containing 3,4-bis-(bromomethyl)-fluorobenzene as a major component.

(2) The whole product prepared above, 18.33 mg of 55% sodium hydride, and 32.2 g of p-toluenesulfonamide were processed in a similar manner as in Reference Example 6-(2) to give 7.3 g of 2-(p-toluenesulfonyl)-5-fluoroisoindoline.

$^1$H-NMR (CDCl$_3$) δ: 7.33 and 7.78 (each 2H, ABq, J=10H$_z$, tosyl group ARM-H), 6.82-7.15 (3H, m, isoindoline ARM-H), 7.60 (4H, brs, 2 x —CH$_2$N—), 2.41 (3H, s, CH$_3$)

(3) The procedure of Reference Example 6-(3) was followed using 10.2 g of 2-(p-toluenesulfonyl)-5-fluoroisoindoline, 10 g of phenol, 150 ml of 48% hydrobromic acid, and 25 ml of propionic acid. Purification of the crude product by vacuum distillation gave 5.0 mg of 5-fluoroisoindoline.

Boiling Point: 140°-145° C./16 mmHg $^1$H-NMR (CDCl$_3$) δ: 6.85-7.20 (3H, m, ARM-H) 4.15-4.25 (4H, m, 2 x —CH$_2$N—)

Reference Example 10

4-bromoisoindoline (1) 1.85 g of 2,3-dimethylbromobenzene, 3.56 g of N-bromosuccinimide, 20 mg of benzoyl peroxide, and 20 ml of carbontetrachloride were processed in a similar manner as in Reference Example 6-(1) to give an oily product containing 2,3-bis-(bromomethyl)-bromobenzene as a major component.

(2) The whole product prepared above, 840 g of 55% sodium hydride, and 1.71 g of p-toluenesulfonamide were processed in a similar manner as in Reference Example 6-(2) to give 1.37 g of 2-(p-toluenesulfonyl)-4-bromoisoindoline.

$^1$H-NMR (CDCl$_3$) δ: 7.35 and 7.78 (each 2H, ABq, J=10H$_z$, tosyl group ARM-H), 7.10-7.50 (3H, m, isoindoline ARM-H), 4.59 and 4.70 (each 2H, s, 2 x —CH$_2$N—), 2.43 (3H, s, CH$_3$)

(3) The procedure of Reference Example 6-(3) was followed using 9.61 g of 2-(p-toluenesulfonyl)-4-bromoisoindoline, 10 g of phenol, 120 ml of 48% hydrobromic acid, and 20 ml of propionic acid. Purification of the crude product by vacuum distillation gave 5.0 g of 4-bromoisoindoline.

Boiling Point: 130° C./0.2 mmHg $^1$H-NMR (CDCl$_3$) δ: 7.05-7.35 (3H, m, ARM-H), 4.25 and 4.30 (each 2H, s, 2 x —CH$_2$N—)

Reference Example 11

5-bromoisoindoline (1) 37 g of 3,4-dimethylbromobenzene, 71.2 g of N-bromosuccinimide, 400 mg of benzoyl peroxide, and 400 ml of carbontetrachloride were processed in a similar manner as in Reference Example 6-(1) to give an oily product containing 3,4-bis-(bromomethyl)-bromobenzene as a major component.

(2) The whole product prepared above, 18.3 g of 55% sodium hydride, and 32.2 g of p-toluenesulfonamide were processed in a similar manner as in Reference Example 6-(2) to give 25.2 g of 2-(p-toluenesulfonyl)-5-bromoisoindoline.

$^1$H-NMR (CDCl$_3$) δ: 7.32 and 7.76 (each 2H, ABq, J=10H$_z$, tosyl group ARM-H), 6.98-7.40 (3H, m, isoindoline ARM-H), 4.56 (4H, m, 2 x —CH$_2$N—), 2.42 (3H, s, CH$_3$)

(3) The procedure of Reference Example 6-(3) was followed using 12.8 g of 2-(p-toluenesulfonyl)-5-bromoisoindoline, 12 g of phenol, 160 ml of 48% hydrobromic acid, and 30 ml of propionic acid. Purification of the crude product by vacuum distillation gave 2.5 g of 5-bromoisoindoline.

Boiling Point: 135° C./0.2 mmHg $^1$H-NMR (CDCl$_3$) δ: 7.05-7.38 (3H ARM-H) 4.18 and 4.23 (each 2H, s, 2 x —CH$_2$N—)

Reference Example 12

4-nitroisoindoline (1) 2.54 g of 2-benzyl-4-nitroisoindoline was dissolved in 10 ml of chloroform, and 1.27 g of sodium carbonate was added to the solution. To the mixture was added dropwise 1.30 g of ethyl chloroformate under ice-cooling while stirring. After the addition, the stirring was continued for 20 hours at room temperature. The insoluble materials were removed by filtration and the filtrate was washed with water, 5% hydrochloric acid, and then with water. The mixture was concentrated and recrystallized from a chloroform-ether mixed solvent to obtain 1.73 g of 2-ethoxycarbonyl-4-nitroisoindoline.

$^1$H-NMR (CDCl$_3$) δ: 7.46–8.23 (3H m, ARM-H), 4.75–5.25 (4H, m, 2 x —CH$_2$N—), 4.26 (2H, q, J=7H$_z$, —OCH$_2$CH$_3$), 1.35 (3H, t, J=7H$_z$, —OCH$_2$CH$_3$)

(2) 2.36 g of 2-ethoxycarbonyl-4-nitroisoindoline was added to 70 ml of 25% hydrobromic acid in acetic acid. The mixture was stirred for 20 hours at 100° C., concentrated under reduced pressure, and recrystallized from ethanol to give 2.11 g of 4-nitroisoindoline hydrobromide.

$^1$H-NMR (D$_2$O) δ: 7.63–8.30 (3H. ARM-H). 4.80 and 5.16 (each 2H, s, 2 x —CH$_2$N—)

Reference Example 13

5-methoxyisoindoline (1) 27.2 g of 3,4-dimethylanisole, 71.2 g of N-bromosuccinimide, 400 mg of benzoyl peroxide, and 400 ml of carbontetrachloride were processed in a similar manner as in Reference Example 6-(1) to give an oily residue containing 3,4-bis-(bromomethyl)anisole as a major component.

(2) The whole product prepared above and 2 g of benzyltriethylammonium chloride were dissolved in a mixture of 90 ml of 50% aqueous sodium hydroxide and 380 ml of toluene. To the solution was dropwise added 23.6 g of benzylamine while vigorously stirring. After stirring at room temperature for 2 days, the mixture was diluted with benzene. The organic layer was separated and washed twice with brine. After concentration, the residue obtained was purified by chromatography on silica gel (benzene/ethyl acetate=15/1) to give 12.5 g of 2-benzyl-5-methoxyisoindoline as an oily substance.

$^1$H-NMR (CDCl$_3$) δ: 6.50–7.50 (8H, m, ARM-H), 3.89 (4H, brs, 2 x —CH$_2$N—), 3.84 (2H, s, —CH$_2$Ph), 3.77 (3H, s, CH$_3$)

(3) 1.5 g of 10% palladium on carbon was added to a solution of 12.5 g of 2-benzyl-5-methoxyisoindoline prepared above in 150 ml of methanol and the mixture was stirred under hydrogen gas stream at 40° C. under atmospheric pressure for 7 days. After removing the catalyst by filtration, the filtrate was concentrated and purified by vacuum distillation to give 4.7 g of 5-methoxyisoindoline.

Boiling Point: 105°–109° C./1 mmHg $^1$H-NMR (CDCl$_3$) δ: 6.70–7.17 (3H, m, ARM-H), 4.17 and 4.20 (each 2H, s, 2 x —CH$_2$N—), 3.80 (3H, s, CH$_3$)

Reference Example 14

4-methoxycarbonylisoindoline hydrochloride (1) To 160 ml of methanol cooled to −10° C. was dropwise added 46.4 ml of thionyl chloride while stirring. To the solution was added a mixture of 24 g of 2,3-dimethyl benzoic acid and 1 ml of DMF, and the mixture was stirred at room temperature for 4 days. After concentration, the residue was dissolved in ether. The solution was washed with water, 5% sodium carbonate, and water in this order. The solvent was evaporated and the residue was purified by vacuum distillation to obtain 25.1 g of methyl 2,3-dimethylbenzoate.

(2) 24.6 g of methyl 2,3-dimethylbenzoate, 53.4 g of N-bromosuccinimide, 300 mg of benzoyl peroxide, and 300 ml of carbontetrachloride were processed in a similar manner as in Reference Example 6-(1) to give a mixture containing methyl 2,3-bis-(bromomethyl)benzoate as a major component.

(3) The whole product prepared was dissolved into 300 ml of benzene. To the mixture were dropwise added a solution of 16.1 g of benzylamine and 30.4 g of triethylamine in 150 ml of benzene over 30 minutes while stirring at room temperature, followed by reflux for 20 hours. Insoluble components were removed by filtration and the filtrate was washed with 5% sodium carbonate and then with water. After concentration, the residue obtained was purified by chromatography on silica gel (benzene/ethyl acetate=10/1) to give 16.4 g of 2-benzyl-4-methoxycarbonylisoindoline.

$^1$H-NMR (CDCl$_3$) δ: 7.20–7.90 (8H, m, ARM-H), 4.30 (2H, s, —CH$_2$Ph), 3.94 (4H, s, 2 x —CH$_2$N—), 3.85 (3H, s, CH$_3$)

(4) 1.5 g of 10% palladium on carbon was added to a solution of 13.4 g of 2-benzyl-4-methoxycarbonylisoindoline in 200 ml of methanol and the mixture was stirred under hydrogen gas stream at 50° C. under atmospheric pressure for 4 days. After removing the catalyst by filtration and after concentration of the filtrate, 15 ml of dioxane solution of 4 N hydrochloric acid was added to the residue. The mixture was concentrated under reduced pressure and recrystallized from chloroform to give 8.2 g of 4-methoxycarbonylisoindoline hydrochloride.

$^1$H-NMR (D$_2$O) δ: 7.50–8.10 (3H, m, ARM-H), 4.74 and 4.98 (each 2H, s, 2 x —CH$_2$N—), 3.97 (3H, s, CH$_3$)

Reference Example 15

5-methoxycarbonylisoindoline hydrochloride (1) 15.0 g of 3,4-dimethyl benzoic acid, 29.0 ml of thionyl chloride, 100 ml of methanol, and 1 ml of DMF were processed in a similar manner as in Reference Example 14-(1) to give 15.7 g of methyl 3,4-dimethylbenzoate.

(2) 18.1 g of methyl 3,4-dimethylbenzoate, 39.2 g of N-bromosuccinimide, 200 mg of benzoyl peroxide, and 200 ml of carbontetrachloride were processed in a similar manner as in Reference Example 6-(1) to give a mixture containing methyl 3,4-bis-(bromomethyl)benzoate as a major component. (3) The procedure of Reference Example 14-(3) was followed using the whole mixture prepared above, 11.8 g of benzylamine, and 22.9 g of triethylamine to give 16.0 g of 2-benzyl-5-methoxycarbonylisoindoline.

(4) The procedure of Reference Example 14-(4) was followed using 13.4 g of 2-benzyl-5-methoxycarbonylisoindoline, 1.5 g of 10% palladium on carbon, and 150 ml of methanol to give 8.1 g of 5-methoxycarbonylisoindoline hydrochloride.

$^1$H-NMR (D$_2$O) δ: 7.50–8.05 (3H, m, ARM-H), 4.75 (4H, m, 2 x —CH$_2$N—), 3.95 (3H, s, CH$_3$)

Reference Example 16

4-hydroxymethylisoindoline (1) 8.02 g of 2-benzyl-4-methoxycarbonylisoindoline was dissolved in 20 ml of anhydrous tetrahydrofuran and to the solution was added 1.9 g of lithium aluminum hydride. After stirring for 20 hours at room temperature, an aqueous solution of sodium sulfate was added. Insoluble materials were removed by filtration, the filtrate was concentrated, and the residue was recrystallized from ether to give 5.27 g of 2-benzyl-4-hydroxymethylisoindoline.

$^1$H-NMR (CDCl$_3$) δ: 7.03–7.50 (8H, m, ARM-H), 4.18 (2H, s, —CH$_2$OH), 3.92 and 3.89 (each 2H, s, 2 x —CH$_2$N—), 3.62 (3H, s, CH$_2$Ph)

(2) To a mixture of 5.27 g of 2-benzyl-4-hydroxymethylisoindoline and 2.43 g of sodium carbonate in 25 ml of chloroform was added dropwise 2.49 g of ethyl chloroformate under ice-cooling while stirring. After stirring for 2 days at room temperature, the mixture was washed with water and concentrated. The residue was purified by chromatography on silica gel (chloroform/methanol =10/1) to obtain 3.25 g of 2-ethoxycarbonyl-4-hydroxymethylisoindoline.

(3) 3.03 g of 2-ethoxycarbonyl-4-hydroxymethylisoindoline and 2.91 g of potassium hydroxide were dissolved in a mixture of 25 ml isopropyl alcohol and 2.5 ml of water. The mixture was heated under refluxing for 3 days. After the addition of water, the resulting reaction mixture was extracted with chloroform. The extract was washed with brine, concentrated, and recrystallized from carbontetrachloride to give 1.48 g of 4-hydroxymethylisoindoline.

$^1$H-NMR (CDCl$_3$) δ: 7.10–7.29 (3H, m, ARM-H), 4.58 (2H, s, —CH$_2$OH), 4.10–4.25 (4H, m, 2 x —CH$_2$N—)

Reference Example 17

5-hydroxymethylisoindoline (1) 5.94 g of 2-benzyl-5-hydroxymethylisoindoline was produced in the similar manner as Reference Example 16-(1) using 8.02 g of 2-benzyl-5-methoxycarbonylisoindoline and 1.9 g of lithium aluminum hydride.

(2) 1.64 g of 2-ethoxycarbonyl-4-hydroxymethylisoindoline was produced in a similar manner as in Reference Example 16-(2) using 2.87 g of 2-benzyl-5-hydroxymethylisoindoline, 1.30 g of ethyl chloroformate, 1.27 g of sodium carbonate, and 12 ml of chloroform.

$^1$H-NMR (CDCl$_3$) δ: 7.28 (3H, m, ARM-H), 4.66 (4H m, 2 x —CH$_2$N—), 4.21 (2H, q, J=7H$_z$, -OCH$_2$CH$_3$), 1.32 (3H, t, J=7H$_z$, —OCH$_2$CH$_3$)

(3) 810 mg of 5-hydroxymethylisoindoline was produced in a similar manner as Reference Example 16-(3) using 1.63 g of 2-ethoxycarbonyl-5-hydroxymethylisoindoline, 1.12 g of potassium hydroxide, 14 ml isopropyl alcohol, and 1.4 ml of water.

$^1$H-NMR (CDCl$_3$) δ: 7.15 (3H, brs, ARM-H , 4.65 (2H, s, —CH$_2$OH), 4.17 and 4.09 (each 2H, s, 2 x —CH$_2$N—)

Reference Example 18

4-(tert-butyloxycarbonylaminomethyl)isoindoline 48 1 g of 2-benzyl-4-methoxycarbonylisoindoline prepared in Reference Example 14-(3) was added to a solution of 16 g of sodium hydroxide in 160 ml of water and the mixture was heated under reflux for 3 hours. After removing insoluble materials by filtration, the filtrate was adjusted to pH 5 with 6 N hydrochloric acid. The resulting crystals were collected by filtration, and was washed with water, cold ethanol, ether, and then chloroform to give 35.0 g of 2-benzylisoindoline-4-carboxylic acid.

(2) A mixture of 35.0 g of 2-benzylisoindoline-4-carboxylic acid, 150 ml of thionyl chloride, and 1 ml of DMF was heated under reflux for 10 hours. After cooling, the reaction mixture was concentrated to the extent that the acid chloride crystals does not deposit. To the concentrate was added dropwise 28% aqueous ammonia under ice cooling and stirring After stirring for 3 hours crystals produced was collected by filtration and washed with water. The crystals were dissolved in chloroform, washed with 5% sodium hydroxide and water, and concentrated. The residue was recrystallized from ether to obtain 24.1 g of 2-benzylisoindoline-4-carboxamide.

$^1$H-NMR (CDCl$_3$) δ: 7.20–7.45 (8H ARM-H) 5.92 (2H brs, —CONH$_2$), 4.25 (2H, s, —CHHD 2Ph), 3.87 (4H, brs, 2 x —CH$_2$N—)

(3) 4.16 g of 2-benzylisoindoline-4-carboxamide was dissolved in 16 ml of anhydrous tetrahydrofuran. 1.25 g of lithium aluminum hydride was added to the solution while stirring under ice cooling and the mixture was heated under reflux for 20 hours. After cooling, a excess lithium aluminum hydride was decomposed by an aqueous solution of sodium sulfate. Insoluble materials were removed by filtration, the filtrate was dried over sodium sulfate, and solvent was evaporated to give a product containing 2-benzyl-4-aminomethylisoindoline as a major component.

(4) The whole product prepared in Reference Example 18-(3) above was dissolved in 50 ml of anhydrous tetrahydrofuran. After the addition of 3.60 g of di-t-butyl-dicarbonate, the mixture was stirred for 20 hours at room temperature. The reaction mixture was concentrated and purified by silica gel chromatography (benzene/ethyl acetate =10/1). Recrystallization in ether gave 1.64 g of 2-benzyl-4-(tert-butyloxycarbonylaminomethyl)isoindoline was obtained.

$^1$H-NMR (CDCl$_3$) δ: 7.00–7.40 (8H, m, ARM-H), 4.18 (2H, d, J=6H$_z$, benzyl-H), 3.90 (6H, s, 2 x —CH$_2$N—and benzyl-H), 1.43 (9H, s, C(CH$_3$)$_3$)

(5) 3.38 g of 2-benzyl-4-(tertbutyloxycarbonylaminomethyl)isoindoline was dissolved in 10 ml of chloroform and 1.27 g of sodium carbonate was added to it. To this solution was added dropwise 2.04 g of benzyl chloroformate under ice-cooling and stirring, and the mixture was stirred for 2 hours at room temperature. Insoluble materials were removed by filtration and the filtrate was concentrated. Recrystallization from ether gave 3.48 g of 2-benzyloxycarbonyl-4-(tert-butyloxycarbonylaminomethyl)isoindoline.

$^1$H-NMR (CDCl$_3$) δ: 7.10–7.45 (8H, m, ARM-H), 5.20 (2H, brs, —OCH$_2$Ph), 4.74 (4H, brs, 2 x —CH$_2$N—), 4.25 (2H, brs, —CH$_2$NHCOO$^t$BU), 1.45 (9H, d, C(CH$_3$)$_3$)

(6) 3.44 g of 2-benzyloxycarbonyl-4-(tertbutyloxycarbonylaminomethyl)isoindoline was dissolved in 50 ml of methanol. 200 mg of 10% palladium on carbon was added to it and the mixture was stirred under hydrogen gas stream for 3 days. After removing the catalyst by filtration, the filtrate was concentrated and the residue was recrystallized from ether to give 1.75 g of 4-(tert-butyloxycarbonylaminomethyl)isoindoline.

$^1$H-NMR (CDCl$_3$) δ: 7.10–7.35 (3H, m, ARM-H), 4.62 and 4.68 (each 2H, brs, 2 x —CH$_2$N—), 4.22 (2H, brs, —CH$_2$NHCOO$^t$Bu), 1.42 (9H, brs, C(CH$_3$)$_3$)

Reference Example 19

5-acetamidomethylisoindoline hydrobromide 92.8 g of 3,4-dimethylbenzyl chloride and 116.7 g of potassium salt of phthalimide were dissolved in 600 ml of DMF and the solution was heated under reflux for 20 hours. After cooling, insoluble materials were removed by filtration and the filtrate was concentrated. The residue was dissolved in chloroform, washed with 0.1 N aqueous sodium hydroxide and then with water, and concentrated. 140 g of 4-phthalimidomethyl-o-xylene was obtained by recrystallization from a chloroform-ether mixed solvent.

(2) 80.8 g of 4-phthalimidomethyl-o-xylene was dissolved into 800 ml of carbontetrachloride. To the stirred solution was added dropwise 97.5 g of bromine at 50° C. under irradiation with a tungsten lamp. The stirring was further continued under the light irradiation for 20 hours. Crystals deposited were collected by filtration and washed with carbontetrachloride to give 63.9 g of 4-phthalimidomethyl-α,α'-dibromo-orthoxylene.

(3) 16.0 g of 60% sodium hydride was added to 200 ml of anhydrous DMF. To the mixture was added dropwise a solution of 34.2 g of p-toluenesulfonamide in 200 ml of anhydrous DMF while stirring at room temperature over 30 minutes. After stirring for 1 hour at 60° C. a solution of 84.6 g of 4-phthalimidemethyl-α,α'-dibromo-o-xylene in 800 ml of DMF was added dropwise at 60 ° C. under stirring. The resultant reaction mixture was concentrated under reduced pressure and the residue was dissolved in chloroform, and washed with 5% hydrochloric acid and then with water. After removing the solvent by evaporation, 20.8 g of 2-(p-toluenesulfonyl)-5-phthalimidomethylisoindoline was produced by recrystallization from ethanol.

$^1$H-NMR (CDCl$_3$) δ: 7.05–7.92 (11H, m, tosyl group, isoindoline ring and ARM-H of phthalimide group), 4.80 (2H, s, Pht-NCH$_2$—), 4.59 (4H, s, 2 x —CH$_2$N—), 2.38 (3H, s, CH$_3$)

(4) 21.6 g of 2-(p-toluenesulfonyl)-5-phthalimidomethylisoindoline and 5 ml of hydrazine hydrate was dissolved in 300 ml of methanol and the solution was heated under reflux for 2 hours. After reaction mixture was allowed to cool, 50 ml of water was added to it. The mixture was concentrated to a half volume under reduced pressure. To the residue 500 ml of 10% aqueous sodium hydroxide and 1 liter of chloroform were added and the whole mixture was thoroughly shaken. The chloroform layer was separated and washed with 5% aqueous sodium hydroxide and then with water. After removing the solvent by evaporation, the residue was recrystallized from ether to give 15.0 g of 2-(p-toluenesulfonyl)-5-aminomethylisoindoline.

$^1$H-NMR (CDCl$_3$) δ: 7.30 and 7.79 (each 2H, ABq, tosyl group ARM-H), 7.05–7.27 (3H, m, isoindoline ARM-H), 4.60 (4H, s, 2 x —CH$_2$N—), 7.83 (2H, s, —CH$_2$NH$_2$), 2.40 (3H, s, CH$_3$)

(5) 14.5 g of g of 2-(p-toluenesulfonyl)-5-aminomethylisoindoline was dissolved in 200 ml of chloroform. 6.13 g of acetic anhydride was added dropwise to the solution under ice cooling while stirring. The mixture was stirred at room temperature for 1 hour and concentrated. The residue was recrystallized from n-hexane to give 16.3 g of 2-(p-toluenesulfonyl)-5-acetamidomethylisoindoline.

(6) 15.5 g of 2-(p-toluenesulfonyl)-5-acetamidomethylisoindoline and 7.5 g of phenol was added to 200 ml of 25% hydrobromic acid in acetic acid. The mixture was stirred for 6 hours at 60° C. and then for 20 hours at room temperature. The resulting reaction mixture was dried under reduced pressure and the residue was recrystallized from an ethanol-ether mixed solvent to give 11.3 g of 5-acetamidemethylisoindoline hydrobromide.

$^1$H-NMR (D$_2$O) δ: 7.28–7.47 (3H, m, ARM-H), 4.68 (4H, s, 2 x —CH$_2$N—), 4.40 (2H, s, —CH$_2$NHAc), 2.05 (3H, s, —NHCOCH$_3$)

Antibacterial Activity

The minimum growth inhibitory concentration (MIC: μg/ml) of the compounds of the present invention were measured according to the standard method of Japan Society of Chemotherapy [Chemotherapy, vol. 29, No.1, 76–79 (1981)]. The results are shown in Table 3.

TABLE 3

| Compound | Minimum Growth Inhibitory Concentration (μg/ml) | | |
|---|---|---|---|
| | S. aureus 209P (IFO 12732) | E. coli NIH JC-2 (IFO 12734) | P. aeruginosa (IFO 3445) * |
| Example 1 | <0.025 | 0.2 | 0.39 |
| Example 2 | <0.025 | 0.1 | 0.39 |
| Example 3 | <0.025 | 0.2 | 1.56 |
| Example 5 | 0.05 | 0.39 | 3.13 |
| Example 6 | <0.025 | 0.39 | 0.39 |
| Example 7 | <0.025 | 0.1 | 1.56 |
| Example 8 | <0.025 | 0.2 | 3.13 |
| Example 9 | 0.05 | 0.2 | 3.13 |
| Example 10 | <0.025 | 0.39 | 1.56 |
| Example 17 | 0.1 | 0.39 | 6.25 |
| Example 19 | <0.025 | 0.39 | 1.56 |
| Example 22 | <0.025 | 0.78 | 0.78 |
| Example 23 | <0.025 | 0.39 | 3.13 |
| Example 26 | <0.025 | 1.56 | 0.39 |
| Example 27 | <0.025 | 0.78 | 0.78 |
| Example 28 | <0.025 | 0.78 | 0.78 |
| Example 33 | <0.025 | 0.78 | 3.13 |
| Example 34 | <0.025 | 1.56 | 1.56 |
| Example 35 | <0.025 | 0.78 | 1.56 |
| Example 36 | <0.025 | 0.78 | 0.78 |
| Example 37 | <0.025 | 0.39 | 3.13 |
| Example 39 | <0.025 | 0.39 | >25 |
| Example 40 | <0.025 | 0.10 | 0.78 |
| Example 41 | <0.025 | 0.20 | 0.78 |
| Example 44 | <0.025 | 1.56 | 1.56 |
| Example 77 | <0.025 | 0.78 | 3.13 |
| Example 79 | <0.025 | 1.56 | 3.13 |
| Example 96 | <0.025 | 0.05 | 0.78 |
| Example 97 | <0.025 | 0.10 | 0.78 |
| Example 98 | <0.025 | 0.10 | 0.78 |
| Example 99 | <0.025 | 0.05 | 1.56 |
| Example 100 | <0.025 | 0.10 | 3.13 |
| Example 102 | 0.01 | <0.025 | 0.78 |
| Example 107 | 0.39 | 0.10 | 3.13 |
| Example 108 | 1.56 | 0.39 | 6.25 |
| Example 110 | 0.20 | 0.39 | 6.25 |
| Example 112 | 0.78 | 0.20 | 6.25 |
| Example 113 | 0.78 | 0.10 | 12.5 |
| Example 114 | 0.39 | 0.05 | 12.5 |
| Norfloxacine | 0.39 | 0.1 | 0.78 |

* IFO: Institute for Fermantation, Osaka

Obviously, numerous modifications and variations of the present invention are possible in light of the above teachings. It is therefore to be understood that the scope of the appended claims, the invention may be practiced otherwise than as specifically described herein.

What is claimed is:

1. An isoindoline derivative of formula (I),

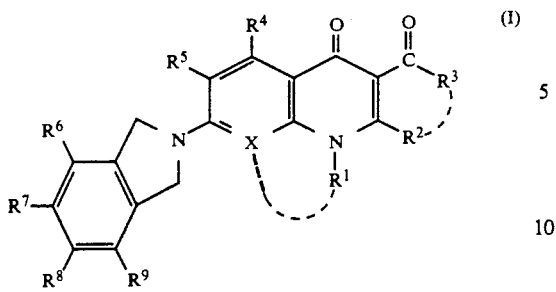

wherein:

R[1] is a lower alkyl group; an alkyl group substituted by an amino group, a mono-, di-, or tri-alkylamino group, a cyano group, a hydroxyl group, a lower alkoxy group, a carboxyl group, a lower alkoxycarbonyl group, a halogen atom, or a lower alkylthio group; a cyclo-lower alkyl group; a lower alkenyl group; a mono- or di-lower alkylamino group; a lower alkoxy group; a $C_{7-8}$ aralkyl group; a $C_{7-8}$ aralkyl group which is substituted by at least one member selected from the group consisting of halogen atoms, lower alkoxy groups, a hydroxy group, an amino group, and amino-lower alkyl groups; or a phenyl group; a phenyl group substituted by at least one member selected from the group consisting of halogen atoms, lower alkyl groups, lower alkoxy groups, a hydroxy group, an amino group, and amino-lower alkyl groups;

R[2] is a hydrogen atom; a group; or a lower alkylthio group;

R[3] is a hydroxy group; an amino group; a mono- or di-lower alkylamino group; or a group —OR[10] wherein R[10] is a carboxyl ester protective group selected from the group consisting of methyl, ethyl, benzyl, trialkyl silyl, acetoxymetyl, pivaloyloxymethyl, ethoxycarbonyloxyethyl, dimethylaminoethyl, 1-piperidinylethyl, trimethylaminoethyl and phthalidyl;

R[4] is a hydrogen atom; a halogen atom; a hydroxy group; a lower alkoxy group; a lower alkyl group; an amino group; or a mono-, di- or tri-lower alkylamino group;

R[5] is a halogen atom; a hydroxy group; or a lower alkoxy group;

R[6], R[7], R[8] and R[9], which each are the same or different, individually are a hydrogen atom; a halogen atom; a lower alkyl group; a lower alkyl group substituted by at least one member selected from the group consisting of an amino group, mono-, di-, and tri-alkylamino groups, a cyano group, a hydroxyl group, lower alkoxy groups, a carboxyl group, lower alkoxycarbonyl groups, halogen atoms, and lower alkylthio groups; a cyclo-lower alkyl group; a $C_{6-10}$ aryl group; a $C_{6-10}$ aryl group which is substituted by at least one member selected from the group consisting of halogen atoms, lower alkoxy groups, a hydroxy group, an amino group, and amino-lower alkyl groups; a $C_{7-8}$ aralkyl group; a $C_{7-8}$ aralkyl group which is substituted by at least one member selected from the group consisting of halogen atoms, lower alkoxy groups, a hydroxy group, an amino group, and amino-lower alkyl groups; a carboxyl groups; a lower alkoxycarbonyl group; a mono- or di-lower alkylcarbamoyl group; an $C_6$-$C_{10}$ arylcarbamoyl group; a CONH—Ar group, wherein Ar is an $C_{6-10}$ aryl group which is substituted by at least one member selected from the group consisting of halogen atoms, lower alkoxy groups, a hydroxy group, an amino group, and amino-lower alkyl groups; a formyl group; a nitrile group; a lower alkanoyl group; a —CO—Alk group, wherein Alk is a lower alkyl group substituted by at least one member selected from the group consisting of halogen atoms, lower alkoxy groups, and a phenyl group; an $C_6$-$C_{10}$ aroyl group; a —CO—Ar group, wherein Ar is an $C_6$-$C_{10}$ aryl group which is substituted by at least one member selected from the group consisting of halogen atoms, lower alkoxy groups, a hydroxy group, an amino group, and amino-lower alkyl groups; a hydroxy group; a lower alkoxy group; an $C_6$-$C_{10}$ aryloxy group; an O-Ar group, wherein Ar is an $C_6$-$C_{10}$ aryl group which is substituted by at least one member selected from the group consisting of halogen atoms, lower alkoxy groups, a hydroxy group, an amino group, and amino-lower alkyl groups; a lower alkanoyloxy group; an $C_5$-$C_{10}$ aroyloxy group; a —OCO—Ar group, wherein Ar is an $C_6$-$C_{10}$ aryl group which is substituted by at least one member selected from the group consisting of halogen atoms, lower alkoxy groups, a hydroxy group, an amino group, and amino-lower alkyl groups; an amino group; a mono-, di- or tri-lower alkylamino group; a lower $C_6$-$C_{10}$ alkanoylamino group; a lower aroylamino group; an —NH—Aro group, wherein Aro is an $C_6$-$C_{10}$ aroyl group which is substituted by at least one member selected from the group consisting of halogen atoms, lower alkoxy groups, a hydroxy group, an amino group, and amino-lower alkyl groups; a nitro group; a lower $C_6$-$C_{10}$ alkylsulfonyl group; an arylsulfonyl group; a —SO$_2$—Ar group, wherein Ar is an $C_6$-$C_{10}$ aryl group which is substituted by at least one member selected from the group consisting of halogen atoms, lower alkoxy groups, a hydroxy group, an amino group, and amino-lower alkyl groups; a group; a lower alkylthio group; a sulfonamide group; a lower $C_6$-$C_{10}$ alkylsulfonamide group; a lower arylsulfonamide group; a —SO$_2$NH—Ar group, wherein Ar is an $C_6$-$C_{10}$ aryl group which is substituted by at least one member selected from the group consisting of halogen atoms, lower alkoxy groups, a hydroxy group, an amino group, and amino-lower alkyl groups;

X represents a =CY— group, wherein Y represents a hydrogen atom, a halogen atom, a lower alkyl group, or a lower alkoxy group, or salt of said isoindoline derivative.

2. The isoindoline derivative, or salt thereof, of claim 1, wherein R[2] is a hydrogen atom and R[3] is a hydroxy group.

* * * * *

UNITED STATES PATENT AND TRADEMARK OFFICE
CERTIFICATE OF CORRECTION

PATENT NO. : 5,026,856

DATED : JUNE 25, 1991

INVENTOR(S) : TAKASHI YATSUNAMI ET AL

It is certified that error appears in the above-identified patent and that said Letters Patent is hereby corrected as shown below:

Column 93, line 23, delete "a t", insert --at--.

Column 94, line 28, delete "$C_5-C_{10}$", insert --$C_6-C_{10}$--;
    line 36, before "group", insert --mercapto-- and
        before "aroylamino", insert --$C_6-C_{10}$--;
    line 42, before "arylsulfonyl", insert --$C_6-C_{10}$--;
    line 48, before "group", insert --mercapto--;
    line 50, before "arylsulfonamine" insert --$C_6-C_{10}$--.

Signed and Sealed this

Seventh Day of September, 1993

Attest:

BRUCE LEHMAN

Attesting Officer

Commissioner of Patents and Trademarks